United States Patent [19]

Soll et al.

[11] Patent Number: 5,891,909
[45] Date of Patent: Apr. 6, 1999

[54] AMIDINOHYDRAZONES AS PROTEASE INHIBITORS

[75] Inventors: Richard M. Soll, Lawrenceville, N.J.; Tianbao Lu, Exton, Pa.; Cynthia L. Fedde, Warrington, Pa.; Bruce E. Tomczuk, Collegeville, Pa.; Carl Illig, Phoenixville, Pa.

[73] Assignee: 3-Dimensional Pharmaceuticals, Inc., Exton, Pa.

[21] Appl. No.: 828,160

[22] Filed: Mar. 27, 1997

Related U.S. Application Data

[60] Provisional application No. 60/014,317 Mar. 29, 1996.
[51] Int. Cl.[6] .................. A61K 31/155; A61K 31/255; C07C 281/18; C07C 309/73
[52] U.S. Cl. .................. 514/517; 514/309; 514/312; 514/345; 514/361; 514/401; 514/406; 514/518; 514/530; 514/567; 514/632; 546/141; 546/172; 546/290; 548/127; 548/353.1; 548/367.1; 549/230; 558/56; 560/303; 562/431; 562/432; 564/228
[58] Field of Search .................. 558/56; 514/517, 514/518; 564/228

[56] References Cited

U.S. PATENT DOCUMENTS

| | | | |
|---|---|---|---|
| 3,271,448 | 9/1966 | Augstein et al. | 260/564 |
| 4,226,885 | 10/1980 | Orzalesi et al. | 424/303 |
| 4,499,082 | 2/1985 | Shenvi et al. | 514/2 |
| 4,665,085 | 5/1987 | Coquelet et al. | 514/398 |
| 4,727,064 | 2/1988 | Pitha | 514/58 |
| 4,764,604 | 8/1988 | Müller | 536/103 |
| 4,824,849 | 4/1989 | Baldwin et al. | 514/267 |
| 5,024,998 | 6/1991 | Bodor | 514/58 |
| 5,296,498 | 3/1994 | Malen et al. | 514/401 |
| 5,466,811 | 11/1995 | Alexander | 546/283 |

FOREIGN PATENT DOCUMENTS

1 263 762  3/1968  Germany .

OTHER PUBLICATIONS

Campi et al., Aust. J. Chem., 49, 219–230 (1996).
Baugh, R.J., and Travis, J., "Human Leukocyte Granule Elastase: Rapid Isolation and Characterization," *Biochemistry* 15(4):836–841 (1976).
Cleason, G., "Synthetic peptides and peptidomimetics as substrates and inhibitors of thrombin and other proteases in the blood coagulation system," *Blood Coagulation and Fibrinolysis* 5:411–436 (1994).
Corey, E.J., and Schmidt, G., "Useful Procedures for the Oxidation of Alcohols Involving Pyridinium Dichromate in Aprotic Media," *Tetrahedron Lett.* 5:399–402 (1979).
Corey, E.J., and Suggs, J.W., "Pyridinium Chlorochromate. An Efficient Reagent for Oxidation of Primary and Secondary Alcohols to Carbonyl Compounds," *Tetrahedron Lett.* 31:2647–2650 (1975).
Coughlin, S.R., "Molecular Mechanisms of Thrombin Sighnaling," *Seminars in Hematology* 31(4):270–277 (1994).
Cuypers, H.T., et al., "Sulfhydryl Content of Bovine Eye Lens Leucine Aminopeptidase," *J. Biol. Chem.* 257(12):7086–7091 (1982).
Godfrey, J.D., Jr., et al., "Synthesis of Peptide Derived Amino Alcohols II. Synthetic Methodology for the Preparation of Tertiary Alcohols," *Tetrahedron Lett.* 28(15):1603–1606 (1987).
Harker, L.A., "Strategies for Inhibiting the effects of thrombin," *Blood Coagulation and Fibrinolysis* 5(Suppl. 1):S47–S58 (1994).
Lefkovits, J., and Topol, E.J., "Direct Thrombin Inhibitors in Cardiovascular Medicine," *Circulation* 90(3):1522–1536 (1994).
Notari, R.E., "Theory and Practice of Prodrug Kinetics," *Methods in Enzymology* 112:309–323 (1985).
Sauliner, M.G., et al., "An Efficient Method for the Synthesis of Guanidino Prodrugs," *Bioorg. & Medicinal Chem. Lett.* 4(16):1985–1990 (1994).
Tapparelli, C., et al., "Synthetic low–molecular weight thrombin inhibitors: molecular design and pharmacologial profile," *Trends in Pharm. Sci.* 14:366–376 (1993).
English language abstract of German Patent No, 1 263 762 (Document AL1), *Chemical Abstracts* 69(17):6325–6326 (Abstract 67624z) (1968).
Ackerley, N. et al., "A Novel Approach to Dual–Acting Thromboxane Receptor Antagonist/Synthase Inhibitors Based on the Link of 1,3–Dioxane–Thromboxane Receptor Antogonists and –Thromboxane Synthesis Inhibitors," *Chem. Abst.* 123(21):34 (Abstract No. 275234) (1995).
Mizuno, K. et al., "Studies on antidiabetic agents. V. Synthesis of the metabolites of 5–(3–ethoxy–4–pentyloxyphenyl)–2,4–thiazolidione (CT–112) and related compounds," *Chem. Abst.* 101(7):612 (abstract No. 54974) (1984).
Svoboda, J. and Palecek, J., "Synthesis of N–[(3–substituted phenoxy)alkyl]acetohydroxamic acids, potential inhibitors of the enzyme 5–lipoxygenase," *Chem. Abtr.* 116(13)824 (Abstract No. 128264) (1992).

*Primary Examiner*—Johann Richter
*Assistant Examiner*—Jane C. Oswecki
*Attorney, Agent, or Firm*—Sterne, Kessler, Goldstein & Fox P.L.L.C.

[57] ABSTRACT

Amidino and benzamidino compounds, including compounds of the formula:

$$R^4 \diagdown_{\diagdown} \diagup^{Z-R^1} \diagdown Y-(CH_2)_n-C(R^7)-C(R^8)(R^{8'})-C(R^9)=N-N(R^a)-C(NR^bR^c)(NR^a) \quad I$$

wherein $R^1-R^4$, $R^6-R^9$, Y, Z, n and m are set forth in the specification, as well as hydrates, solvates or pharmaceutically acceptable salts thereof, that inhibit proteolytic enzymes such as thrombin are described. Also described are methods for preparing the compounds of Formula I.

76 Claims, No Drawings

AMIDINOHYDRAZONES AS PROTEASE INHIBITORS

This application claims the benefit, under 35 U.S.C. §19(e), of the earlier filing date of U.S. provisional application, application Ser. No. 60/014,317, filed Mar. 29, 1996.

BACKGROUND OF THE INVENTION

1. Field of the Invention

The present invention relates to novel compounds that function as enzyme inhibitors, and particularly to a new class of non-peptidic inhibitors of proteolytic enzymes.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257: 7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs,* Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons (Tapparelli et al., *Trends in Pharmacological Sciences* 14: 366–376 (1993); Lefkovits and Topol, *Circulation* 90(3): 1522–1536 (1994); Harker, *Blood Coagulation and Fibrinolysis* 5 (Suppl 1): S47–S58 (1994)). Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4): 270–277 (1994)), and autoamplifies its own production through a feedback mechanism. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; and Down's syndrome.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5: 411–436 (1994); Harker, *Blood Coagulation and Fibrinolysis* 5 (Suppl 1): S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3): 1522–1536 (1994); Harker, *Blood Coagulation and Fibrinolysis* 5 (*Suppl* 1): S47–S58 (1994)).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to novel compounds having Formula I (below). Also provided are processes for preparing compounds of Formula I. The novel compounds of the present invention are potent inhibitors of proteases, especially trypsin-like serine proteases, such as chymotrypsin, trypsin, thrombin, plasmin and factor Xa. Compounds of the present invention exhibit antithrombotic activity via direct, selective inhibition of thrombin, or are intermediates useful for forming compounds having such activity. Compounds of the present invention are expected to inhibit trypsin and/or chymotrypsin, and are therefore useful in treating pancreatitis. Also provided are methods of inhibiting or treating aberrant proteolysis in a mammal and methods of treating thrombosis, ischemia, stroke, restenosis or inflammation in a mammal by administering an effective amount of a compound of Formula I. Further provided are pharmaceutical compositions comprising a compound of Formula I and one or more pharmaceutically acceptable carriers or diluents. Further provided are methods of synthesizing compounds of Formula L Further provided are novel aldehyde and ketone intermediates of Formula III.

DETAILED DESCRIPTION OF THE PREFERRED EMBODIMENTS

Compounds of the present invention include compounds of Formula I:

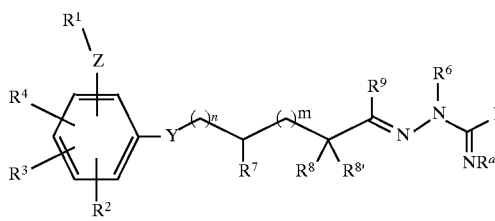

or solvates, hydrates or pharmaceutically acceptable salts thereof; wherein:

$R^1$ is one of alkyl, cycloalkyl, alkenyl, alkynyl, aryl, aralkyl or heteroaryl, any of which may be optionally substituted;

Z is one of —$NR^{10}SO_2$—, —$SO_2NR^{10}$—, —$NR^{10}C(R^yR^z)$—, —$C(R^yR^z)NR^{10}$—, —$OSO_2$—, —$SO_2O$—, —$OC(R^yR^z)$—, —$C(R^yR^z)O$—, —$NR^{10}CO$— or —$CONR^{10}$—;

$R^y$ and $R^z$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy;

$R^2$, $R^3$ and $R^4$ are each independently one of hydrogen, alkyl, cycloalkyl, alkenyl, alkynyl, aryl, aralkyl, heteroaryl, trifluoromethyl, halogen, hydroxyalkyl, cyano, nitro, carboxamido, —$CO_2R^x$, —$CH_2OR^x$ or —$OR^x$, or when present on adjacent carbon atoms, $R^2$ and $R^3$ may also be taken together to form one of —CH=CH—CH=CH— or —$(CH_2)_q$—, where q is from 2 to 6, and $R^4$ is defined as above;

$R^x$, in each instance, is independently one of hydrogen, alkyl or cycloalkyl wherein said alkyl or cycloalkyl groups may optionally have one or more unsaturations;

Y is one of —O—, —$NR^{10}$—, —S—, —$CHR^{10}$— or a covalent bond;

$R^a$, $R^b$ and $R^c$ are independently hydrogen, alkyl, hydroxy, alkoxy, aryloxy, aralkoxy, alkoxycarbonyloxy, cyano or —$CO_2R^w$;

$R^w$ is alkyl, cycloalkyl, phenyl, benzyl,

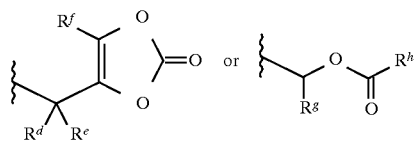

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

$R^6$ is one of hydrogen, alkyl, aralkyl, aryl, amino, hydroxyalkyl, aminoalkyl, monoalkylamino($C_{2-10}$)alkyl, dialkylamino($C_{2-10}$)alkyl or carboxyalkyl;

$R^7$ and $R^8$ are each independently one of hydrogen, alkyl, aralkyl, aryl, hydroxyalkyl or carboxyalkyl, and $R^{8'}$ is hydrogen; or $R^7$ and $R^8$ are taken together to form —$(CH_2)_y$—, where y is zero, 1 or 2, and $R^{8''}$ is hydrogen; or $R^7$ is hydrogen, and $R^8$ and $R^{8'}$ are taken together to form —$CH_2)_t$—, where t is from 2 to 5;

$R^9$ is one of hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^{10}$, in each instance, is independently one of hydrogen, alkyl, aralkyl, aryl, hydroxyalkyl, aminoalkyl, monoalkylamino($C_{2-10}$)alkyl, dialkylamino($C_{2-10}$)alkyl, carboxyalkyl or alkoxycarbonylalkyl;

n is from zero to 8; and m is from zero to 4.

A preferred group of compounds falling within the scope of the present invention include compounds of Formula I wherein:

Z is one of —$SO_2O$—, —$SO_2NR^{10}$—, —$C(R^yR^z)O$— or —$OC(R^yR^z)$—, where $R^y$ and $R^z$ are each hydrogen;

$R^1$ is one of $C_{6-10}$ aryl, pyridinyl, thiophenyl (i.e., thiophene) quinazolinyl, quinolinyl or tetrahydroquinolinyl, any of which is optionally substituted by one or two of hydroxy, nitro, trifluoromethyl, halogen, $C_{1-6}$ alkyl, $C_{1-6}$ alkoxy, $C_{1-6}$ aminoalkyl, $C_{1-6}$ aminoalkoxy, amino, mono($C_{1-4}$)alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, $C_{2-10}$ mono(carboxyalkyl)amino, di($C_{2-10}$ carboxyalkyl)amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{6-10}$ arylsulfonyl, $C_{6-10}$ ar($C_{1-6}$) alkylsulfonyl, mono- and di-(($C_{1-4}$)alkyl)aminosulfonyl, mono- and di-(($C_{6-10}$)aryl)aminosulfonyl, mono- and di-($C_{6-10}$ ar($C_{1-4}$)alkyl)aminosulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, N-morpholinosulfonyl, N-piperazinylsulfonyl (optionally N' substituted with $C_{1-6}$ alkyl, $C_{1-6}$ hydroxyalkyl, $C_{6-10}$ aryl or $C_{6-10}$ aryl($C_{1-6}$)alkyl), N-pyrrolylsulfonyl, N-piperidinylsulfonyl, N-pyrrolidinylsulfonyl, N-dihydropyridylsulfonyl, N-indolylsulfonyl, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, and perfluoroethoxy;

$R^2$, $R^3$ and $R^4$ are independently one of hydrogen, $C_{1-6}$ alkyl, $C_{3-8}$ cycloalkyl, phenyl, benzyl, trifluoromethyl, halogen, hydroxy($C_{1-8}$)alkyl, cyano, nitro, carboxamido, carboxy, $C_{1-4}$ alkoxycarbonyl, $C_{1-4}$ alkoxymethyl or $C_{1-4}$ alkoxy; or alternatively, $R^2$ and $R^3$, when present on adjacent carbon atoms, may also be taken together to form one of —CH=CH—CH=CH— or —$(CH_2)_q$—, where q is from 2 to 6, and $R^4$ is as defined above;

Y is one of —O—, —S—, —$NR^{10}$—, or a covalent bond;

$R^a$, $R^b$ and $R^c$ are each one of hydrogen, $C_{1-4}$ alkyl, hydroxy, $C_{1-4}$ alkoxy, phenoxy, $C_{1-4}$ alkyloxycarbonyl, benzyloxycarbonyl, cyano,

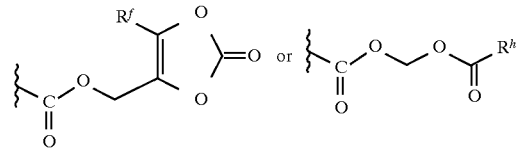

where $R^h$ is benzyl, methyl, ethyl, isopropyl, sec-butyl or t-butyl, and where $R^f$ is hydrogen or $C_{1-6}$ alkyl;

$R^6$ is one of hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, mono $(C_{1-4})$alkylamino$(C_{2-8})$alkyl, di$(C_{1-4})$alkylamino$(C_{2-8})$alkyl or $C_{2-10}$ carboxyalkyl;

$R^7$ and $R^8$ are independently one of hydrogen, $C_{1-6}$ alkyl, $C_{2-10}$ carboxyalkyl or $C_{2-10}$ hydroxyalkyl, or $R^7$ and $R^8$ are taken together to form —(CH$_2$)$_y$— where y is zero, 1 or 2;

$R^{8'}$ is hydrogen;

$R^9$ is hydrogen, or $C_{1-10}$ alkyl, optionally substituted with amino, mono$(C_{1-4})$alkylamino, $C_{1-6}$ alkoxy, hydroxy, carboxy, phenyl, alkyloxycarbonyl, aralkoxycarbonyl, $C_{1-6}$ acylamino, cyano or trifluoromethyl;

$R^{10}$, in each instance, is independently hydrogen, $C_{1-6}$ alkyl, benzyl, phenyl, $C_{2-10}$ hydroxyalkyl, $C_{2-10}$ aminoalkyl, $C_{1-4}$ monoalkylamino$(C_{2-8})$alkyl, $C_{1-4}$ dialkylamino$(C_{2-8})$alkyl or $C_{2-10}$ carboxyalkyl;

n is from zero to 8; and m is from zero to 4.

An especially preferred group of compounds include compounds of Formula I wherein:

Z is one of —SO$_2$O—, —SO$_2$NR$^{10}$—, —CH$_2$O— or —OCH$_2$—;

$R^1$ is one of phenyl, naphthyl, pyridyl, thiophenyl, quinolinyl or isoquinolinyl, any of which can be optionally substituted by one or two of chloro, trifluoromethyl, amino or dimethylamino;

$R^2$ and $R^3$ are each hydrogen or $R^2$ and $R^3$ may also be taken together to form —CH=CH—CH=CH—; $R^4$ is one of hydrogen, methyl, methoxy or trifluoromethyl;

Y is one of O, NR$^{10}$ or a covalent bond;

$R^a$, $R^b$ and $R^c$ are hydrogen, hydroxy,

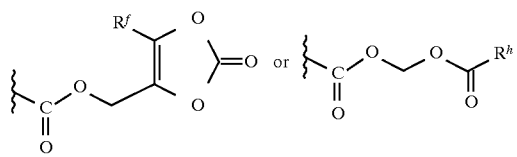

where $R^h$ is benzyl or t-butyl, and where $R^f$ is hydrogen or methyl;

$R^6$ is hydrogen, $C_{1-4}$ alkyl, $C_{2-4}$ hydroxyalkyl, $C_{2-4}$ carboxyalkyl, $C_{2-4}$ aminoalkyl, dimethylamino$(C_{2-8})$alkyl, or methylamino$(C_{2-8})$alkyl;

$R^7$ and $R^8$ are independently one of hydrogen, $C_{1-6}$ alkyl, $C_{2-10}$ hydroxyalkyl or $C_{2-10}$ carboxyalkyl, or $R^7$ and $R^8$ are taken together to form —(CH$_2$)$_y$— where y is zero, 1 or 2;

$R^{8'}$ is hydrogen;

$R^9$ is hydrogen or $C_{1-4}$ alkyl;

$R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino$(C_{2-8})$alkyl, methylamino$(C_{2-8})$alkyl;

n is from zero to 4; and m is zero, 1, 2 or 3.

The moiety —Z—R$^1$ of Formula I is attached to the benzene ring in a position ortho-, meta- orpara- to Y. Preferred compounds are those of Formula I where the moiety —Z—R$^1$ is attached in the meta- or para-position, with the meta-position being most preferred.

Preferred compounds of the present invention are those of Formula I wherein Y is one of divalent oxygen (—O—, —NR$^{10}$— or a covalent bond, and Z is one of —SO$_2$NR$^{10}$—, —SO$_2$O— or —CH$_2$O—.

Preferred compounds of the present invention are those of Formula I wherein $R^1$ is one of $C_{1-12}$ alkyl, especially $C_{3-8}$ alkyl, $C_{4-7}$ cycloalkyl, $C_{2-8}$ alkenyl, $C_{2-8}$ alkynyl or $C_{6-14}$ aryl, especially $C_{6-10}$ aryl, any of which is optionally substituted. Substituents that can be optionally present on the $R^1$ moieties include one or more, preferably one or two, hydroxy, nitro, trifluoromethyl, halogen, alkoxy, aminoalkoxy, aminoalkyl, hydroxyalkyl, hydroxyalkoxy, cyano, amino, monoalkylamino, dialkylamino, carboxy, carboxyalkyl, carboxyalkoxy, mono(hydroxyalkyl)amino, di(hydroxyalkyl)amino, mono(carboxyalkyl)amino, di(carboxyalkyl)amino, alkoxycarbonylamino, alkoxycarbonyl, aralkoxycarbonyl, alkenylcarbonyl, alkynylcarbonyl, alkylsulfonyl, alkenylsulfonyl, alkynylsulfonyl, arylsulfonyl, aralkylsulfonyl, mono- and di-(alkyl)aminosulfonyl, mono- and di-(aryl)aminosulfonyl, mono- and di-(aralkyl)aminosulfonyl, alkylsulfinyl, alkylsulfonamido, arylsulfonamido, aralkylsulfonamido, N-morpholinosulfonyl, N-piperazinylsulfonyl (optionally N' substituted with alkyl, hydroxyalkyl, aryl or arylalkyl), N-pyrrolylsulfonyl, N-piperidinylsulfonyl, N-pyrrolidinylsulfonyl, N-dihydropyridylsulfonyl, N-indolylsulfonyl, amidino, guanidino, alkyliminoamino, formyliminoamino, trifluoromethoxy or perfluoroethoxy. A further substituent on aryl, cycloalkyl, alkenyl, alkynyl and aralkyl moities of $R^1$ includes one or more, preferably one or two, alkyl moieties.

Preferred values of optional substituents on $R^1$ include hydroxy, nitro, trifluoromethyl, halogen, $C_{1-6}$ alkyl, $C_{1-6}$ alkoxy, $C_{1-6}$ aminoalkyl, $C_{1-6}$ aminoalkoxy, amino, mono$(C_{1-4})$alkylamino, di$(C_{1-4})$alkylamino, $C_{2-6}$ alkoxycarbonylamino, $C_{2-6}$ alkoxycarbonyl, carboxy, $C_{1-6}$ hydroxyalkyl, $C_{2-10}$ mono(carboxyalkyl)amino, di$(C_{2-10}$ carboxyalkyl)amino, $C_{6-14}$ ar$(C_{1-6}$ alkoxycarbonyl, $C_{2-6}$ alkynylcarbonyl, $C_{1-6}$ alkylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, carboxyalkylamino, cyano, trifluoromethoxy, and perfluoroethoxy.

Additional preferred values of optional substituents on $R^1$ include $C_{6-10}$ arylsulfonyl, $C_{6-10}$ ar$(C_{1-6})$ alkylsulfonyl, mono- and di$((C_{1-4})$alkyl)aminosulfonyl, mono- and di-($(C_{6-10})$aryl)aminosulfonyl, mono- and di-$(C_{6-10}$ ar$(C_{1-4})$ alkyl)aminosulfonyl, $C_{6-10}$ arylsulfonamido, $C_{6-10}$ ar$(C_{1-6})$ alkylsulfonamido, N-morpholinosulfonyl, N-piperazinylsulfonyl (optionally N' substituted with $C_{1-6}$ alkyl, $C_{1-6}$ hydroxyalkyl, $C_{6-10}$ aryl or $C_{6-10}$ aryl$(C_{1-6})$ alkyl), N-pyrrolylsulfonyl, N-piperidinylsulfonyl, N-pyrrolidinylsulfonyl, N-dihydropyridylsulfonyl and N-indolylsulfonyl.

An additional preferred group of compounds are those compounds of Formula I wherein $R^1$ is heteroaryl or substituted heteroaryl. Preferred $R^1$ heteroaryl groups include pyridyl, pyrazolyl, thiophenyl, chromenyl, benzoxazolyl, benzthiadiazolyl, quinazolinyl, quinolinyl, isoquinolinyl and tetrahydroquinolinyl, with thiophenyl, quinazolinyl, quinolinyl and tetrahydroquinolinyl being more preferred and thiophenyl, isoquinolinyl and quinolinyl especially preferred. Preferred compounds when $R^1$ is substituted heteroaryl include those compounds having one of the heteroaryl groups mentioned as preferred that have one or more, preferably one or two, substituents that are listed in the preceding paragraph. Preferred substituents when $R^1$ is substituted heteroaryl include one or more substituents, preferably 1 to 3 substituents, independently selected from halogen, $C_{1-6}$alkyl, $C_{1-6}$alkoxy, amidino, guanidino, carboxyalkoxy, carboxyalkylamino, amino, monoC$_{1-6}$alkylamino and/or di$(C_{1-6})$alkylamino.

Useful values of $R^1$ include phenyl, chlorophenyl, iodophenyl, dichlorophenyl, bromophenyl, trifluoromethylphenyl, di(trifluoromethyl)phenyl, methylphenyl, t-butylphenyl, methoxyphenyl, dimethoxyphenyl, hydroxyphenyl, carboxyphenyl, aminophenyl, methylaminophenyl, n-butylaminophenyl, amidinophenyl, guanidinophenyl, formyliminoaminophenyl, acetimidoylaminophenyl, methoxycarbonylphenyl, ethoxycarbonylphenyl, carboxymethoxyphenyl, naphthyl, hydroxynaphthyl, cyclohexyl, cyclopentyl, 2-propylbutyl, 8-quinolinyl, 5-methyl-8-quinolinyl, 4-benzo-2,1,3-thiadiazolyl, 5-chloro-2-thiophenyl, 5-chloro-1,3-dimethyl-4-pyrazolyl, pyridyl and tetrahydroquinolinyl.

The groups $R^2$, $R^3$ and $R^4$ in Formula I substitute for any remaining hydrogen atoms on the benzene ring after allowing for attachment of the moiety —Z—$R^1$. Preferred compounds are those where $R^2$, $R^3$ and $R^4$ are independently hydrogen, $C_{1-4}$ alkyl, $C_{4-7}$ cycloalkyl, $C_{6-14}$ aryl, especially $C_{6-10}$ aryl, $C_{6-10}$ ar($C_{1-4}$)alkyl, trifluoromethyl, halogen, hydroxyalkyl, cyano, nitro, carboxamide, carboxy, alkoxycarbonyl, carboxymethyl, alkoxycarbonylmethyl, or cycloalkyloxycarbonyl.

Alternatively, $R^2$ and $R^3$, when attached to adjacent carbon atoms on the benzene ring, are one of —CH=CH—H=CH— or —(CH$_2$)$_q$—, where q is from 2 to 6, thereby forming a fused ring. Preferred values when $R^2$ is taken together with $R^3$ include —CH=CH—CH=CH—, —CH$_2$—CH$_2$—CH$_2$— and —CH$_2$—CH$_2$—CH$_2$—CH$_2$—. When $R^2$ and $R^3$ together form a fused ring, $R^4$ is preferably hydrogen.

Useful values of $R^2$, $R^3$ and $R^4$ include hydrogen, methyl, ethyl, chloro, bromo, trifluoromethyl, hydroxymethyl, methoxy, ethoxy, carboxamide, nitro, phenyl, cyclopropyl, hydroxy, isopropyl, methoxycarbonyl, ethoxycarbonyl and benzyl. Useful values of $R^2$, $R^3$ and $R^4$ also include $R^2$ and $R^3$ together forming —CH=CH—CH=CH or —CH$_2$—CH$_2$—CH$_2$— and $R^4$ being hydrogen.

Preferred values of $R^a$, $R^b$ and $R^c$ in Formula I are hydrogen, hydroxy, $C_{1-6}$ alkyl, $C_{1-6}$ alkoxy, cyano or —CO$_2R^w$, where $R^w$, in each instance, is preferably one of $C_{1-4}$alkyl, $C_{4-7}$cycloalkyl or benzyloxycarbonyl. Suitable values of $R^6$ include hydrogen, methyl, ethyl, propyl, n-butyl, hydroxy, methoxy, ethoxy, cyano, —CO$_2$CH$_3$, —CO$_2$CH$_2$CH$_3$ and —CO$_2$CH$_2$CH$_2$CH$_3$. In the most preferred embodiments, $R^a$, $R^b$ and $R^c$ are each hydrogen.

Also preferred at $R^a$, $R^b$ and $R^c$ is the group —CO$_2R^w$, where $R^w$ is one of

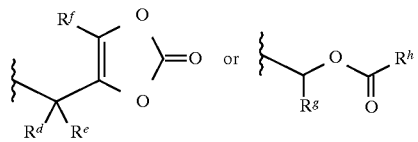

where $R^d$–$R^h$ are defined as above. When $R^a$, $R^b$ and $R^c$ are —CO$_2R^w$, where $R^w$ is one of one of these moieties, the resulting compounds are prodrugs that possess desirable formulation and bioavailability characteristics. A preferred value for each of $R^d$, $R^e$, and $R^g$ is hydrogen, $R^f$ is methyl and preferred values for $R^h$ include benzyl and tert-butyl.

Preferred compounds include compounds of Formula I, where $R^7$ and $R^8$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl, and $R^8$ is hydrogen; or $R^7$ and $R^8$ are taken together to form —(CH$_2$)$_y$—, where y is most preferably 2, and $R^{8'}$ is hydrogen. Useful values of $R^7$ and $R^8$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl.

Another preferred embodiment includes compounds of Formula I, where $R^7$ is hydrogen, and $R^8$ and $R^{8'}$ are taken together to form —(CH$_2$)$_t$—, where t is defined above, and is most preferably 2. In this embodiment m and n are preferably both zero.

Preferred compounds are those of Formula I, wherein $R^6$ is hydrogen, amino or $C_{1-6}$alkyl.

Preferred compounds are those of Formula I, wherein $R^9$ is hydrogen or $C_{1-6}$alkyl optionally substituted by one, two or three of, preferably one of, amino, monoalkylamino, dialkylamino, alkoxy, hydroxy, alkoxycarbonyl, aryloxycarbonly, aralkoxycarbonyl, carboalkoxy, phenyl, cyano, trifluoromethyl, acetylamino, pyridyl, thienyl, furyl, pyrrolyl or imidazolyl.

Suitable values of $R^9$ include hydrogen, methyl, ethyl, propyl, n-butyl, benzyl, phenethyl, 2-hydroxyethyl, 3-hydroxypropyl, 4-hydroxybutyl, carboxymethyl and carboxyethyl.

Preferred values of $R^{10}$ in Formula I include hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, $C_{2-7}$ carboxyalkyl, C1-4 alkoxycarbony($C_{2-10}$)alkyl mono($C_{1-4}$ alkyl)amino($C_{1-8}$) alkyl, and di($C_{1-4}$alkyl)amino($C_{1-8}$)alkyl. Suitable values of $R^{10}$ include methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl, 2-ethoxycarbonylpentyl and 2-(dimethylamino)ethyl.

Preferred values of n in Formula I include from zero to 6, more preferably from zero to 4, and most preferably zero, 1 or 2. Preferred values of m include from zero to 4, more preferably zero, 1, 2 or 3 and most preferably zero or 1.

Compounds having the following formulas (Formula IA and Formula IB) have been discovered to have exceptional potency as serine protease inhibitors:

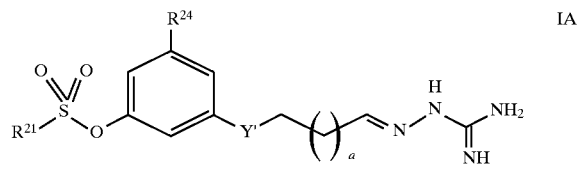

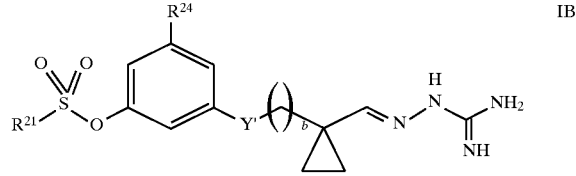

or solvates, hydrates, pharmaceutically acceptable salts or prodrugs thereof; wherein $R^{21}$ is one of phenyl, naphthyl, thiophenyl, pyridyl, pyrazolyl, benzthiadiazolyl, quinolinyl, or isoquinolinyl, any of which optionally substituted by one, two or three substituents independently selected from the group consisting of fluoro, chloro, bromo, $C_{1-4}$ alkyl, $C_{1-4}$ alkoxy, trifluoromethyl, cyano, nitro, amino or dimethylamino;

$R^{24}$ is hydrogen or $C_{1-4}$ alkyl;

Y' is one of O, NH or a covalent bond; and a and b are 0, 1 or 2, preferably 1.

Specific compounds within the scope of the invention include the following:

2-[2-[3-(2-chlorophenylsulfonyloxy)-5-methylphenoxy] ethyl-1-methylene]hydrazinecarboximidamide hydrochloride;

2-[2-[5-methyl-3-(2-trifluoromethylphenylsulfonyloxy) phenoxy]ethyl-1-methylene]hydrazinecarboximidamide nitrate;

2-[2-[5-methyl-3-(2-trifluoromethylbenzyloxy)phenoxy] ethyl-1-methylene]hydrazinecarboximidamide nitrate;

2-[3-[3-(2-chlorophenylsulfonyloxy)-5-methoxyphenyl] propyl-1-methylene]hydrazinecarboximidamide hydrochloride;

2-[2-[(5-methyl-3-(N-(5-ethoxycarbonylpentyl)-N-(2-trifluoromethylphenylsulfonyl)amino)phenoxy]ethyl-1-methylene]hydrazinecarboximidamide nitrate;

2-[2-[3-(2,3-dichlorophenylsulfonyloxy)-5-methylphenoxy] ethyl-1-methylene]hydrazinecarboximidamide nitrate;

2-[2-[3-(2,5-dichlorophenylsulfonyloxy)-5-methylphenoxy] ethyl-1-methylene]hydrazinecarboximidamide nitrate;

2-[2-[3-(2-methoxyphenylsulfonyloxy)-5-methylphenoxy] ethyl-1-methylene]hydrazinecarboximidamide acetate;

2-[2-[3-(5-bromo-2-methoxyphenylsulfonyloxy)-5-methylphenoxy]ethyl-1-methylene] hydrazinecarboximidamide nitrate;

2-[2-[5-methyl-3-(2-trifluoromethoxyphenylsulfonyloxy) phenoxy]ethyl-1-methylene]hydrazinecarboximidamide nitrate;

2-[2-[3-(benzo-2, 1,3-thiodiazole-4-sulfonyloxy)-5-methylphenoxy]ethyl-1-methylene] hydrazinecarboximidamide nitrate;

2-[2-[5-methyl-3-(3-methylphenylsulfonyloxy)phenoxy] ethyl-1-methylene]hydrazinecarboximidamide nitrate;

2-[2-[3-(2-cyanophenylsulfonyloxy)-5-methylphenoxy] ethyl-1-methylene]hydrazinecarboximidamide hydrochloride;

2-[2-[3-(2-methoxy-5-methylphenylsulfonyloxy)-5-methylphenoxy]ethyl-1-methylene] hydrazinecarboximidamide nitrate;

2-[2-[5-methyl-3-(quinolinyl-8-sulfonyloxy)phenoxy]ethyl-1-methylene]hydrazinecarboximidamide acetate;

2-[2-[3-(2,5-dimethoxyphenylsulfonyloxy)-5-methylphenoxy]ethyl-1-methylene] hydrazinecarboximidamide nitrate;

2-[2-[3-(2,5-dimethylphenylsulfonyloxy)-5-methylphenoxy]ethyl-1-methylene] hydrazinecarboximidamide nitrate;

2-[2-[3-(5-chloro-2-methoxyphenylsulfonyloxy)-5-methylphenoxy]ethyl-1-methylene] hydrazinecarboximidamide hydrochloride;

2-[2-[3-(5-chlorothiophenyl-2-sulfonyloxy)-5-methylphenoxy]ethyl-1-methylene] hydrazinecarboximidamide nitrate;

2-[2-[3-(5-chloro-1,3-dimethylpyrazole-4-sulfonyloxy)-5-methylphenoxy]ethyl-1-methylene] hydrazinecarboximidamide acetate;

2-[2-[3-(3-chlorophenylsulfonyloxy)-5-methylphenoxy] ethyl-1-methylene]hydrazinecarboximidamide nitrate;

2-[2-[5-methyl-3-(2-methyl-5-nitrophenylsulfonyloxy) phenoxy]ethyl-1-methylene]hydrazinecarboximidamide nitrate;

2-[3-[3-(2-methoxyphenylsulfonyloxy)-5-methylphenoxy] propyl-1-methylene]hydrazinecarboximidamide nitrate;

2-[2-[3-(5-fluoro-2-methylphenylsulfonyloxy)-5-methylphenoxy]ethyl 1-methylene] hydrazinecarboximidamide nitrate;

2-[2-[5-methyl-3-(1-naphthalenylsulfonyloxy)phenoxy] ethyl-1-methylene]hydrazinecarboximidamide nitrate;

2-[2-[3-(2-chloro-5-trifluoromethylphenylsulfonyloxy)-5-methylphenoxy]ethyl-1-methylene] hydrazinecarboximidamide nitrate;

2-amino-[2-[2-[3-(5-chloro-2-methoxyphenylsulfonyloxy)-5-methylphenoxy]ethyl-1-methylene]hydrazine] carboximidamine acetate;

1-amino-2-[2-[3-(5-chloro-2-methoxyphenylsulfonyloxy)-5-methylphenoxy]ethyl-1-methylene] hydrazinecarboximidamine acetate;

2-[3-(2-methoxyphenylsulfonyloxy)-5-methylphenoxy] methyl-1-methylene]hydrazinecarboximidamide nitrate;

2-[2-[3-(2-cyano-5-methylphenylsulfonyloxy)-5-methylphenoxy]ethyl-1-methylene] hydrazinecarboximidamide nitrate;

2-[2-[(3-methyl-5-(N-(4-phenylbutyl)-N-(2-trifluoromethylphenylsulfonyl))-amino)phenoxy]ethyl-1-methylene]hydrazinecarboximidarnide acetate;

2-[2-[3-(5-isoquinolinylsulfonyloxy)-5-methylphenoxy] ethyl-1-methylene]hydrazinecarboximidamide nitrate;

2-[[1-[5-methyl-3-(quinolinyl-8-sulfonyloxy)phenoxy] methyl]cyclopropyl-1-methylene] hydrazinecarboximidamide acetate;

2-[2-[5-methyl-3-(3-pyridinylsulfonyloxy)phenoxy]ethyl-1-methylene]hydrazinecarboximidamide diacetate;

2-[2-[3-(3-fluorophenylsulfonyloxy)-5-methylphenoxy] ethyl-1-methylene]hydrazinecarboximidamide nitrate;

2-[2-[3-(3-cyanophenylsulfonyloxy)-5-methylphenoxy] ethyl-1-methylene]hydrazinecarboximidamide nitrate;

2-[2-[3-(3-bromophenylsulfonyloxy)-5-methylphenoxy] ethyl-1-methylene]hydrazinecarboximidamide nitrate;

2-[2-[5-methyl-3-(2-nitrophenylsulfonyloxy)phenoxy] ethyl-1-methylene]hydrazinecarboximidamide nitrate;

2-[2-[5-methyl-3-(2-nitrophenylsulfonyloxy)phenoxy] ethyl-1-methylene]hydrazinecarboximidarnide nitrate;

2-[[ 1-[3-(2-cyanophenylsulfonyloxy)-5-methylphenoxy] methyl]cyclopropyl-1-methylene] hydrazinecarboximidamide acetate;

2-[2-[5-methyl-3-(phenylmethylsulfonyloxy)phenoxy] ethyl-1-methylene]hydrazinecarboximidamide acetate;

2-[2-[2-[3-(2-methoxyphenylsulfonyloxy)-5-methylphenoxy]ethyl-1-methylene]hydrazine]-1-(hydroxycarboximidamidine); and 2-[5-methyl-3-[2-(methylsulfonyl)phenylsulfonyloxy] phenoxy]ethyl 1-methylene]hydrazinecarboximidamide diacetate.

Alternative embodiments of the present invention include compounds of Formula I in which two "R" groups together form a saturated or unsaturated hydrocarbon bridge, thus forming an additional cyclic moiety in the resulting compounds. Alternative embodiments include compounds of Formula I wherein Z, $R^1$–$R^4$, Y, m and n are as defined above; and:

A. $R^7$ and $R^9$ are taken together to form —$(CH_2)_o$—, where o is 1, 2 or 3; $R^8$ is hydrogen, alkyl, aralkyl, aryl, hydroxyalkyl or carboxyalkyl; $R^{8'}$ is hydrogen; and $R^6$, $R^a$, $R^b$ and $R^c$ are defined as above; or B. $R^7$ is hydrogen, alkyl, aralkyl, aryl, hydroxyalkyl or carboxyalkyl; $R^{8'}$ is hydrogen; $R^8$ and $R^9$ are taken together to form —$CH_2$—$CH_2CH_2$—$(CH_2)_p$—, where p is 1, 2 or 3; and $R^6$, $R^a$, $R^b$ and $R^c$ are defmed as above; or C. $R^6$ and $R^b$ are taken together to form =CH—N=CH—NH— or —$CH_2$—$(CH_2)_r$—, where r is 1, 2 or 3; $R^a$ is hydrogen or hydroxy; $R^c$ is hydrogen, alkyl, hydroxy, alkoxy, aryloxy, aralkoxy, alkoxycarbamoyloxy, cyano or —$CO_2R^w$—, where $R^w$ is as defined above; $R^7$ and $R^8$ are each independently one of hydrogen, alkyl, aralkyl, aryl, hydroxyalkyl or carboxyalkyl, or $R^7$ and $R^8$ are taken together to form —$(CH_2)_y$—, where y is zero, 1 or 2; $R^{8'}$ is hydrogen; and $R^9$ is one of hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl; or D. $R^a$ and $R^c$ are taken together to form —$CH_2$—$(CH_2)_s$—, where s is 1 or 2; $R^6$ is hydrogen, alkyl, alkoxy, aryloxy, aralkoxy, alkoxycarbonyloxy, cyano or —$CO_2R^w$—, where $R^w$ is as defined above; $R^7$ and $R^8$ are each independently one of hydrogen, alkyl, aralkyl, aryl, hydroxyalkyl or carboxyalkyl, or $R^7$ and $R^8$ are taken together to form —$(CH_2)_y$—, where y is zero, 1 or 2; $R^{8'}$ is hydrogen; and $R^9$ is one of hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl.

Thus, compounds having formulae V, VI, VII and VIII are contemplated:

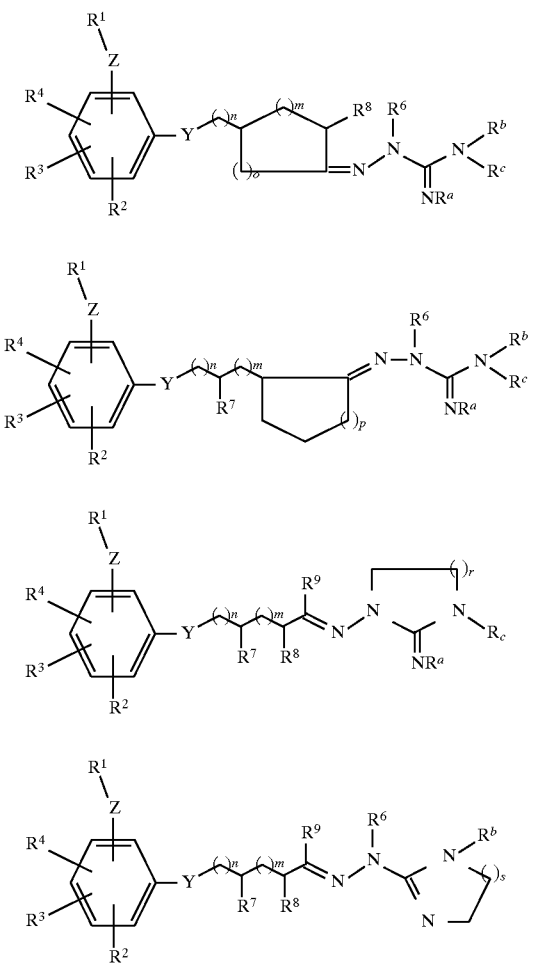

wherein $R^1$–$R^4$, Z, Y, $R^6$–$R^9$, $R^a$–$R^c$, n, m, o, p, r and s are defined as above. Preferred values for each of these variables are the same as described above for Formula I. Specific compounds within the scope of these formulae include:

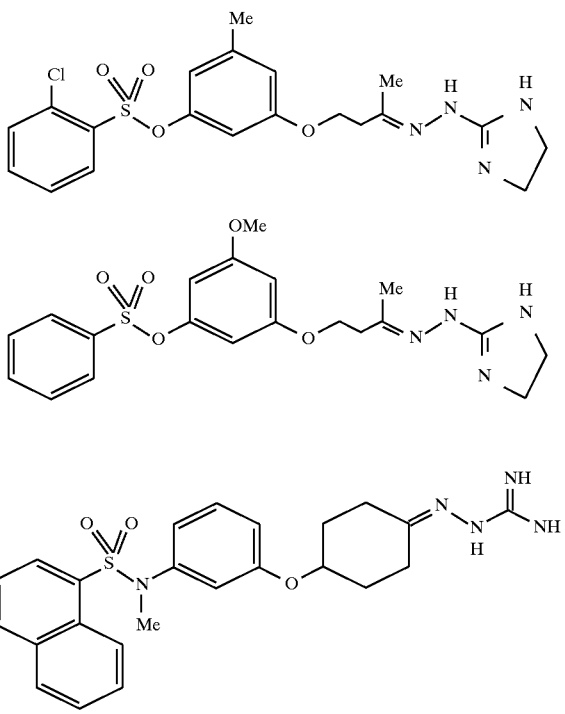

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology*, 112: 309–323 (1985); Bodor, N., "Novel Approaches in Prodrug Design," *Drugs of the Future*, 6(3): 165–182 (1981); and Bundgaard, H., "Design of Prodrugs: Bioreversible-Derivatives for Various Functional Groups and Chemical Entities," in *Design of Prodrugs* (H. Bundgaard, ed.), Elsevier, New York (1985). Useful prodrugs are those where $R^a$, $R^b$ and/or $R^c$ are —$CO_2R^w$, where $R^w$ is defined above. See, U.S. Pat. No. 5,466,811 and Saulnier et al., *Bioorg Med. Chem. Lett.* 4: 1985–1990(1994).

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to C,-alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The terms "alkoxy" refers to any of the above alkyl groups linked to an oxygen atom.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocyclic" is used herein to mean a saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quatemized, and including any bicyclic group in which any of the above-defined heterocyclic rings is fused to a benzene ring, and wherein the heterocyclic ring can be substituted on carbon or on a nitrogen atom if the resulting compound is stable. Examples include, but are not limited to, pyrrolidine, piperidine, piperazine, morpholine, imidazolidine, pyrazolidine, benzodiazepines, and the like.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

Another aspect of the present invention is a process for preparing an amidinohydrazone compound of Formula I, comprising reacting an aminoguanidine of the formula

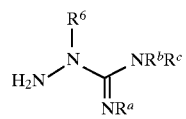

II wherein $R^6$, $R^a$, $R^b$ and $R^c$ are defined as above, with a carbonyl-containing compound of the formula:

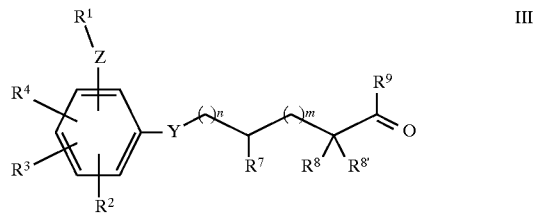

III wherein $R^1$–$R^4$, Z, Y, n, m and $R^7$–$R^9$ are defined as above for Formula I.

The aminoguanidine is typically provided as a salt, preferably the nitrate salt. The reaction proceeds at ambient temperature using alcohol as a solvent. An acid, such as 4N HCl in dioxane is added to the reaction mixture. The reaction is more fully described herein.

The invention is also directed to aldehyde and ketone intermediates that are useful for forming the protease inhibiting compounds of Formula I. These intermediates are represented by Formula III:

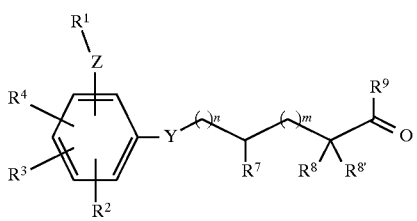

III where $R^1$–$R^4$, Y, Z, $R^7$–$R^9$, n and m are as defined for Formula I. Preferred values for each of these groups are as described above for Formula I.

Preferred compounds within the scope of Formula III are represented by Formula IV:

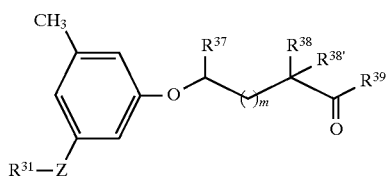

IV wherein

Z is —$SO_2O$—, —$SO_2$—$NR^{10}$— or —$CH_2$—O—;

$R^{31}$ is one of $C_{6-10}$ aryl, pyridyl, pyrazolyl, thiophenyl, chromenyl, benzoxazolyl, benzthiadiazolyl, quinazolinyl, quinolinyl, isoquinolinyl and tetrahydroquinolinyl;

$R^{37}$ and $R^{38}$ are independently one of hydrogen, $C_{1-6}$ alkyl, $C_{2-10}$ hydroxyalkyl or $C_{2-10}$ carboxyalkyl, and $R^{38'}$ is hydrogen; or $R^{37}$ and $R^{38}$ are taken together to form —$(CH_2)_y$— where y is zero, 1 or 2, and $R^{38'}$ is hydrogen; or $R^{37}$ is hydrogen, and $R^{38}$ and $R^{38'}$ are taken together to form —$(CH_2)_t$—, where t is from 2 to 5, preferably 2;

$R^{39}$ is hydrogen or $C_{1-4}$ alkyl; and m is 0, 1 or 2.

Scheme I illustrates but is not limited to the preparation of the compounds of the present invention.

Scheme I

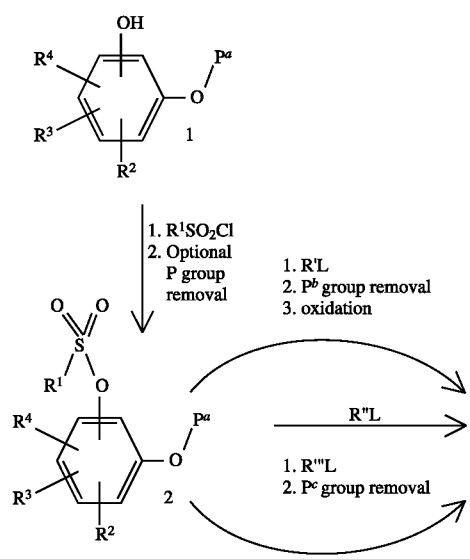

-continued
Scheme I

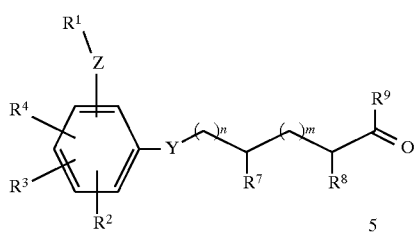

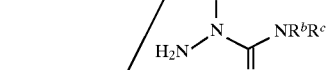

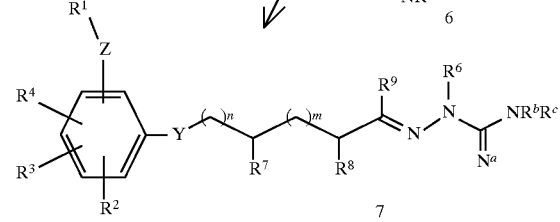

where

R'L is

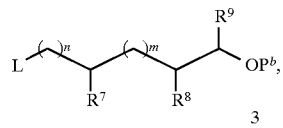

R"L is

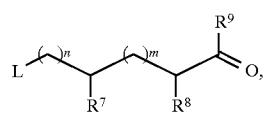

and

R'''L is the same as 4, except that the keto or aldehyde group is protected with a suitable protecting group, $P^c$, and the remaining groups are as defined above.

Phenols 1 (where P is H) are converted to monosulfonates 2 by treatment with appropriate sulfonyl chlorides. Preferred conditions include treating phenol 1 with a sulfonyl chloride in a biphasic system composed of ether and an aqueous phase saturated with $NaHCO_3$. Alternatively, the reaction may be effected first by deprotonating 1 with one equivalent of a strong base, most preferably NaH, in a polar organic solvent, such as DMF or tetrahydrofuran, followed by treating the deprotonated phenol with the sulfonyl chloride. Still alternatively, phenol 1, in a typical organic solvent, such as methylene chloride, may be converted to 2 by treating the phenol with sulfonyl chloride in the presence of an amine base, such as N-methylmorpholine.

Phenols 1 may be monoprotected (pa is a protecting group) with a variety of protecting groups known in the art, such as esters, benzyl ethers and silyl ethers (Green, T. W. and Wuts, P. G. M., *Protective Groups in Organic Synthesis,* 2nd edition, John Wiley and Sons, Inc. New York (1991)). Deprotection of the hydroxy groups is routinely accomplished using the reaction conditions well-known in the art.

For example, deprotection of benzyl ethers may be effected through catalytic hydrogenation using palladium on carbon as a catalyst in solvents such as ethanol or tetrahydrofuran. Deprotection of an acetate is accomplished by basic hydrolysis, most preferably with sodium hydroxide in aqueous tetrahydrofuran.

Phenols 2 are coupled to 3 (for L=OH) using a Mitsunobu coupling procedure (Mitsunobu, O., *Synthesis* 1 (1981)), where $P^b$ of 3 may be a suitable alcohol protecting group. Preferred coupling conditions include using a trialkylphosphine or triarylphosphine, such as triphenylphosphine, in a suitable solvent such as tetrahydrofuran or methylene chloride, and a dialkyl azodicarboxylate, such as diethyl azodicarboxylate. Typical $P^b$ are well known in the art, such as esters and benzyl ethers (Green, T. W. and Wuts, P. G. M., *Protective Groups in Organic Synthesis*, 2nd edition, John Wiley and Sons, Inc. New York (1991)). Alternatively, where L is a reactive leaving group such as halide or sulfonate, phenol 2 may be treated with a base, such as sodium hydride in a solvent such as DMF and then treated with 3. Removal of $P^b$ is routinely accomplished using the reaction conditions well-known in the art. For example, deprotection of benzyl ethers may be effected through catalytic hydrogenation using palladium on carbon as a catalyst in solvents such as ethanol or tetrahydrofuran. Deprotection of an acetate is accomplished by basic hydrolysis, most preferably with sodium hydroxide in aqueous tetrahydrofuran. The resulting alcohol is then oxidized using routine procedures for the oxidation of alcohols (see for Example Carey F. A, Sundberg, R. J., *Advanced Organic Chemistry, Part B: Reactions and Synthesis*, 3rd edition, Plenum Press, New York (1990)) such as the Swem oxidation (Mancuso et al., *Journal of Organic Chemistry:* 3329 (1976)), pyridinium chlorochromate (Corey & Suggs, *Tetrahedron Letters:* 2647 (1975)), pyridinium dichromate (Corey & Schmidt, *Tetrahedron Letters:* 399 (1979)), or sulfur trioxide pyridine complex/dimethylsulfoxide (*Tetrahedron Letters* 28: 1603 (1987)). Still alternatively, 2 may be coupled directly to 4 where L=OH or a reactive leaving group such as halide, alkyl sulfonate, or aryl sulfonate. In the case of L=OH, the Mitsunobu coupling procedure may be used. In cases where L is a reactive leaving group such as halide or sulfonate, phenol 2 may be treated with a base, such as sodium hydride in a solvent such as DMF and then treated with 4.

Alternatively, phenol 2 may be converted to 5 by the Mitsunobu coupling procedure using 4 wherein L=OH and the aldehyde or ketone is protected with a suitable protecting group, $P^c$. Such protecting groups are well known in the art (Green, T. W. and Wuts, P. G. M., *Protective Groups in Organic Synthesis*, 2nd edition, John Wiley and Sons, Inc. New York (1991)), and include, for example, a dimethyl ketal or acetal, 1,3-dioxalane, or 1,3-dioxane. Alternatively, where L of 4 is a reactive leaving group such as halide or sulfonate, phenol 2 may be treated with a base, such as sodium hydride in a solvent such as DMF and then treated with 4. The aldehyde or ketone protecting group may then be removed to afford 5 using standard conditions well known in the art, for example, TsOH in acetone (Green, T. W. and Wuts, P. G. M., *Protective Groups in Organic Synthesis*, 2nd edition, John Wiley and Sons, Inc. New York (1991)).

Compound 5 is then treated with an aminoguanidine 6, such as aminoguanidine or 2-hydrazinoimidazoline, optionally in the presence of an acid, such as nitric acid, hydrogen chloride, or hydrogen bromide, to afford 7. Useful solvents include, for example, ethanol or methanol, which may contain other solvents such as methylene chloride or tetrahydrofuran.

Compounds wherein $R^a$ and $R^c$ together form a cyclic group, such as an imidazoline, can be synthesized by employing an imidazoline in place of the aminoguanidine in Scheme 1.

Compounds wherein $R^7$ and $R^9$ or $R^8$ and $R^9$ together form a methylene linkage can be synthesized by employing as R"L a cyclic ketone having a reactive group L that is attached directly or indirectly to the carbocyclic ring. Examples. of suitable reagents for R'L include 2-hydroxycyclopentanone, 3-hydroxycyclopentanone, 2-hydroxycyclohexanone and 3-hydroxycyclohexanone.

Compounds VII wherein $R^6$ and $R^b$ are taken together with the nitrogens to which they are attached to form a ring structure are prepared by substituting a heterocyclic amine 8 (below) for the aminoguanidine 6 in Scheme 1.

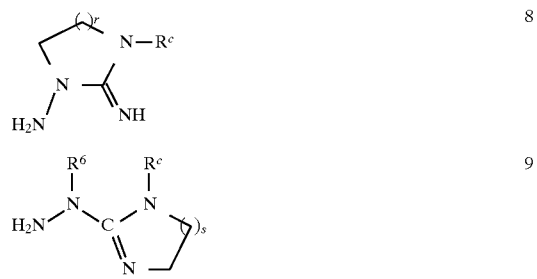

Compounds VIII wherein $R^8$ and $R^c$ are taken together with the nitrogen atoms to which they are attached to form an imidazoline moiety are prepared by substituting a 2-hydrazino-imidazoline 9 (below) for the aminoguanidine 6 in Scheme 1.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formula I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, cyclamic acid, pivalic acid and the like; useful inorganic acids are hydrohalide acids such as HCl, HBr, HI; sulfuric acid; phosphoric acid and the like. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coa.gulation pathway. Inhibition of thermolysin, a metalloprotease, and pepsin, an acid protease, are also contemplated uses of compounds of the present invention. The compounds of the present invention are preferably employed to inhibit trypsin-like proteases.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well-known in the art. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit either factor Xa or thrombin may be employed for a number of therapeutic purposes. As factor Xa or thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; hip replacement; and thrombus formation resulting from either thrombolytic therapy or percutaneous transluminal coronary angioplasty (PCTA). The compounds of the present invention may also be used as an anticoagulant in extracorporeal blood circuits.

By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses, such as edema; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

When employed as thrombin or factor Xa inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

Human leucocyte elastase is released by polymorphonuclear leukocytes at sites of inflammation and thus is a contributing cause for a number of disease states. Thus, compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described in Example 2. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15: 836 (1979). Leukocyte granules are a major source for the preparation of leukocyte elastase and cathepsin G (chymotrypsin-like activity). Leukocytes are lysed and granules are isolated. The leukocyte granules are extracted with 0.20M sodium acetate, pH 4.0, and extracts are dialyzed against 0.05M Tris buffer, pH 8.0 containing 0.05M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10M Hepes buffer, pH 7.5, containing 0.50M NaCl, 10% dimethylsulfoxide and 0.0020M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors will of course depend upon the nature and severity of the disease state, as determined by the attending diagnostician, with the range of 0.01 to 10 mg/kg of body weight, per day, being useful for the aforementioned disease states.

Compounds of the present invention that inhibit urokinase or plasminogen activator are potentially useful in treating excessive cell growth disease state. As such the compounds of the present invention may also be useful in the treatment of benign prostatic hypertrophy and prostatic carcinoma, the treatment of psoriasis, and in their use as abortifacients. For their end-use application, the potency and other biochemical parameters of the enzyme inhibiting characteristics of the compounds of the present invention are readily ascertained by standard biochemical techniques well-known in the art. Actual dose ranges for their specific end-use application will, of course, depend upon the nature and severity of the disease state of the patient or animal to be treated as determined by the attending diagnostician. It is to be expected that the general end-use application dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of this assay by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

2-[2-[3-(2-Chlorophenylsulfonyloxy)-5-methylphenoxylethyl-1-methylene] hydrazinecarboximidamide hydrochloride a) 3-(2-Chlorophenylsulfonyloxy)-5-methylphenol Orcinol monohydrate (1.42 g, 10 mmol) and 2-chlorobenzenesulfonyl chloride (2.43 g, 11 mmol) were mixed in saturated aqueous $NaHCO_3$ (30 mL) and diethyl ether (30 mL). The biphasic mixture was stirred vigorously at room temperature for 2 days. The reaction mixture was diluted with 50 mL of water and extracted into ethyl acetate (3×50 mL). The organic phase was washed with brine (2×50 mL) and dried over $Na_2SO_4$. After removing the solvent in vacuo, the residue was purified by flash column chromatography (2% ethyl acetate in dichloromethane) to give the title compound as a pale yellow liquid (2.15 g, 71%). $^1$H-NMR (300 MHz, $CDCl_3$) δ 2.22 (s, 3 H), 5.24 (s, 1 H), 6.43 (s, 1 H), 6.52 (s, 2H), 7.38 (m, 1 H), 7.60 (m, 2 H), and 7.96 (dd, 1 H, J =0.6, 3.9 Hz).

b) 1-(2-Chlorophenylsulfonyloxy)-3-(3-benzyloxy) propoxy-5-methylbenzene

Diethyl azodicarboxylate (230 μL, 1.46 mmol) was added slowly to a solution of 253 mg (0.866 mmol) 3-(2-chlorophenylsulfonyloxy)-5-methylphenol, as prepared in the preceding step, 363 mg (1.24 mmol) of 3-benzyloxypropanol, and 385 mg (1.47 mmol) of triphenylphosphine in anhydrous dichloromethane (7 mL) at 0° C. The cold bath was removed, and the reaction mixture was stirred at ambient temperature for 3 h. The reaction mixture was quenched with water (10 mL) and extracted into diethyl ether (3×20 mL). The combined organic extracts were dried ($MgSO_4$) and the product purified by flash chromatography (2:1 to 100:0 dichloromethane/petroleum ether) to afford the title compound (328.5 mg, 85% yield) as a colorless oil. $^1$H-NMR (300 MHz, $CDCl_3$) δ 7.95 (dd, 1 H, J=1.7, 7.9 Hz), 7.52–7.62 (m, 2 H), 7.28–7.38 (m, 6 H), 6.58 (br s, 1 H), 6.54 (br s, 1 H), 6.48 (t, 1 H, J=1.1 Hz), 4.51 (s, 2 H), 3.95 (t, 3 H, J=6.2 Hz), 3.62 (t, 2 H, J=6.1 Hz), 2.24 (s, 3 H), and 2.01 (pentet, 2 H, J=6.2 Hz). Mass spectrum (MALDI-TOF, α-cyano-4-hydroxycinnamic acid matrix) calcd. for $C_{23}H_{23}ClO_5S$: 469.1 (M+Na). Found: 469.1.

23 c) 3–13-(2-Chlorophenylsulfonyloxy)-5-methylphenoxy]propanol

A mixture of 328.5 mg (0.736 mmol) of 1-(2-chlorophenylsulfonyloxy)-3-(3-benzyloxy)propoxy-5-methylbenzene, as prepared in the preceding step, 66 mg of 10% palladium on carbon, and 180 μL (0.72 mmol) of 4N HCl/dioxane in 5 mL of tetrahydrofuran was hydrogenated (atmospheric pressure) at ambient temperature for 1 h. The reaction mixture was filtered through Celite and then concentrated. Purification by flash chromatography using elutions of 2–10% diethyl ether/dichloromethane gave 217 mg (83% yield) of the title compound as an oil. $^1$H-NMR (300 MHz, CDCl$_3$) δ 7.97 (dd, 1 H, J=1.4, 7.8 Hz), 7.56–7.65 (m, 2 H), 7.36–7.41 (m, 1 H), 6.60 (br s, 1 H), 6.54 (br s, 1 H), 6.50 (t, 1 H, J=2 Hz), 4.03 (t, 2 H, J=4.7 Hz), 3.92 (s, 1 H), 3.82 (q, 2 H, J=6.7 Hz), 2.24 (s, 3 H), and 1.99 (pentet, 2 H, J=6 Hz).

d) 3-[3-(2-Chlorophenylsulfonyloxy)-5-methylphenoxy]propionaldehyde

Sulfur trioxide pyridine complex (847 mg, 5.36 mmol) was added to a solution of 619 mg (1.74 mmol) of 3-[3-(2-chlorophenylsulfonyloxy)-5-methylphenoxy]propanol, as prepared in the preceding step, 411 μL (3.23 mmol) of N,N-diisopropylethylamine, and 230 μL (3.0 mmol) of anhydrous dimethyl sulfoxide in anhydrous dichloromethane (10 mL). The reaction mixture was stirred at ambient temperature for 1 h and then quenched with 10% aqueous citric acid (20 mL). The reaction mixture was extracted with diethyl ether (3×30 mL), dried (MgSO$_4$), and purified by flash chromatography (diethyl ether/petroleum ether (2:1 to 4:1)) to afford 289 mg (47% yield) of the title compound as a colorless oil. $^1$H-NMR (300 MHz, CDCl$_3$) δ 9.83 (t, 1 H, J=1.4 Hz), 7.97 (dd, 1 H), 7.56–7.65 (m, 2 H), 7.35–7.42 (m, 1 H), 6.60 (br s, 1 H), 6.57 (br s, 1 H), 6.49 (br s, 1 H), 4.19 (t, 2 H, J=6.1 Hz), 2.86 (td, 2 H, J=1.4, 6 Hz), and 2.25 (s, 3 H).

e) 2-[2-[3-(2-Chlorophenylsulfonyloxy)-5-methylphenoxy]ethyl-1-methylene]hydrazinecarboximidamide hydrochloride A solution of 289 mg (0.82 mmol) of 3-[3-(2-chlorophenylsulfonyloxy)-5-methylphenoxy]propionaldehyde, as prepared in the preceding step, 223 mg (1.62 mmol) of aminoguanidine nitrate, and 200 μL (0.80 mmol) of 4N HCl/dioxane in 3 mL of ethanol was stirred at ambient temperature overnight. The reaction mixture was treated with 10 mL of water and stirred for 15 min. The reaction mixture was treated with 1.2 mL of 2N sodium hydroxide and then extracted into dichloromethane (3×20 mL). The organic phase was washed with water (3×20 mL), dried (K$_2$CO$_3$), and concentrated to give 321.4 mg of crude product as a free base. The residue was dissolved in dichloromethane (1 mL), treated with 800 μL (3.2 mmol) of 4N HCl/dioxane solution. The solvent was removed and the product was triturated from a mixture of dichloromethane/ether/hexane to give 190 mg of the title compound as a colorless solid. $^1$H-NMR (300 MHz, DMSO-d$_6$) δ 11.58 (br s, 1 H), 7.95 (dd, 1 H, J=1.5, 7.9 Hz), 7.80–7.90 (m, 2 H), 7.52–7.61 (m, 6 H), 6.77 (s, 1 H), 6.49 (s, 1 H), 6.46 (br t, 1 H, J=2.2 Hz), 4.14 (t, 2 H), 2.67 (q, 2 H), and 2.21 (s, 3 H). Mass spectr m (MALDI-TOF, α-cyano-4-hydroxycinnamic acid matrix) calcd. for C$_{17}$H$_{19}$ClN$_4$O$_4$S: 411.1 (M+H). Found: 411.1.

EXAMPLE 2

2-[2-[5-Methyl-3-(2-trifluoromethylphenylsulfonyloxy)phenoxy]ethyl-1-methylene]hydrazinecarboximidamide nitrate a) 5-Methyl-3-(2-trifluoromethylphenylsulfonyloxy)phenol Orcinol monohydrate (2.84 g, 20.0 mmol) and 2-trifluoromethylbenzenesulfonyl chloride (4.90 g, 20.0 mmol) were mixed in saturated aqueous NaHCO$_3$ (70 mL) and diethyl ether (70 mL). The biphasic mixture was stirred vigorously at room temperature overnight. The reaction mixture was diluted with water (100 mL) and extracted into ethyl acetate (3×80 mL). The organic phase was washed with brine (2×50 mL) and dried over Na$_2$SO$_4$. After removing the solvent in vacuo, the residue was purified by flash column chromatography (dichloromethane to 2% ethyl acetate in dichloromethane) to give the title compound as a white solid (3.65 g, 55%). $^1$H-NMR (300 MHz, CDCl$_3$) δ 8.12 (d, J=8.0 Hz, 1 H), 7.98 (d, J=7.9 Hz, 1 H), 7.80 (t, J=8.2 Hz, 1 H), 7.69 (t, J=7.8 Hz, 1 H), 6.55 (s, 1 H), 6.48 (s, 1 H), 6.39 (s, 1 H), 5.11 (s, 1 H), 2.23 (s, 3 H).

b) 3-[5-Methyl-3-(2-trifluoromethylphenylsulfonyloxy)phenoxy]propanol

To a solution of 5-methyl-3-(2-trifluoromethylphenylsulfonyloxy)phenol (665 mg, 2.0 mmol), as prepared in the preceding step, tri-n-butylphosphine (607 mg, 3.0 mmol), and 1,3-propanediol (760 mg, 10 mmol) in anhydrous tetrahydrofuran (20 mL) was added 1,1'-(azodicarbonyl)dipiperidine (757 mg, 3.0 mmol). The mixture was stirred at room temperature overnight. Hexane (30 mL) was added to the mixture, and the precipitates were removed by filtration. The filtrate was evaporated in vacuo, and the residue was purified by flash column chromatography (2:1 hexane/ethyl acetate) to give the title compound as a colorless oil (745 mg, 94%). $^1$H-NMR (300 MHz, CDCl$_3$) δ 8.13 (d, J=7.2 Hz, 1 H), 7.99 (d, J=7.2 Hz, 1 H), 7.80 (t, J=7.6 Hz, 1 H), 7.70 (t, J=7.3 Hz, 1 H), 6.63 (s, 1 H), 6.48 (s, 1 H), 6.46 (s, 1 H), 4.02 (t, J=6.0 Hz, 2 H), 3.81 (m, 2 H), 2.25 (s, 3 H), 1.99 (m, 2 H), 1.61 (s, 1 H).

c) 3-[5-Methyl-3-(2-trifluoromethylphenylsulfonyloxy)phenoxy]propionaldehyde

Sulfur trioxide pyridine complex (1.12 mg, 7.0 mmol) was added to a solution of 3-[5-methyl-3-(2-trifluoromethylphenylsulfonyloxy)phenoxy]propanol (700 mg, 1.8 mmol), as prepared in the preceding step, N,N-diisopropylethylamine (0.7 mL, 5.5 mmol) and anhydrous dimethyl sulfoxide (0.4 mL, 5.6 mmol) in anhydrous dichloromethane (20 mL). The reaction mixture was stirred at ambient temperature for 1 hour and then quenched with 10% aqueous citric acid (50 mL). The mixture was extracted into dichloromethane (3×50 mL), then the dichloromethane solution was washed with 10% aqueous citric acid (40 mL) and dried over Na$_2$SO$_4$. After removing the solvent in vacuo, the residue was purified by flash column chromatography (dichloromethane) to give the title compound as a colorless oil (595 mg, 85%). $^1$H-NMR (300 MHz, CDCl$_3$) δ 9.84 (s, 1 H), 8.13 (d, J=7.5 Hz, 1 H), 7.99 (d, J=7.5 Hz, 1 H), 7.80 (t, J=7.6 Hz, 1 H), 7.70 (t, J=7.3 Hz, 1 H), 6.62 (s, 1 H), 6.51 (s, 1 H), 6.45 (s, 1 H), 4.21 (t, J=6.0 Hz, 2 H), 2.87 (t, J=6.0 Hz, 2 H), 2.25 (s, 3 H).

d) 2-[2-[5-Methyl-3-(2-trifluoromethylphenylsulfonyloxy)phenoxy]ethyl-1-methylene]hydrazinecarboximidamide nitrate A solution of 3-[5-methyl-3-(2-trifluoromethylphenylsulfonyloxy)phenoxy]propionaldehyde (583 mg, 1.5 mmol), as prepared in the preceding step, and aminoguanidine nitrate (412 mg, 3.0 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a colorless solid (465 mg, 61%). $^1$H-NMR (300 MHz, DMSO-d$_6$) δ 8.19 (d,J=7.7 Hz, 1 H), 8.11 (d,J=7.8 Hz, 1 H), 8.06 (t,J=7.6 Hz, 1 H), 7.94 (t, J=7.6 Hz, 1 H), 7.74 (br s, 1 H), 7.55 (br s, 4 H), 4.14 (t, J=6.3 Hz, 2 H), 2.68 (t, J=9.0 Hz, 2 H), 2.21 (s, 3 H). Mass spectrum (MALDI-TOF, α-cyano-4-hydroxycinnamic acid matrix) calcd. for C$_{18}$H$_{19}$F$_3$N$_4$O$_4$S: 445.1 (M+H), 467.1 (M+Na). Found: 445.0, 466.8.

EXAMPLE 3

2-[2-[5-Methyl-3-(2-trifluoromethylbenzyloxy)phenoxylethyl-1-methylene]-hydrazinecarboximidamide nitrate a) 5-Methyl-3-(2-trifluoromethylbenzyloxy)phenol Orcinol monohydrate (4.30 g, 30 mmol) in N,N-dimethylformarnide (20 mL) was added to a suspension of sodium hydride (1.5 g, 60 mmol) in N,N-dimethylformamide (30 mL), and the mixture was stirred at ambient temperature for 30 minutes. To the above solution was slowly added 2-trifluoromethylbenzyl chloride (5.0 g,25 mmol) in N,N-dimethylformamide (10 mL). The mixture was stirred at ambient temperature for 3 hours. After carefully quenching with water (100 mL), the mixture was extracted with ethyl acetate (3×100 mL). The ethyl acetate solution was washed with brine (2×100 mL) and dried over Na$_2$SO$_4$. After evaporating the solvent in vacuo, the residue was purified by flash column chromatography (3:1 hexane/ethyl acetate) to give the title compound as a white solid (2.9 g, 41%). $^1$H-NMR (300 MHz, CDCl$_3$) δ 7.72 (d, J=7.8 Hz, 1 H), 7.68 (d, J=7.9Hz, 1 H), 7.56 (t, J=7.7 Hz, 1 H), 7.41 (t, J=7.7 Hz, 1 H), 6.39 (s, 1 H), 6.28 (s, 2 H), 5.22 (s, 2 H), 4.79 (s, 1 H), 2.27 (s, 3 H).

b) 3-[5-Methyl-3-(2-trifluoromethylbenzyloxy)phenoxy]propanol

To a solution of 5-methyl-3-(2-trifluoromethylbenzyloxy)phenol (1.41 g, 5.0 mmol), as prepared in the preceding step, tri-n-butylphosphine (1.62 g, 8.0 mmol) and 1,3-propanediol (1.90 g, 25 rnmol) in anhydrous tetrahydrofuran (50 mL) was added 1,1'-(azodicarbonyl) dipiperidine (2.01 g, 8.0 mmol). The mixture was stirred at ambient temperature overnight. Hexane (100 mL) was added to the mixture and the precipitates were removed by filtration. The filtrate was evaporated in vacuo, and the residue was purified by flash column chromatography (2:1 hexane/ethyl acetate) to give the title compound as a colorless oil (1.50 g, 84%). $^1$H-NMR (300 MHz, CDCl$_3$) δ 7.74 (d, J=7.8 Hz, 1 H), 7.69 (d, J=7.8 Hz, 1 H), 7.56 (t, J=7.6 Hz, 1 H), 7.41 (t, J=7.7 Hz, 1 H), 6.41 (s, 1 H), 6.37 (s, 2 H), 5.23 (s, 2 H), 4.08 (t, J=6.0 Hz, 2 H), 3.85 (t, J=6.0 Hz, 2 H), 2.29 (s, 3 H), 2.02 (t, J =6.0 Hz, 2 H), 1.76 (s, 1 H).

c) 3-[5-Methyl-3-(2-trifluoromethylbenzyloxy)phenoxy]propionaldehyde

Sulfur trioxide pyridine complex (1.3 g, 8.0 mmol) was added to a solution of 3-[5-methyl-3-(2-trifluoromethylbenzyloxy)phenoxy]propanol (680 mg, 2.0 mmol), as prepared in the preceding step, N,N-diisopropylethylamine (0.7 mL, 5.5 mmol) and anhydrous dimethyl sulfoxide (0.4 mL, 5.6 mmol) in anhydrous dichloromethane (20 mL). The reaction mixture was stirred at ambient temperature for 1 hour and then quenched with 10% aqueous citric acid (50 mL). The mixture was extracted into dichloromethane (3×50 mL), and the dichloromethane solution was washed with 10% aqueous citric acid (40 mL) and dried over Na$_2$SO$_4$. After removing the solvent in vacuo, the residue was purified by flash column chromatography (dichloromethane) to give the title compound as a white solid (575 mg, 85%). $^1$H-NMR (300 MHz, CDCl$_3$) δ 9.85 (s, 1 H), 7.75 (d, J=7.8 Hz, 1 H), 7.69 (d, J=7.8 Hz, 1 H), 7.56 (t, J=7.6 Hz, 1 H), 7.41 (t, J=7.6 Hz, 1 H), 6.42 (s, 1H), 6.37 (s, 1 H), 6.35 (s, 1 H), 5.23 (s, 2 H), 4.27 (t, J=6.1 Hz, 2 H), 2.87 (t, J=6.1 Hz, 2 H), 2.29 (s, 3 H).

d) 2-[2-[5-Methyl-3-(2-trifluoromethylbenzyloxy)phenoxylethyl-1-methylene]hydrazinecarboximidamide nitrate A solution of 3-[5-methyl-3-(2-trifluoromethylbenzyloxy)phenoxy]propionaldehyde (305 mg, 0.9 mmol), as prepared in the preceding step, and aminoguanidine nitrate (274 mg, 2.0 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (315 mg, 77%). $^1$H-NMR (300 MHz, DMSO-d$_6$) δ 7.80 (d, J=7.9 Hz, 1 H), 7.74 (m, 2 H), 7.55–7.62 (m, 6 H), 6.44 (s, 1 H), 6.41 (s, 1 H), 6.39 (s, 1 H), 5.18 (s, 2 H), 4.18 (t, J=6.3 Hz, 2 H), 2.69 (t, J=6.3 Hz, 2 H), 2.24 (s, 3 H). Mass spectrum (MALDI-TOF, α-cyano-4-hydroxycinnamic acid matrix) calcd. for C$_{19}$H$_{21}$F$_3$N$_4$O$_2$: 395.2 (M+H), 417.1 (M+Na), 433.1 (M+K). Found: 395.3, 417.0, 433.2.

EXAMPLE 4

2-[3-[3-(2-Chlorophenylsulfonyloxy)-5-methoxyphenyllpropyl-1-methylene] hydrazinecarboximidamide hydrochloride a) 3-Hydroxy-5-methoxybenzaldehyde Diethyl azodicarboxylate (1.5 mL, 9.53 mmol) was added to a solution of 1.14 g (8.26 mmol) of 3,5-dihydroxybenzaldehyde, 2.39 g (9.12 mmol) of triphenylphosphine, and 380 μL (9.4 mmol) of methanol in anhydrous tetrahydrofuran (20 mL) at 0° C. The reaction mixture was stirred at ambient temperature for 30 min and quenched with 10% aqueous citric acid. The reaction mixture was extracted into diethyl ether, dried (MgSO$_4$), and purified by flash chromatography (dichloromethane/petroleum ether (2:1 then 100:0)) to give the title compound (309 mg, 25%) as a gum. $^1$H-NMR (300 MHz, CDCl$_3$) δ 9.82 (s, 1 H), 6.98–6.99 (m, 2 H), 6.94–6.96 (m, 1 H), 3.80 (s, 3 H).

b) 2-[(1,3-Dioxan-2-yl)ethyl](triphenyl)phosphonium bromide

A solution of 1.43 g (7.33 mmol) of 2-(2-bromoethyl)-1,3-dioxane and 1.92 g (7.32 mmol) of triphenylphosphine in 20 mL of acetonitrile was refluxed for 2 days. The title compound (2.52 g, 75% yield) was isolated directly from the reaction mixture by trituration from diethyl ether/dichloromethane and was used directly in the next reaction. $^1$H-NMR (300 MHz, CDCl$_3$) δ 7.66–7.87 (m, 15 H),5.10 (t, 1 H, J=5Hz), 3.99–4.04 (m, 2 H), 3.80–3.89 (m, 4 H), 1.85–2.10 (m,3 H), 1.32–1.37 (m, 1 H).

c) 2-[3-(3-Hydroxy-5-methoxyphenyl)-3-propenyl-1,3-dioxane

To a solution of 2.42 g (5.30 mmol) 2-[(1,3-dioxan-2-yl)ethyl](triphenyl)phosphonium bromide, as prepared in step b, in anhydrous tetrahydrofuran (10 mL) at −78° C. was added 2.4 mL (3.6 mmol) of 1.5M lithium diisopropylamide in cyclohexane. The reaction mixture was stirred at −78° C. for 10 min, then 308 mg (2.03 mmol) of 3-hydroxy-5-methoxybenzaldehyde, as prepared in step a, in 3 mL of anhydrous tetrahydrofuran was added. The reaction mixture was stirred at ambient temperature for 1 h. The reaction mixture was quenched with 10% aqueous citric acid, extracted into diethyl ether, dried (MgSO$_4$), and purified by flash chromatography (diethyl ether/petroleum ether (1:2 to 1:1)) to provide 143 mg (28% yield) of the title compound (mixture of cis and trans isomers) as an oil.

d) 2-[3-(3-Hydroxy-5-methoxyphenyl)propyl]-1,3-dioxane

A mixture of 2-[3-(3-hydroxy-5-methoxyphenyl)-3-propenyl]-1,3-dioxane (143 mg, 0.572 mmol), as prepared in the preceding step, and 66 mg of 10% palladium on carbon in tetrahydrofuran (2 mL) was hydrogenated at atmospheric pressure and ambient temperature for 1 h. The reaction mixture was filtered through Celite and concentrated to give crude title compound which was used directly in the next reaction. $^1$H-NMR (300 MHz, CDCl$_3$) δ 6.31 (br s, 1 H), 6.22–6.28 (m, 2 H), 4.52 (t, 1 H, J=5Hz), 4.07–4.12 (m, 2 H), 3.75 (s, 3 H), 3.70–3.79 (m, 2 H), 2.53 (t, 2 H, J=5 Hz), 1.1–2.2 (m, 6 H).

e) 2-[3-[3-(2-Chlorophenylsulfonyloxy)-5-methoxyphenyl]propyl]-1,3-dioxane

To all of 2-[3-(3-hydroxy-5-methoxyphenyl)propyl]-1,3-dioxane, as prepared in step d, in dichloromethane (2 mL) containing 500 μL of N,N-diisopropylethylamine was added 166 mg (0.79 mmol) of 2-chlorobenzenesulfonyl chloride. After stirring at ambient temperature for 30 min, 5 mg of N,N-dimethylaminopyridine was added and the reaction mixture was stirred for an additional 30 min. The reaction mixture was quenched with 10% aqueous citric acid, extracted into diethyl ether, dried (MgSO$_4$), concentrated, and purified by flash chromatography (dichloromethane/diethyl ether (100:0 to 95:5)) to give 180 mg (77% yield from 2-[3-(3-hydroxy-5-methoxyphenyl)-3-propenyl]-1,3-dioxane) of the title compound. $^1$H-NMR (300 MHz, CDCl$_3$) δ 7.84 (dd, 1 H, J 1.5, 8 Hz), 7.53–7.63 (m, 2 H), 7.33–7.39 (m, 1 H), 6.59 (t, 1 H, J =2 Hz), 6.50 (m, 2 H), 4.48 (t, 1 H, J=5 Hz), 4.06–4.11 (m, 2 H), 3.70 (s,3 H), 3.71-3.79(m,2 H), 2.49 (t, 2 H, J=5 Hz), 1.98–2.14 (m, 1 H), 1.25–1.6 (m, 5 H). Mass spectrum (MALDI-TOF, gentisic acid matrix) calcd. for C$_{20}$H$_{23}$ClO$_6$S: 449.1 (M+Na). Found: 449.1.

f) 4-[3-(2-Chlorophenylsulfonyloxy)-5-methoxyphenyl]butanal

A solution of 156 mg (0.38 mmol) 2-[3-[3-(2-chlorophenylsulfonyloxy)-5-methoxyphenyl]propyl]-1,3-dioxane, as prepared in the preceding step, in 2 mL of tetrahydrofuran was treated with 4.5 μL of 10% aqueous hydrochloric acid. The reaction mixture was stirred at 60° C. for 1 h. The reaction mixture was diluted with water, extracted into dichloromethane, dried (MgSO$_4$), and purified by flash chromatography (dichloromethane) to give 23.4 mg of the title compound as the minor product of the reaction. $^1$H-NMR (300 MHz, CDCl$_3$) δ 9.70 (t, 1 H, J=2 Hz), 7.93 (dd, 1 H, J=1.5,8Hz), 7.52–7.9 (m, 2 H), 6.57 (t, 1 H), 6.52 (t, 1 H, J=2 Hz), 6.49 (t, 1 H, J=2 Hz), 3.69 (s, 3 H), 2.52 (t, 2 H, J=7 Hz), 2.33 (dt, 2 H, J=1.5, 7 Hz), 1.80 (pentet, 2 H, J=7 Hz).

g) 2-[3-[3-(2-Chlorophenylsulfonyloxy)-5-methoxyphenyl]propyl-1-methylene]hydrazinecarboximidamide hydrochloride A solution of 23 mg (0.068 mmol) of 4-[3-(2-chlorophenylsulfonyloxy)-5-methoxyphenyl]butanal, as prepared in the preceding step, and 40 mg (0.29 mmol) of aminoguanidine nitrate in 1 mL of methanol was stirred overnight. The reaction mixture was quenched with 150 μL of 2N sodium hydroxide, diluted with water, and extracted into dichloromethane. The organic phase was washed with water, dried (K$_2$CO$_3$), and concentrated to give 24.6 mg of the free base of the title compound. The crude product was diluted with 1 mL of dichloromethane, treated with 140 μL of 1N HCl in methanol, and triturated from diethyl ether/hexane to give the title compound. $^1$H-NMR (300 MHz, DMSO-d$_6$) δ 11.25 (br s, 1 H), 7.78–7.94 (m, 3 H), 7.53–7.59 (m, 1 H), 7.45 (t, 1 H), 6.76 (m, 1 H), 6.48 (t, 1 H), 6.45 (t, 2 H), 3.67 (s, 3 H), 2.13 (q, 2 H), 1.66 (pentet, 2 H). Mass spectrum (MALDI-TOF, α-cyano-4-hydroxycinnamic acid matrix) calcd. for C$_{18}$H$_{21}$ClN$_4$O$_4$S: 425.1 (M+H). Found: 425.1.

EXAMPLE 5

2-[2-[(5-Methyl-3-(N-(5-ethoxycarbonylpentyl)-N-(2-trifluoromethylphenylsulfonyl))amino)phenoxyethyl-1-methylene]hydrazinecarboximidamidenitrate a) 3-Benzyloxy-5-methylphenol

Orcinol monohydrate (7.10 g, 50 mmol) in N,N-dimethylformamide (20 mL) was added dropwise to NaH (2.4 g, 100 mmol) in N,N-dimethylformamide (60 mL). The reaction mixture was stirred at room temperature for 20 min. Benzyl bromide (8.55 g, 50 mmol) in N,N-dimethylformamide (20 mL) was then added, and the reaction mixture was stirred at ambient temperature for 2 hours. Water (100 mL) was added carefully followed by extraction by ethyl acetate (3×100 mL). The organic phase was washed with brine (2×50 mL), dried over Na$_2$SO$_4$, and concentrated in vacuo. The residue was purified by flash column chromatography (3:1 hexane/ethyl acetate) to give the title compound as a yellow oil (3.40 g, 32%). $^1$H-NMR (300 MHz, CDCl$_3$) δ 7.39 (m, 5 H), 6.40 (s, 1 H), 6.29 (s, 1 H), 6.26 (s, 1 H), 5.00 (s, 2 H), 4.89 (s, 1 H), 2.26 (s, 3 H).

b) 2-Bromo-2-methylpropanamide

To a vigorously stirred solution of 2-bromo-2-methylpropanoyl bromide (11 mL) in light petroleum ether (250 mL) at 0 ° C. was added in portions aqueous ammonia (50 mL). Stirring was continued for a further 30 min, and the resulting precipitate was collected and washed with water (2×50 mL) to give the title compound as a white solid (14.1 g, 96%) which was directly used in the next step without purification.

c) 2-(3-Benzyloxy-5-methyl)phenoxy-2-methylpropanamide

3-Benzyloxy-5-methylphenol (2.14 g, 10 mmol), as prepared in step a, was stirred in anhydrous 1,4-dioxane (50 mL) with sodium hydride (265 mg, 11 mmol) for 1 h. 2-Bromo-2-methylpropanamide (1.66 g, 10 mmol), as prepared in step b of this example, was added and the reaction mixture was heated to 80° C. for 6 h. After cooling, the precipitated sodium bromide was filtered off, and the filtrate was evaporated in vacuo. The residue was purified by flash column chromatography (7% ethyl acetate in dichloromethane) to give the title compound as a pale yellow solid (2.50 g, 83%). $^1$H-NMR (300 MHz, CDCl$_3$) δ 7.40 (m, 5 H), 6.61 (br s, 1 H), 6.54 (s, 1 H), 6.38 (s, 2 H), 5.69 (br s, 1 H), 5.29 (s, 2 H), 2.28 (s, 3 H), 1.97 (s, 3 H), 1.52 (s, 3 H).

d) N-(3-Benzyloxy-5-methylphenyl)-2-hydroxy-2-methylpropanamide

To a solution of 2-(3-benzyloxy-5-methyl)phenoxy-2-methylpropanamide (1.50 g, 5.0 mmol), as prepared in the preceding step, in 1,3-dimethyl-3,4,5,6-tetrahydro-2(1H)-pyrimidinone (DMPU) (2 mL) and N,N-dimethylformamide (18 mL) was added sodium hydride (360 mg, 15 mmol), the mixture was heated to 100 ° C. for 3 h. The solution was poured into water (200 mL) and extracted with ethyl acetate (3×100 mL). The organic phase was washed with water (3×100 mL), dried over Na$_2$SO$_4$, and concentrated in vacuo. The residue was purified by flash column chromatography (5% ethyl acetate in dichloromethane) to give the title compound as a white solid (870 mg, 58%). $^1$H-NMR (300 MHz, CDCl$_3$) δ 8.61 (s, 1 H), 7.42 (m, 5 H), 7.28 (s, 1 H), 6.93 (s, 1 H), 6.59 (s, 1 H), 5.05 (s, 2 H), 2.30 (s, 3 H), 2.18 (s, 1 H), 1.58 (s, 3 H), 1.56 (s,3 H).

e) 3-Benzyloxy-5-methylaniline

N-(3-Benzyloxy-5-methylphenyl)-2-hydroxy-2-methylpropanamide (600 mg, 2.0 mmol), as prepared in the preceding step, was mixed with 10N NaOH (25 mL) and ethanol (10 mL), and the mixture was refluxed for 2 days. After cooling to ambient temperature, the mixture was diluted with water (60 mL) and extracted with dichloromethane (3×60 mL). The dichloromethane solution was washed with brine (2×50 mL) and dried over $Na_2SO_4$. After evaporating the solvent in vacuo, the residue was purified by flash column chromatography (dichloromethane) to give the title compound as a yellow oil (265 mg, 61%). $^1$H-NMR (300 MHz, CDCl$_3$) δ 7.37 (m, 5 H), 6.24 (s, 1 H), 6.14 (s, 2 H), 5.00 (s, 2 H), 3.59 (br s, 2 H), 2.23 (s, 3 H).

f) 3-Benzyloxy-5-methyl-1-(2-trifluoromethylphenylsulfonylamino)benzene

2-Trifluoromethylbenzenesulfonyl chloride (490 mg, 2.0 mmol) was added to a solution of 3-benzyloxy-5-methylaniline (426 mg, 2.0 mmol), as prepared in the preceding step, and N-methylmorpholine (0.5 mL) in dichloromethane (10 mL). The mixture was stirred at ambient temperature overnight. After adding additional dichloromethane (100 mL), the dichloromethane solution was washed with saturated aqueous NaHCO$_3$ (2×50 mL), 10% HCl (2×50 mL), and brine (2×50 mL), and dried over Na$_2$SO$_4$. After evaporating the solvent in vacuo, the residue was purified by flash column chromatography (4:1 dichloromethane/hexane) to give the title compound as white solid (700 mg, 83%). $^1$H-NMR (300 MHz, CDCl$_3$) δ 7.93 (d, J=7.8 Hz, 1 H), 7.85 (d, J=7.3 Hz, 1 H), 7.63 (t, J=7.7 Hz, 1 H), 7.53 (t,J=7.7 Hz, 1 H), 7.38 (m, 5 H), 6.60 (s, 1 H), 6.55 (s, 2 H), 6.40 (s, 1 H), 4.98 (s, 2 H), 2.20 (s, 3 H).

g) Ethyl 6-[3-benzyloxy-5-methylphenyl-(2-trifluoromethylphenyl)sulfonylamino]hexanoate 3-Benzyloxy-5-methyl-1-(2-trifluoromethylphenylsulfonylamino)benzene (550 mg, 1.3 mmol), as prepared in the preceding step, ethyl 6-bromohexanoate (290 mg, 1.3 mmol), and K$_2$CO$_3$ (1.0 g) were mixed in N,N-dimethylformamide (10 mL). The mixture was heated to 60° C. and stirred for 12 h. The solid was removed by filtration, and the filtrate was evaporated under high vacuum. The residue was dissolved in ethyl acetate (100 mL), washed with saturated aqueous NaHCO$_3$ (2×50 mL) and brine (2×50 mL), and dried over Na$_2$SO$_4$. The solvent was evaporated in vacuo to give the title compound as a pale red oil (735 mg, 100%) which was directly used for the next step. $^1$H-NMR (300 MHz, CDCl$_3$) δ 7.85 (d, J=7.7 Hz, 1 H), 7.71 (d, J=7.8 Hz, 1 H), 7.60 (t, J=7.7 Hz, 1 H), 7.47 (t, J=7.7 Hz, 1 H), 7.37 (m, 5 H), 6.71 (s, 1 H), 6.53 (s, 1 H), 6.51 (s, 1 H), 4.95 (s,2H), 4.11 (q, J=7.1 Hz, 2 H),3.66(t,J=7.0 Hz, 2 H), 2.25 (t, J=7.4 Hz, 2 H), 2.23 (s, 3 H), 1.33–1.62 (m, 6 H), 1.24 (t, J=7.1 Hz, 3 H).

h) [5-Methyl-3-(N-(5-ethoxycarbonylpentyl)-N-(2-trifluoromethylphenylsulfonyl))aminolphenol Ethyl 6-[3-benzyloxy-5-methylphenyl-(2-trifluoromethylphenyl)sulfonylamino]hexanoate (735 mg, 1.3 mmol), as prepared in the preceding step, was mixed with palladium on carbon (10%, 100 mg) in ethanol (20 mL). The mixture was stirred under hydrogen (balloon) for 2h. The catalyst was removed by filtration through Celite, and the filtrate was evaporated in vacuo to give the title compound as a pale red oil (585 mg, 95%) which was directly used for the next step. $^1$H-NMR (300 MHz, CDCl$_3$) δ 7.86 (d, J=7.4 Hz, 1 H), 7.76 (d, J=7.9 Hz, 1 H), 7.62 (t, J=7.5 Hz, 1 H), 7.51 (t, J=7.8 Hz, 1 H), 6.57 (s, 1 H), 6.47 (s, 1 H), 6.43 (s, 1 H), 5.35 (s, 1 H), 4.12 (q, J=7.1 Hz, 2 H), 3.67 (t, J=6.9 Hz, 2 H), 2.27 (t, J=7.3 Hz, 2 H), 2.20 (s, 3 H), 1.36–1.67 (m, 6 H), 1.25 (t, J=7.1 Hz, 3 H).

i) 3-[(5-Methyl-3-(N-(5-ethoxycarbonylpentyl)-N-(2-trifluoromethylphenylsulfonyl))amino)phenoxy]propanol To a solution of [5-methyl-3-(N-(5-ethoxycarbonylpentyl)-N-(2-trifluoromethylphenylsulfonyl))amino]phenol (520 mg, 1.1 mmol), as prepared in the preceding step, tri-n-butylphosphine (304 mg, 1.5 mmol) and 1,3-propanediol (760 mg, 10 mmol) in anhydrous tetrahydrofuran (10 mL) was added 1,1'-(azodicarbonyl)dipiperidine (380 mg, 1.5 mmol). The mixture was stirred at ambient temperature overnight. Hexane (30 mL) was added to the mixture and the precipitates were removed by filtration. The filtrate was evaporated in vacuo, and the residue was purified by flash column chromatography (4:1 dichloromethane/ethyl acetate) to give the title compound as a colorless oil (505 mg, 86%). $^1$H-NMR (300 MHz, CDCl$_3$) δ 7.86 (d, J=7.5 Hz, 1 H), 7.76 (d, J=7.8 Hz, 1 H), 7.62 (t, J=7.6 Hz, 1 H), 7.51 (t, J=7.6 Hz, 1 H), 6.64 (s, 1 H), 6.49 (s, 1 H), 6.47 (s, 1 H), 4.11 (q, J=7.1 Hz, 2 H), 4.01 (t, J=6.0 Hz,2 H), 3.83 (t,J=5.9 Hz, 2 H), 3.67 (t,J=7.0Hz, 2 H), 2.26(t, J=7.4 Hz, 2 H), 2.20 (s, 3 H), 1.99 (t, J=6.0 Hz, 2 H), 1.73 (br s, 1 H), 1.32–1.63 (m, 6H), 1.24(t,J=7.1 Hz,3 H).

j) 3-[(5-Methyl-3-(N-(5-ethoxycarbonylpentyl)-N-(2-trifluoromethylphenylsulfonyl))amino)phenoxy] propionaldehyde Sulfur trioxide pyridine complex (480 mg, 3.0 mmol) was added to a solution of 3-[(5-methyl-3-(N-(5-ethoxycarbonylpentyl)-N-(2-trifluoromethylphenylsulfonyl))amino)phenoxy]propanol (480 mg, 0.9 mmol), as prepared in the preceding step, N,N-diisopropylethylamine (0.4 mL, 3.2 mmol) and anhydrous dimethyl sulfoxide (0.2 mL, 2.8 mmol) in dichloromethane (10 mL). The reaction mixture was stirred at ambient temperature for 1 hour and then quenched with 10% aqueous citric acid (40 mL). The mixture was extracted into dichloromethane (3×40 mL), and the dichloromethane solution was washed with 10% aqueous citric acid (30 mL) and dried over Na$_2$SO$_4$. After removing the solvent in vacuo, the residue was purified by flash column chromatography (dichloromethane) to give the title compound as a colorless oil (390 mg, 82%). $^1$H-NMR (300 MHz, CDCl$_3$) δ 9.84 (s, 1 H), 7.86 (d, J=7.5 Hz, 1 H), 7.75 (d, J=7.9 Hz, 1 H), 7.63 (t, J=7.5 Hz, 1 H), 7.52 (t, J=7.7 Hz, 1 H), 6.63 (s, 1 H), 6.50 (s, 1 H), 6.48 (s, 1 H), 4.20 (t, J=6.1 Hz, 2 H), 4.11 (q, J=7.1 Hz, 2 H), 3.67 (t, J=7.0 Hz, 2 H), 2.87 (t, J=6.0 Hz, 2 H), 2.26 (t, J=7.3 Hz, 2 H), 2.23 (s, 3 H), 1.32–1.63 (m, 6 H), 1.24 (t, J=7.1 Hz, 3 H).

k) 2-[2-[(5-Methyl-3-(N-(S-eth oxycarbonylpentyl)-N-(2-trifluoromethylphenylsulfonyl)amino)phenoxy]ethyl-1-methylene]hydrazinecarboximidamide nitrate A mixture of 3-[(5-methyl-3-(N-(5-ethoxycarbonylpentyl)-N-(2-trifluoromethylphenylsulfonyl))amino)phenoxy] propionaldehyde (370 mg, 0.7 mmol), as prepared in the preceding step, and aminoguanidine nitrate (275 mg, 2.0 mmol) in ethanol (10 mL) was stirred at ambient temperature overnight. The mixture was quenched with water (50 mL) and extracted with dichloromethane (3×50 mL). The dichloromethane solution was washed with brine (2×50 mL) and dried over Na$_2$SO$_4$. After evaporating the solvent in vacuo, the residue was purified by flash column chromatography (10% methanol in dichloromethane) to give the title compound as a colorless foam (350 mg, 77%). $^1$H-NMR (300 MHz, DMSO-d$_6$) δ 11.52 (br s, 1 H), 7.99 (d, J=7.5 Hz, 1 H), 7.84 (m, 3 H), 7.56 (m, 5 H), 6.77 (s, 1 H), 6.60 (s, 1

H), 6.56 (s, 1 H), 4.13 (t, J=6.3 Hz, 2 H), 4.03 (q, J=7.1 Hz, 2 H), 3.67 (t, J=6.4 Hz, 2 H), 2.68 (m, 2 H), 2.23 (t, J=7.2 Hz, 2 H), 2.22 (s, 3 H), 1.25–1.51 (m, 6H), 1.16 (t, J=7.1 Hz, 3 H). Mass spectrum (MALDI-TOF, α-cyano-4-hydroxycinnamic acid matrix) calcd. for $C_{26}H_{34}F_3N_5O_5S$: 586.2 (M+H), 608.2 (M+Na). Found: 586.3, 608.4.

EXAMPLE 6

2-[2-[3-(2,3-Dichlorophenylsulfonyloxy)-5-methylphenoxy]ethyl-1-methylene]hydrazinecarboximidamide nitrate a) 3-(2,3-Dichlorophenylsulfonyloxy)-5-methylphenol Orcinol monohydrate (1.42 g, 10.0 mmol) and 2,3-dichlorobenzenesulfonyl chloride (2.46 g, 10.0 mmol) were mixed in saturated aqueous $NaHCO_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over $Na_2SO_4$. After removing the solvent in vacuo, the residue was purified by flash column chromatography (dichloromethane to 2% ethyl acetate in dichloromethane) to give the title compound as a pale yellow solid (1.45 g, 45%). $^1$H-NMR (300 MHz, $CDCl_3$) δ 7.91 (d, J=8.0 Hz, 1 H), 7.75 (d, J=8.0 Hz, 1 H), 7.33 (t, J=8.0 Hz, 1 H), 6.55 (s, 2 H), 6.44 (s, 1 H), 5.27 (s, 1 H), 2.24 (s, 3 H).

b) 3-[3-(2,3-Dichlorophenylsulfonyloxy)-5-methylphenoxy]propanol

To a solution of 3-(2,3-dichlorophenylsulfonyloxy)-5-methylphenol (642 mg, 2.0 mnol), as prepared in the preceding step, tri-n-butylphosphine (607 mg, 3.0 mmol) and 1,3-propanediol (760 mg, 10 mmol) in anhydrous tetrahydrofuran (20 mL) was added 1,1'-(azodicarbonyl) dipiperidine (757 mg, 3.0 mmol). The mixture was stirred at ambient temperature overnight. Hexane (30 mL) was added to the mixture and the precipitates were removed by filtration. The filtrate was evaporated in vacuo, and the residue was purified by flash column chromatography (2:1 hexane/ethyl acetate) to give the title compound as a colorless oil (690 mg, 88%). $^1$H-NMR (300 MHz, $CDCl_3$) δ 7.92 (d, J=8.0 Hz, 1 H), 7.76 (d, J=8.1 Hz, 1 H), 7.34 (t, J=8.0 Hz, 1 H), 6.62 (s, 1 H), 6.55 (s, 1 H), 6.50(s, 1 H), 4.02(t,J=6.0Hz, 2H), 3.82(t,J=5.7Hz,2H), 2.26(s,3 H), 1.99 (m, 2 H), 1.58 (s, 1 H).

c) 3-[3-(2,3-Dichlorophenylsulfonyloxy)-5-methylphenoxy]propionaldehyde

Sulfur trioxide pyridine complex (720 mg, 4.5 mmol) was added to a solution of 3-[3-(2,3-dichlorophenylsulfonyloxy)-5-methylphenoxy]propanol (580 mg, 1.5 mmol), as prepared in the preceding step, N,N-diisopropylethylamine (0.7 mL, 5.5 mmol) and anhydrous dimethyl sulfoxide (0.3 mL, 4.2 mmol) in dichloromethane (15 mL). The reaction mixture was stirred at ambient temperature for 1 hour and then quenched with 10% aqueous citric acid (50 mL). The mixture was extracted into dichloromethane (3×50 mL), and the dichloromethane solution was washed with 10% aqueous citric acid (40 mL) and dried over $Na_2SO_4$. After removing the solvent in vacuo, the residue was purified by flash column chromatography (dichloromethane) to give the title compound as a colorless oil (545 mg, 93%). $^1$H-NMR (300 MHz, $CDCl_3$) δ 9.84 (s, 1 H), 7.92 (d, J=8.0 Hz, 1 H), 7.76 (d, J=8.0 Hz, 1 H), 7.34(t, J=8.0 Hz, 1 H), 6.61 (s, 1 H), 6.57 (s, 1 H), 6.50 (s, 1 H), 4.21 (t, J=6.0 Hz, 2 H), 2.87 (t, J=6.0 Hz, 2 H), 2.26 (s, 3 H).

d) 2-[2-[3-(2,3-Dichlorophenylsulfonyloxy)-5-methylphenoxyethyl-1-methylene]hydrazinecarboximidamide nitrate A solution of 3-[3-(2,3-dichlorophenylsulfonyloxy)-5-methylphenoxy]propionaldehyde (470 mg, 1.2 mmol), as prepared in the preceding step, and aminoguanidine nitrate (343 mg, 2.5 mrnol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (535 mg, 88%). $^1$H-NMR (300 MHz, DMSO-$d_6$) δ 8.12 (d, J=8.1 Hz, 1 H), 7.96 (d, J=8.0 Hz, 1 H), 7.61 (t, J =8.0 Hz, 1 H), 7.54 (brs, 1 H), 7.52 (brs, 4 H), 4.16 (t, J=6.3 Hz, 2 H), 2.68 (dd, J=11.3,6.2Hz, 2 H), 2.22 (s, 3 H). Mass spectrum (MALDI-TOF, α-cyano-4- hydroxycinnamic acid matrix) calcd. for $C_{17}H_{18}Cl_2N_4O_4S$: 445.1 (M+H), 467.0 (M+Na). Found: 444.9, 466.9.

EXAMPLE 7

2-[2-[3-(2,5-Dichlorophenylsulfonyloxy)-5-methylphenoxy]ethyl-1-methylene]hydrazinecarboximidamide nitrate a) 3-(2,5-Dichlorophenylsulfonyloxy)-5-methylphenol Orcinol monohydrate (1.42 g, 10.0 mmol) and 2,5-dichlorobenzenesulfonyl chloride (2.46 g, 10.0 mmol) were mixed in saturated aqueous $NaHCO_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over $Na_2SO_4$. After removing the solvent in vacuo, the residue was purified by flash column chromatography (dichloromethane to 2% ethyl acetate in dichloromethane) to give the title compound as apale yellow solid (1.65 g, 51%). $^1$H-NMR (300 MHz, $CDCl_3$) δ 7.95 (s, 1H), 7.55 (s, 2H), 6.56 (s, 2H), 6.46 (s, 1H), 5.29 (s, 1H), 2.25 (s, 3H).

b) 3-[3-(2,5-Dichlorophenylsulfonyloxy)-5-methylphenoxy]propanol

To a solution of 3-(2,5-dichlorophenylsulfonyloxy)-5-methylphenol (642 mg, 2.0 mmol), as prepared in the preceding step, tri-n-butylphosphine (607 mg, 3.0 mmol) and 1,3-propanediol (760 mg, 10 mmol) in anhydrous tetrahydrofuran (20 mL) was added 1,1'-(azodicarbonyl) dipiperidine (757 mg, 3.0 mmol). The mixture was stirred at ambient temperature overnight. Hexane (30 mL) was added to the mixture, and the precipitates were removed by filtration. The filtrate was evaporated in vacuo, and the residue was purified by flash column chromatography (2:1 hexane/ethyl acetate) to give the title compound as a colorless oil (700 mg, 90%). $^1$H-NMR (300 MHz, $CDCl_3$) δ 7.96 (s, 1H), 7.56 (s, 2H), 6.63 (s, 1H), 6.55 (s, 1H), 6.51 (s, 1H), 4.03 (t, J=6.0 Hz, 2H), 3.82 (m, 2H), 2.26 (s, 3H), 2.00 (m, 2H), 1.58 (s, 1H).

c) 3-[3-(2,5-Dichlorophenylsulfonyloxy)-5-methylphenoxy]propionaldehyde

Sulfur trioxide pyridine complex (720 mg, 4.5 mmol) was added to a solution of 3-[3-(2,5-dichlorophenylsulfonyloxy)-5-methylphenoxy]propanol (580 mg, 1.5 mmol), as prepared in the preceding step, N,N-diisopropylethylamine (0.7 mL, 5.5 mmol) and anhydrous dimethyl sulfoxide (0.3 mL, 4.2 mmol) in anhydrous dichloromethane (15 mL). The reaction mixture was stirred at ambient temperature for 1 hour and then quenched with 10% aqueous citric acid (50 mL). The mixture was extracted into dichloromethane (3×50 mL), and the dichloromethane solution was washed with 10% aqueous citric acid (40 mL) and dried over $Na_2SO_4$. After removing the solvent in vacuo, the residue was purified by flash column chromatography (dichloromethane) to give the title compound as a colorless oil (530 mg, 91%). $^1$H-NMR (300 MHz, CDCl$_3$) δ 9.84 (s, 1H), 7.96 (s, 1H), 7.56 (s, 2H), 6.63 (s, 1 H), 6.58 (s, 1H), 6.50 (s, 1 H), 4.22 (t, J=6.0 Hz, 2H), 2.88 (t, J=6.1 Hz, 2 H), 2.27 (s, 3H).

d) 2-[2-[3-(2,5-Dichlorophenylsulfonyloxy)-5-methylphenoxy]ethyl-1-methylene]hydrazinecarboximidamide nitrate A mixture of 3-[3-(2,5-dichlorophenylsulfonyloxy)-5-methylphenoxy]propionaldehyde (470 mg, 1.2 mmol), as prepared in the preceding step, and aminoguanidine nitrate (343 mg, 2.5 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (549 mg, 90%). $^1$H-NMR (300 MHz, DMSO-d$_6$) δ 11.4 (br s, 1H), 7.93 (s, 3H), 7.54 (br s, 1H), 7.45 (br s, 4H), 4.17 (t, J=6.2 Hz, 2H), 2.68 (dd, J=11.3, 6.1 Hz, 2H), 2.23 (s, 3H). Mass spectrum (MALDI-TOF, α-cyano-4-hydroxycinnamic acid matrix) calcd. for $C_{17}H_{18}Cl_2N_4O_4S$: 445.1 (M+H), 467.0 (M+Na). Found: 444.8, 466.7.

EXAMPLE 8

2-[2-[3-(2-Methoxyphenylsulfonyloxy)-5-methylphenoxy]ethyl-1-methylene]hydrazinecarboximidamide acetate a) 3-(5-Chloro-2-methoxyphenylsulfonyloxy)-5-methylphenol Saturated aqueous NaHCO$_3$ (70 mL) was added to a solution of 5-chloro-2-methoxybenzenesulfonyl chloride (3.83 g, 15.9 mmol) and orcinol monohydrate (3.39 g, 23.9 mmol) in di-n-butyl ether (53 mL) and tetrahydrofuran (17 mL). The biphasic solution was mixed vigorously at 50° C. for 7 h and then at ambient temperature overnight. The reaction mixture was combined with that from a previous reaction (which used 4.53 g [18.8 mmol] of 5-chloro-2-methoxybenzenesulfonyl chloride), the layers were separated, and the aqueous layer was extracted with ethyl acetate (2×100 mL). The combined organic extracts were washed with brine (250 mL), dried over Na$_2$SO$_4$, filtered, and evaporated to give 18.25 g of a clear brown oil. The product was purified by flash column chromatography (1% to 4% ethyl acetete in dichloromethane) to give the title compound (9.86 g, 86%) as a pale yellow oil which crystallized upon standing. $^1$H-NMR (300 MHz, CDCl$_3$) δ 7.81 (d, 1 H, J =2.6 Hz), 7.55 (dd, 1 H, J=2.6, 8.9 Hz), 7.02 (d, 1 H, J=8.9 Hz), 6.53 (m, 2H), 6.41 (t, 1 H, J=2.2 Hz), 3.99 (s, 3 H), 2.24 (s, 3 H). Mass spectrum (MALDI-TOF, α-cyano-4-hydroxycinnamic acid matrix) calcd. for $C_{14}H_{13}ClO_5S$: 351.0 (M+Na). Found: 351.1.

b) 3-(2-Methoxyphenylsulfonyloxy)-5-methylphenol

4-Methylmorpholine (3.2 mL, 29.1 mmol) was added to a mixture of 3-(5-chloro-2- methoxyphenylsulfonyloxy)-5-methylphenol (8.82 g, 26.8 mmol, as prepared in the preceding step) and 10% palladium on carbon (2.23 g) in deoxygenated methanol (15 mL). The mixture was hydrogenated (atmospheric pressure) at ambient temperature for 3 h then filtered through Celite with methanol. Solvent was removed in vacuo and the crude product was purified by flash column chromatography (dichloromethane to 5% ethyl acetate in dichloromethane) to give the title compound (4.97 g, 63%) as a colorless syrup. $^1$H-NMR (300 MHz, DMSO-d,) δ 9.71 (s, 1 H), 7.76 (ddd, 1 H, J=1.7, 7.4, 8.4 Hz), 7.69 (dd, 1 H, J=1.7, 7.9 Hz), 7.38 (d, 1 H, J=8.4 Hz), 7.09 (dt, 1 H, J=1.0, 7.9 Hz), 6.48 (br s, 1 H), 6.33 (br s, 1 H), 6.26 (t, 1 H, J=2.2 Hz), 4.00 (s, 3 H), 2.15 (s, 3 H). Mass spectrum (MALDI-TOF, α-cyano-4-hydroxycinnamic acid matrix) calcd. for $C_{14}H_{14}O_5S$: 317.0 (M+Na). Found: 316.9 c) 3-[3-(2-Methoxyphenylsulfonyloxy)-5-methylphenoxy]propanol

Tri-n-butylphosphine (8.4 mL, 34 mmol) was added dropwise over 5 min to 3-(2-methoxyphenylsulfonyloxy)-5-methylphenol (4.97 g, 16.9 mmol, as prepared in the preceding step), 1,3-propanediol (12 mL, 170 mmol) and 1,1'-(azodicarbonyl)dipiperidine (8.54 g, 33.8 mmol) in anhydrous tetrahydrofuran (75 mL) at 0° C. under a nitrogen atmosphere. Dichloromethane (75 mL) was added mid-way through the tri-n-butylphosphine addition to aid stirring. The slurry was stirred at ambient temperature for 1 h, then the mixture was cooled to 0° C. and more 1,1'-(azodicarbonyl)dipiperidine (4.27 g, 16.9 mmol) and tri-n-butylphosphine (4.2 mL, 16.9 mmol) were added. The reaction was stirred overnight at ambient temperature. Diethyl ether (200 mL) was added and the mixture was filtered. The filtrate was concentrated in vacuo, and the residue was purified by flash column chromatography (25% ethyl acetate in hexane to 60% ethyl acetate in hexane, then 2% acetone in dichloromethane to 7% acetone in dichloromethane in two separate chromatographic separations) to give the title compound (3.79 g, 64%) as a gold oil. $^1$H-NMR (300 MHz, CDCl$_3$) δ 7.82 (dd, 1 H, J=1.7, 7.9 Hz), 7.61 (ddd, 1 H, J=1.8, 7.5, 8.4 Hz), 7.08 (d, 1 H, J=8.4 Hz), 7.01 (ddd, 1 H, J=1, 7.5, 7.9 Hz), 6.58 (br s, 1 H), 6.51 (br s, 1 H), 6.46 (t, 1 H, J=2.1 Hz), 4.02 (s, 3 H), 4.00 (t, 2 H, J=6.0Hz), 3.81 (m, 2 H), 2.24 (s, 3 H), 1.98 (pentet, 2 H, J=6.0 Hz), 1.72 (t, 1 H, J=5.0 Hz). Mass spectrum (MALDI-TOF, α-cyano-4-hydroxycinnamic acid matrix) calcd. for $C_{17}H_{20}O_6S$: 375.1 (M+Na). Found: 375.1.

d) 3-[3-(2-Methoxyphenylsufonyloxy)-5-methylphenoxy]propionaldehyde

Sulfur trioxide pyridine complex (1.87 g, 11.7 mmol) was added portionwise over 15 min to a solution of 3-[3-(2-methoxyphenylsulfonyloxy)-5-methylphenoxy]propanol (2.07 g, 5.9 mmol, as prepared in the preceding step), N,N-diisopropylethylamine (2.15 mL, 12.3 mmol), and anhydrous dimethyl sulfoxide (1.25 mL, 17.6 mmol) in anhydrous dichloromethane (14 mL) at 0° C. under a nitrogen atmosphere. The solution was stirred at 0° C. for 1 h, then the reaction was quenched with 5% aqueous citric acid (50 mL). The layers were separated, and the aqueous layer was extracted with dichloromethane (15 mL). The combined organic extracts were washed with 5% aqueous citric acid (50 mL), pH 7 buffer (40 mL) and brine (50 mL), dried over Na$_2$SO$_4$, filtered, and evaporated. The residual gold oil was purified by flash column chromatography (3:2 diethyl ether/hexane) to give the title compound (1.28 g, 62%) as a colorless oil. $^1$H-NMR (300 MHz, CDCl$_3$) δ 9.82 (t, 1 H, J=1.5 Hz), 7.82 (dd, 1 H, J=1.7, 7.9 Hz), 7.62 (ddd, 1 H, J=1.8, 7.4, 8.4 Hz), 7.09 (dd, 1 H, J=0.8, 8.4 Hz), 7.02 (m, 1 H), 6.58 (br s, 1 H), 6.54 (br s, 1 H), 6.45 (t, 1 H, J=2 Hz), 4.18 (t, 2 H, J=6.1 Hz), 4.02 (s, 3 H), 2.85 (td, 2 H, J=1.5,6.1Hz), 2.24 (s, 3 H). Mass spectrum (MALDI-TOF, α-cyano-4-hydroxycinnamic acid matrix) calcd. for $C_{17}H_{18}O_6S$: 373.1 (M+Na). Found: 373.0.

e) 2-[2-[3-(2-Methoxyphenylsulfonyloxy)-5-methylphenoxy]ethyl-1-methylene]hydrazinecarboximidamide acetate A mixture of aminoguanidine hydrochloride (0.811 g, 7.33 mmol) and 3-[3-(2-methoxyphenylsulfonyloxy)-5-methylphenoxy]propionaldehyde (1.28 g, 3.66 mmol, as prepared in the preceding step) in ethanol (30 mL) was stirred overnight at ambient temperature. The mixture was concentrated in vacuo to approximately 15 mL, then dichloromethane (60 mL) was added to precipitate excess aminoguanidine hydrochloride. The mixture was filtered and the filtrate was concentrated. The residue was dissolved in dichloromethane (30 mL) and extracted with aqueous NaOH (0.04N, 90 mL). The aqueous layer was extracted with dichloromethane (2×30 mL). The combined organic extracts were washed with water (50 mL) and brine (2×50 mL), dried over $K_2CO_3$, filtered, and evaporated to give the free base of the title compound (1.38 g, 93%) as a gold foam.

The acetate salt of the title compound was made by adding glacial acetic acid (0.75 mL, 30 mmol) dropwise to the free base, 2-[2-[3-(2-methoxyphenylsulfonyloxy)-5-methylphenoxy] ethyl-1-methylene] hydrazinecarboximidamide, (1.03 g, 2.53 mmol, prepared above) in dichloromethane (10 mL). The solvent was removed in vacuo at ambient temperature. The crude acetate salt was purified by flash column chromatography (20% to 100% 1:10:40 acetic acid/methanol/dichloromethane in dichloromethane) to give the title compound (0.91 g, 77%) as a white foam. $^1$H-NMR (300 MHz, $CDCl_3$) δ 7.81 (dd, 1 H, J=1.7, 7.9 Hz), 7.62 (ddd, 1 H, J=1.7, 7.5, 8.4 Hz), 7.54 (t, 1 H, J=5 Hz), 7.09 (d, 1 H, J=8.4 Hz), 7.02 (td, 1 H, J=0.9, 7.9 Hz), 6.57 (br s, 1 H), 6.50 (br s, 1 H), 6.46 (br s, 1 H), 4.05 (t, 2 H, J=6 Hz), 4.01 (s, 3 H), 2.68 (q, 2 H, J=6 Hz), 2.23 (s, 3 H). Mass spectrum (MALDI-TOF, α-cyano-4-hydroxycinnamic acid matrix) calcd. for $C_{18}H_{22}N_4O_5S$: 407.1 (M+H). Found: 407.0.

EXAMPLE 9

2-[2-[3-(5-Bromo-2-methoxyphenylsulfonyloxy)-5-methilphenoxy]ethyl-1-methylene] hydrazinecarboximidamide nitrate a) 3-(5-Bromo-2-methoxyphenylsulfonyloxy)-5-methylphenol To a solution of 1.25 g (8.76 mmol) of orcinol monohydrate and 2.50 g (8.76 mmol) of 5-bromo-2-methoxybenzenesulfonyl chloride in 25 mL of diethyl ether was added 25 mL of saturated aqueous $NaHCO_3$ and the biphasic mixture stirred vigorously at ambient temperature for 3 days. The layers were separated and the aqueous layer extracted with 2×30 mL of ethyl acetate. The combined organic layers were washed with 50 mL of brine, dried ($Na_2SO_4$) and concentrated to 1.92 g (59%) of the desired product as a pale yellow crystalline solid: $^1$H-NMR (300 MHz; $CDCl_3$) δ 7.93 (d, 1 H, J=2.5 Hz), 7.69 (dd, 1 H, J=8.9, 2.5 Hz), 6.98 (d, 1 H, J=8.9 Hz), 6.54 (br s, 1 H), 6.51 (br s, 1 H), 6.41 (t, 1 H, J=2.2 Hz), 3.98 (s, 3 H) and 2.24 (s, 3 H).

b) 3-[3-(5-Bromo-2-methoxyphenylsulfonyloxy)-5-methylphenoxy]propanol

To 1.39 g (3.72 mmol) 3-(5-bromo-2-methoxyphenylsulfonyloxy)-5-methylphenol, as prepared in the preceding step, 2.69 mL (37.2 mmol) of 1,3-propanediol and 1.95 g (7.44 mmol) of triphenylphosphine in 25 mL of anhydrous tetrahydrofuran was added 1.17 mL (7.44 mmol) of diethyl azodicarboxylate dropwise over 15 min. After stirring at ambient temperature for 2 h, the reaction mixture was concentrated to a semisolid. The resulting mixture was flash chromatographed on 250 g of silica gel with 60% ethyl acetate-hexane to give a mixture of desired product and triphenylphosphine oxide. A second chromatography on 120 g of silica gel with 8% acetone-dichloromethane afforded 1.43 g (89% yield) of the pure title compound as a colorless resin: $^1$H-NMR (300 MHz; $CDCl_3$) δ 7.95 (d, 1 H, J=2.5 Hz), 7.70 (dd, 1 H, J=8.9, 2.5 Hz), 6.98 (d, 1 H, J=8.9 Hz), 6.62 (br s, 1 H), 6.52 (br s, 1 H), 6.46 (t, 1 H, J=2.0 Hz), 4.03 (t, 2 H, J=6.0 Hz), 4.00 (s, 3 H), 3.84 (q, 2 H, J=5.7 Hz), 2.26 (s, 3 H) and 2.00 (m, 2 H). Mass spectrum (MALDI-TOF, α-cyano-4-hydroxycinnamic acid matrix) calcd. for $C_{17}H_{19}{}^{81}BrO_6S$: 455.0 (M+Na). Found: 454.8.

c) 3-[3-(5-Bromo-2-methoxyphenylsulfonyloxy)-5-methylphenoxy]propionaldehyde

To a cooled (0° C), stirred solution of 990 mg (2.30 mmol) 3-[3-(5-bromo-2-methoxyphenylsulfonyloxy)-5-methylphenoxy]propanol, as prepared in the preceding step, 842 μL of N,N-diisopropylethylamine and 500 μL of anhydrous dimethyl sulfoxide in 6.0 mL of anhydrous dichloromethane was added 732 mg (4.60 mmol) of sulfur trioxide pyridine complex. The mixture was warmed to ambient temperature over 30 min and stirred for 2 h. An additional 368 mg (2.30 mmol) of sulfur trioxide pyridine complex was added and, after 17 h, the mixture was poured into 15 mL of dichloromethane and washed with 5% (w/v) aqueous citric acid (2×25 mL). Each wash was extracted with 5 mL of dichloromethane and the combined extracts were washed with 1M pH 7 buffer (25 mL), brine (25 mL) and dried over $Na_2SO_4$ to give after concentration a white semisolid. This material was chromatographed on 35 g of silica gel with dichloromethane followed by 3% ethyl acetate-dichloromethane to afford 685 mg (69%) of the title compound as a colorless syrup: $^1$H-NMR (300 MHz; $CDCl_3$) δ 9.84 (t, 1 H, J=1.4 Hz), 7.94 (d, 1 H, J=2.5 Hz), 7.70 (dd, 1 H, J=8.9, 2.5 Hz), 6.98 (d, 1 H, J=8.9 Hz), 6.61 (br s, 1 H), 6.55 (br s, 1 H), 6.45 (t, 1 H, J=2.2 Hz), 4.21 (t, 2 H, J=6.1 Hz), 4.01 (s, 3 H), 2.88 (td, 2 H, J=6.1, 1.4 Hz) and 2.27 (s, 3 H). Mass spectrum (MALDI-TOF, gentisic acid matrix) calcd. for $C_{17}H_{17}{}^{79}BrO_6S$: 451.0 (M+Na). Found: 451.4.

d) 2-[2-[3-(5-Bromo-2-methoxyphenylsulfonyloxy)-5-methylphenoxy]ethyl-1-methylene] hydrazinecarboximidamide nitrate To 248 mg (0.578 mmol) of 3-[3-(5-bromo-2-methoxyphenylsulfonyloxy)-5-methylphenoxy] propionaldehyde, as prepared in the preceding step, in 5.0 mL of absolute ethanol was added 158 mg (1.16 mmol) of aminoguanidine nitrate and the mixture stirred at ambient temperature for three days. The mixture was diluted slowly with 30 mL of water, stirred for 10 min and filtered washing with 5 mL of cold water. The solid was air-dried under suction followed by high vacuum to afford 268 mg (85%) of the title compound as a white solid: $^1$H-NMR (300 MHz; DMSO-$d_6$) δ 11.24 (br s, 1 H), 7.97 (dd, 1 H, J=8.9, 2.5 Hz), 7.75 (d, 1 H, J=2.5 Hz), 7.55 (t, 1 H, J=5.0 Hz), 7.48 (br s, 3 H), 7.38 (d, 1 H, J=9.0 Hz), 6.76 (s, 1 H), 6.49 (s, 1 H), 6.47 (s, 1 H), 4.16 (t, 2 H, J=6.3 Hz), 4.00 (s, 3 H), 2.69 (dd, 2 H, J=11.4, 6.2 Hz) and 2.23 (s, 3 H). Mass spectrum (MALDI-TOF, α-cyano-4-hydroxycinnamic acid matrix) calcd. for $C_{18}H_{21}{}^{81}BrN_4O_5S$: 487.0 (M+H). Found: 486.9.

EXAMPLE 10

2-[2-[5-Methyl-3-(2-trifluoromethoxyphenylsulfonyloxy)phenoxy]ethyl-1-methylene]hydrazinecarboximidamide nitrate a) 5-Methyl-3-(2-trifluoromethoxyphenylsulfonyloxy)phenol Orcinol monohydrate (1.42 g, 10.0 mmol) and 2-trifluoromethoxybenzenesulfonyl chloride (2.35 g, 9.0 mmol) were mixed in saturated aqueous $NaHCO_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over $Na_2SO_4$. After removing the solvent in vacuo, the residue was purified by flash column chromatography (dichloromethane to 5% ethyl acetate in dichloromethane) to give the title compound as a yellow oil (1.80 g, 57%). $^1$H-NMR (300 MHz, $CDCl_3$) δ 7.96 (d, J=7.9 Hz, 1H), 7.72 (t, J=7.8 Hz, 1H), 7.50 (d, J=8.1

Hz, 1H), 7.40 (t, J=7.8 Hz, 1H), 6.55 (s, 1H), 6.52 (s, 1H), 6.41 (s, 1H), 5.04 (s, 1H); 2.23 (s, 3H).

b) 3-[5-Methyl-3-(2-trfluoromethoxyphenylsulfonyloxy) phenoxy]propanol

To a solution of 5-methyl-3-(2-trifluoromethoxyphenylsulfonyloxy)phenol (700 mg, 2.0 mmol), as prepared in the preceding step, tri-n-butylphosphine (607 mg, 3.0 mmol) and 1,3-propanediol (760 mg, 10 mmol) in anhydrous tetrahydrofuran (20 mL) was added 1,1'-(azodicarbonyl)dipiperidine (757 mg, 3.0 mmol). The mixture was stirred at ambient temperature overnight. Hexane (30 mL) was added to the mixture, and the precipitates were removed by filtration. The filtrate was evaporated in vacuo, and the residue was purified by flash column chromatography (1:1 hexane/ethyl acetate) to give the title compound as a colorless oil (710 mg, 87%). $^1$H-NMR (300 MHz, CDCl$_3$) δ 7.96 (d, J=7.9 Hz, 1H), 7.73 (t, J=7.7 Hz, 1H), 7.52 (d, J=7.2 Hz, 1H), 7.41 (t, J=7.6 Hz, 1H), 6.63 (s, 1H), 6.52 (s, 1H), 6.48 (s, 1H), 4.01 (t, J=6.0 Hz, 2H), 3.82 (m, 2H), 2.25 (s, 3H), 1.99 (m, 2H), 1.64 (s, 1H).

c) 3-[5-Methyl-3-(2-trifluoromethoxyphenylsulfonyloxy) phenoxy]propionaldehyde

Sulfur trioxide pyridine complex (720 mg, 4.5 mmol) was added to a solution of 3-[5-methyl-3-(2-trifluoromethoxyphenylsulfonyloxy)phenoxy]propanol (610 mg, 1.5 mmol), as prepared in the preceding step, N,N-diisopropylethylamine (0.6 mL, 4.7 mmol) and anhydrous dimethyl sulfoxide (0.3 mL, 4.2 mmol) in anhydrous dichloromethane (15 mL). The reaction mixture was stirred at ambient temperature for 1 hour and then quenched with 10% aqueous citric acid (50 mL). The mixture was extracted into dichloromethane (3×50 mL), and the dichloromethane solution was washed with 10% aqueous citric acid (40 mL) and dried over Na$_2$SO$_4$. After removing the solvent in vacuo, the residue was purified by flash column chromatography (CH$_2$Cl$_2$) to give the title compound as a colorless oil (480 mg, 79%). 1H-NMR (300 MHz, CDCl$_3$) δ 9.83 (s, 1H), 7.96 (d, J=7.9 Hz, 1H), 7.73 (t, J=8.2 Hz, 1H), 7.49 (d, J=8.3 Hz, 1H), 7.41 (t, J=8.2 Hz, 1H), 6.62 (s, 1H), 6.54 (s, 1H), 6.47 (s, 1H), 4.20 (t, J=6.1 Hz, 2H), 2.87 (t, J=6.1, 2H), 2.26 (s, 3H).

d) 2-[2-[5-Methyl-3-(2-trifluoromethoxyphenylsulfonyloxy)phenoxy]ethyl-1-methylene]hydrazinecarboximidamide nitrate A solution of 3-[5-methyl-3-(2-trifluoromethoxyphenylsulfonyloxy)phenoxy] propionaldehyde (445 mg, 1. 1 mmol), as prepared in the preceding step, and aminoguanidine nitrate (300 mg, 2.2 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (525 mg, 91%). $^1$H-NMR (300 MHz, DMSO-d$_6$) δ 7.97 (d, J=7.8 Hz, 2H), 7.77 (d, J=7.8 Hz, 1H), 7.63 (t, J=8.2 Hz, 1H), 7.54 (t, J=5.0 Hz, 1H), 7.46 (br s, 4H), 4.15 (t, J=6.4 Hz, 2H), 2.68 (m, 2H), 2.21 (s, 3H). Mass spectrum (MALDI-TOF, α-cyano-4-hydroxycinnamic acid matrix) calcd. for C$_{18}$H$_{19}$F$_3$N$_4$O$_5$S: 461.1 (M+H), 483.1 (M+Na). Found: 461.0, 482.8.

EXAMPLE 11

2-[2-[3-(Benzo-2,1,3-thiadiazole-4-sulfonyloxy)-5-methylphenoxy]ethyl-1-methylene] hydrazinecarboximidamide nitrate a) 3-(Benzo-2,1,3-thiadiazole-4-sulfonyloxy)-5-methylphenol Orcinol monohydrate (1.42 g, 10.0 mmol) and benzo-2,1,3-thiadiazole-4-sulfonyl chloride (2.35 g, 10.0 mmol) were mixed in saturated aqueous NaHCO$_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over Na$_2$SO$_4$. After removing the solvent in vacuo, the residue was purified by flash column chromatography (dichloromethane to 5% ethyl acetate in dichloromethane) to give the title compound as a pale yellow solid (2.55 g, 79%). $^1$H-NMR (300 MHz, CDCl$_3$) δ 8.34 (d, J=8.8 Hz, 1H), 8.26 (d, J=7.1 Hz, 1H), 7.72 (t, J=8.8 Hz, 1H), 6.53 (s, 1H), 6.47 (s, 1H), 6.37 (s, 1H), 5.24 (s, 1H), 2.19 (s, 1H).

b) 3-[3-(Benzo-2,1,3-thiadiazole-4-sulfonyloxy)-5-methylphenoxy]propanol

To a solution of 3-(benzo-2,1,3-thiadiazole-4-sulfonyloxy)-5-methylphenol (645 mg, 2.0 mmol), as prepared in the preceding step, tri-n-butylphosphine (607 mg, 3.0 mmol) and 1,3-propanediol (760 mg, 10 mmol) in anhydrous tetrahydrofuran (20 mL) was added 1,1'-(azodicarbonyl)dipiperidine (757 mg, 3.0 mmol). The mixture was stirred at ambient temperature overnight. Hexane (30 mL) was added to the mixture, and the precipitates were removed by filtration. The filtrate was evaporated in vacuo, and the residue was purified by flash column chromatography (1:1 hexane/ethyl acetate) to give the title compound as a pale yellow oil (615 mg, 82%). $^1$H-NMR (300 MHz, CDCl$_3$) δ 8.35 (d, J=8.7 Hz, 1H), 8.26 (d, J=7.1 Hz, 1H), 7.72 (t, J=8.8 Hz, 1H), 6.59 (s, 1H), 6.46 (s, 1H), 6.43 (s, 1H), 3.97 (t, J=6.0 Hz, 2H), 3.80 (t, J=6.0 Hz, 2H), 2.21 (s, 3H), 1,96 (m, 2H), 1.65 (br s, 1H).

c) 3-[3-(Benzo-2,1,3-thiadiazole-4-sulfonyloxy)-5-methylphenoxy]propionaldehyde

Sulfur trioxide pyridine complex (720 mg, 4.5 mmol) was added to a solution of 3-[3-(benzo-2,1,3-thiadiazole-4-sulfonyloxy)-5-methylphenoxy]propanol (565 mg, 1.5 mmol), as prepared in the preceding step, N,N-diisopropylethylamine (0.6 mL, 4.7 mmol) and anhydrous dimethyl sulfoxide (0.3 mL, 4.2 mmol) in anhydrous dichloromethane (15 mL). The reaction mixture was stirred at ambient temperature for 1 hour and then quenched with 10% aqueous citric acid (50 mL). The mixture was extracted into dichloromethane (3×50 mL), and the dichloromethane solution was washed with 10% aqueous citric acid (40 mL) and dried over Na$_2$SO$_4$. After removing the solvent in vacuo, the residue was purified by flash column chromatography (dichloromethane) to give the title compound as a pale yellow oil (450 mg, 80%). $^1$H-NMR (300 MHz, CDCl$_3$) δ 9.82 (s, 1H), 8.35 (d, J=8.7 Hz, 1H), 8.27 (d, J=7.1 Hz, 1H), 7.72 (t, J=8.6 Hz, 1H), 6.59 (s, 1H), 6.49 (s, 1H), 6.44 (s, 1H), 4.17 (t, J=6.0 Hz, 2H), 2.85 (t, J=6.0 Hz, 2H), 2.21 (s, 3H).

d) 2-[2-[3-(Benzo-2,1,3-thiadiazole-4-sulfonyloxy)-5-methylphenoxy]ethyl-1-methylene] hydrazinecarboximidamide nitrate A solution of 3-[3-(benzo-2,1,3-thiadiazole-4-sulfonyloxy)-5-methylphenoxy]propionaldehyde (374 mg, 1.0 mmol), as prepared in the preceding step, and aminoguanidine nitrate (280 mg, 2.0 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (440 mg, 88%). $^1$H-NMR (300 MHz, DMSO-d$_6$) δ 11.20 (br s, 1H), 8.57 (d, J=8.8 Hz, 1H), 8.30 (d, J=7.1 Hz, 1H), 7.88 (t, J=8.1 Hz, 1H), 7.51 (t, J 4.9 Hz, 1H), 7.44 (br s, 4H), 6.72 (s, 1H), 6.41 (s, 1H), 6.39 (s, 1H), 4.07 (t, J=6.4 Hz, 2H), 2.64 (t, J=6.2 Hz, 2H), 2.26 (s, 3H). Mass spectrum (MALDI-TOF, α-cyano-4-hydroxycinnamic acid matrix) calcd. for $C_{17}H_{18}N_6O_4S_2$: 435.1 (M+H), 457.1 (M+Na). Found: 435.0, 457.1.

EXAMPLE 12

2-[2-[5-Methyl-3-(3-methylphenylsulfonyloxy)phenoxy]ethyl-1-methylene]hydrazinecarboximidamide nitrate a) 5-Methyl-3-(3-methylphenylsulfonyloxy)phenol Orcinol monohydrate (1.42 g, 10.0 mmol) and 3-methylbenzenesulfonyl chloride (1.60 g, 8.0 mmol) were mixed in saturated aqueous $NaHCO_3$ (30 mL) and diethyl ether (30 mL). The biphasic mixture was stirred vigorously at ambient temperature overnight. The reaction mixture was diluted with water (50 mL) and extracted into ethyl acetate (3×40 mL). The organic phase was washed with brine (2×30 mL) and dried over $Na_2SO_4$. After removing the solvent in vacuo, the residue was purified by flash column chromatography (dichloromethane to 5% ethyl acetate in dichloromethane) to give the title compound as a yellow oil (2.1 g, 76%). $^1$H-NMR (300 MHz, $CDCl_3$) δ 7.68 (s, 1H), 7.64 (d, J=7.9 Hz, 1H), 7.45 (t, J=7.8 Hz, 1H), 7.40 (t, J=7.6 Hz, 1H), 6.54 (s, 1H), 6.39 (s, 1H), 6.32 (s, 1H), 5.33 (s, 1H), 2.41 (s, 3H), 2.21 (s, 3H).

b) 3-[5-Methyl-3-(3-methylphenylsulfonyloxy)phenoxy]propanol

To a solution of 5-methyl-3-(3-methylphenylsulfonyloxy)phenol (560 mg, 2.0 mmol), as prepared in the preceding step, tri-n-butylphosphine (607 mg, 3.0 mmol) and 1,3-propanediol (760 mg, 10 mmol) in anhydrous tetrahydrofuran (20 mL) was added 1,1'-(azodicarbonyl)dipiperidine (757 mg, 3.0 mmol). The mixture was stirred at ambient temperature overnight. Hexane (30 mL) was added to the mixture, and the precipitates were removed by filtration. The filtrate was evaporated in vacuo, and the residue was purified by flash column chromatography (1:1 hexane/ethyl acetate) to give the title compound as a colorless oil (605 mg, 90%). 1H-NMR (300 MHz, $CDCl_3$) δ 7.69 (s, 1H), 7.65 (d, J=7.6 Hz, 1H), 7.46 (t, J=7.5 Hz, 1H), 7.41 (t, J=7.6 Hz, 1H), 6.62 (s, 1H), 6.41 (s, 1H), 6.36 (s, 1H), 4.13 (t, J=7.2 Hz, 2H), 3.81 (m, 2H), 2.43 (s, 3H), 2.24 (s, 3H), 1.96 (m, 2H), 1.61 (br s, 1H).

c) 3-[5-Methyl-3-(3-methylphenylsulfonyloxy)phenoxy]propionaldehyde

Sulfur trioxide pyridine complex (720 mg, 4.5 mmol) was added to a solution of 3-[5-methyl-3-(3-methylphenylsulfonyloxy)phenoxy]propanol (505 mg, 1.5 mmol), as prepared in the preceding step, N,N-diisopropylethylamine (0.6 mL, 4.7 mmol) and anhydrous dimethyl sulfoxide (0.3 mL, 4.2 mmol) in anhydrous dichloromethane (15 mL). The reaction mixture was stirred at ambient temperature for 1 hour and then quenched with 10% aqueous citric acid (50 mL). The mixture was extracted into dichloromethane (3×50 mL), and the dichloromethane solution was washed with 10% aqueous citric acid (40 mL) and dried over $Na_2SO_4$. After removing the solvent in vacuo, the residue was purified by flash column chromatography (dichloromethane) to give the title compound as a colorless oil (450 mg, 89%). $^1$H-NMR (300 MHz, $CDCl_3$) δ 9.83 (s, 1H), 7.69 (s, 1H), 7.65 (d, J=7.6 Hz, 1H), 7.46 (t, J=7.7 Hz, 1H), 7.41 (t, J=7.6 Hz, 1H), 6.61 (s, 1H), 6.44 (s, 1H), 6.35 (s, 1H), 4.18 (t, J=6.0 Hz, 2H), 2.85 (t, J=6.1 Hz, 2H), 2.43 (s, 3H), 2.24 (s, 3H).

d) 2-[2-[5-Methyl-3-(3-methylphenylsulfonyloxy)phenoxy]ethyl-1-methylene]hydrazinecarboximidamide nitrate A solution of 3-[5-methyl-3-(3-methylphenylsulfonyloxy)phenoxy]propionaldehyde (400 mg, 1.2 mmol), as prepared in the preceding step, and aminoguanidine nitrate (345 mg, 2.5 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (350 mg, 66%). $^1$H-NMR (300 MHz, DMSO-$d_6$) δ 11.49.(br s, 1H), 7.73 (s, 1H), 7.50–7.67 (m, 8 H), 6.75 (s, 1H), 6.45 (s, 1H), 6.41 (s, 1H), 4.12 (t, J=6.4 Hz, 2H), 2.67 (m, 2H), 2.41 (s, 3H), 2.21 (s, 3H). Mass spectrum (MALDI-TOF, α-cyano-4-hydroxycinnamic acid matrix) calcd. for $C_{18}H_{22}N_4O_4S$: 391.1 (M+H), 413.1 (M+Na). Found: 391.1, 413.1.

EXAMPLE 13

2-[2-[3-(2-Cyanophenylsulfonyloxy)-5-methylphenoxy]ethyl-1-methylene]hydrazinecarboximidamide hydrochloride a) 3-(2-Cyanophenylsulfonyloxy)-5-methylphenol Orcinol monohydrate (1.42 g, 10.0 mmol) and 2-cyanobenzenesulfonyl chloride (2.02 g, 10.0 mmol) were mixed in saturated aqueous $NaHCO_3$ (30 mL) and diethyl ether (30 mL). The biphasic mixture was stirred vigorously at room temperature overnight. The reaction mixture was diluted with water (50 mL) and extracted into ethyl acetate (3×50 mL). The organic phase was washed with brine (2×50 mL) and dried over $Na_2SO_4$. After removing the solvent in vacuo, the residue was purified by flash column chromatography (dichloromethane to 5% ethyl acetate in dichloromethane) to give the title compound as a white solid (1.65 g, 57%). $^1$H-NMR (300 MHz, $CDCl_3$) δ 8.07 (m, 1H), 7.94 (m, 1H), 7.75–7.80 (m, 2H), 6.57 (s, 1H), 6.53 (s, 1H), 6.49 (s, 1H), 5.69 (br s, 1H), 2.22 (s, 3H).

b) 3-[3-(2-Cyanophenylsulfonyloxy)-5-methylphenoxy]propanol

To a solution of 3-(2-cyanophenylsulfonyloxy)-5-methylphenol (580 mg, 2.0 mmol), as prepared in the preceding step, tri-n-butylphosphine (607 mg, 3.0 mmol), and 1,3-propanediol (760 mg, 10 mmol) in anhydrous tetrahydrofuran (20 mL) was added 1,1'-(azodicarbonyl)dipiperidine (757 mg, 3.0 mmol). The mixture was stirred at room temperature overnight. Hexane (30 mL) was added to the mixture, and the precipitates were removed by filtration. The filtrate was evaporated in vacuo, and the residue was purified by flash column chromatography (10% ethyl acetate in dichloromethane) to give the title compound as a colorless oil (560 mg, 80%). $^1$H-NMR (300 MHz, $CDCl_3$) δ 8.11 (m, 1H), 7.94 (m, 1H), 7.77–7.82 (m, 2H), 6.65 (s, 1H), 6.59 (s, 1H), 6.57 (s, 1H), 4.05 (t, J=6.0 Hz, 2H), 3.82 (t, J=6.0 Hz, 2H), 2.26 (s, 3H), 2.00 (m, 2H), 1.76 (brs, 1H).

c) 3-[3-(2-Cyanophenylsulfonyloxy)-5-methylphenoxy]propionaldehyde

Sulfur trioxide pyridine complex (480 mg, 3.0 mmol) was added to a solution of 3-[3-(2-cyanophenylsulfonyloxy)-5-methylphenoxy]propanol (315 mg, 0.9 mmol), as prepared in the preceding step, N,N-diisopropylethylamine (0.5 mL, 3.9 mmol) and anhydrous dimethyl sulfoxide (0.2 mL, 2.8 mmol) in anhydrous dichloromethane (10 mL). The reaction mixture was stirred at ambient temperature for 1 hour and then quenched with 10% aqueous citric acid (30 mL). The mixture was extracted into dichloromethane (3×40 mL), and the dichloromethane solution was washed with 10% aqueous citric acid (30 mL) and dried over $Na_2SO_4$. After removing the solvent in vacuo, the residue was purified by flash column chromatography (dichloromethane) to give the title compound as a colorless oil (260 mg, 83%). $^1$H-NMR (300 MHz, CDCl$_3$) δ 9.84 (s, 1H), 8.11 (m, 1H), 7.94 (m, 1H), 7.78–7.81 (m, 2H), 6.65 (s, 1H), 6.61 (s, 1H), 6.57 (s, 1H), 4.24 (t, J=6.0 Hz, 2H), 2.88 (t, J=6.0 Hz, 2H), 2.27 (s, 3H).

d) 2-[2-[3-(2-Cyanophenylsulfonyloxy)-5-methylphenoxy]ethyl-1-methylene]hydrazinecarboximidamide hydrochloride A solution of 3-[3-(2-cyanophenylsulfonyloxy)-5-methylphenoxy]propionaldehyde (240 mg, 0.7 mmol), as prepared in the preceding step, and aminoguanidine nitrate (200 mg, 1.5 mmol) in ethanol (8 mL) was stirred at ambient temperature overnight. Water (20 mL) was added to the reaction mixture. The precipitates were collected, washed with water (2×15 mL) and diethyl ether (2×20 mL), and dried under high vacuum. The solid was suspended in water (40 mL), treated with 2.0N sodium hydroxide (1.0 mL), and extracted into dichloromethane (3×50 mL). The organic phase was dried over K$_2$CO$_3$. After removing the solvent, the residue was dissolved in dichloromethane (1 mL), and the dichloromethane solution was added to the solution of 1.5 mL of 0.6M methanolic HCl in diethyl ether (50 mL) to give the title compound as a colorless solid (245 mg, 80%). $^1$H-NMR (300 MHz, DMSO-d$_6$) δ 8.28 (m, 1H), 8.09 (m, 1H), 7.97–8.04 (m, 2H), 7.55 (br s, 5 H), 6.80 (s, 1H), 6.50 (s, 2H), 4.15 (t, J=6.3 Hz, 2H), 2.68 (m, 2H), 2.22 (s, 3H). Mass spectrum (MALDI-TOF, α-cyano-4-hydroxycinnamic acid matrix) calcd. for C$_{19}$H$_{19}$N$_5$O$_4$S: 402.1 (M+H), 424.1 (M+Na), 440.1 (M+K). Found: 402.1, 424.1, 440.1.

EXAMPLE 14

2-[2-[3-(2-Methoxy-5-methylphenylsulfonyloxy)-5-methylphenoxy]ethyl-1-methylene]hydrazinecarboximidamide nitrate a) 3-(2-Methoxy-5-methylphenylsulfonyloxy)-5-methylphenol To a solution of 1.00 g (8.05 mmol) of orcinol monohydrate and 1.63 g (7.38 mmol) of 2-methoxy-m-toluenesulfonyl chloride in 20 mL of diethyl ether was added 20 mL of saturated aqueous NaHCO$_3$ and the biphasic mixture stirred vigorously at ambient temperature for 3 days. The layers were separated and the aqueous layer extracted with 2×30 mL of ethyl acetate. The combined organic layers were washed with 50 mL of brine, dried (Na$_2$SO$_4$) and concentrated to give 2.2 g of an orange syrup. Crystallization from dichloromethane-hexane (two crops) afforded 1.24 g (54%) of the title compound as a light orange powder: $^1$H-NMR (300 MHz; CDCl$_3$) δ 7.62 (d, 1 H, J=2.0 Hz), 7.40 (m, 1 H), 6.96 (d, 1 H, J=8.5 Hz), 6.52 (m, 2 H), 6.42 (t, 1 H, J=2.1 Hz), 5.13 (s, 1 H), 3.96 (s, 3 H), 2.29 (s, 3 H) and 2.23 (s, 3 H).

b) 3-[3-(2-Methoxy-5-methylphenylsulfonyloxy)-5-methylphenoxy]propanol

To 458 mg (1.49 mmol) 3-(2-methoxy-5-methylphenylsulfonyloxy)-5-methylphenol, as prepared in the preceding step, 1.08 mL (14.9 mmol) of 1,3-propanediol and 782 mg (2.98 mmol) of triphenylphosphine in 10 mL of anhydrous tetrahydrofuran was added 0.470 mL (2.98 mmol) of diethyl azodicarboxylate dropwise over 15 min. After stirring at ambient temperature for 2 h, the reaction mixture was concentrated to a semisolid. The resulting mixture was flash chromatographed on 50 g of silica gel with 8–10% ethyl acetate-dichloromethane. Impure fractions were re-chromatographed on 40 g of silica gel with 50–100% ethyl acetate-hexane. Material from the two purifications was combined to afford 530 mg (97% yield) of the title compound as a colorless oil: $^1$H-NMR (300 MHz; CDCl$_3$) δ 7.95 (d, 1 H, J=2.2 Hz), 7.40 (dd, 1 H, J=8.5, 2.3 Hz), 6.97 (d, 1 H, J=8.5 Hz), 6.59 (br s, 1 H), 6.53 (br s, 1 H), 6.47 (t, 1 H, J=2.1 Hz), 4.01 (t, 2 H, J=6.0 Hz), 3.98 (s, 3 H), 3.81 (q, 2 H, J=5.7 Hz), 2.29 (s, 3 H), 2.25 (s, 3 H) and 1.98 (m, 2 H).

c) 3-[3-(2-Methoxy-5-methylphenylsulfonyloxy)-5-methylphenoxy]propionaldehyde

To a cooled (0° C.), stirred solution of 528 mg (1.44 mmol) of 3-[3-(2-methoxy-5-methylphenylsulfonyloxy)-5-methylphenoxy]propanol, as prepared in the preceding step, 527 μL (3.02 mmol) of N,N-diisopropylethylamine and 307 μL (4.32 mmol) of anhydrous dimethyl sulfoxide in 6.0 mL of anhydrous dichloromethane was added 459 mg (2.88 mmol) of sulfur trioxide pyridine complex. The mixture was warmed to ambient temperature over 30 min and stirred for 16 h. The mixture was poured into 15 mL of dichloromethane and washed with 5% (w/v) aqueous citric acid (2×25 mL). Each wash was extracted with 5 mL of dichloromethane and the combined extracts were washed with brine (25 mL), dried over Na$_2$SO$_4$ and concentrated. The resulting material was chromatographed on 35 g of silica gel with dichloromethane followed by 3% ethyl acetate-dichloromethane to afford 320 mg (61%) of the title compound as a colorless syrup: $^1$H-NMR (300 MHz; CDCl$_3$) δ 9.83 (t, 1 H, J=1.4 Hz), 7.63 (d, 1 H, J=2.3 Hz), 7.40 (dd, 1 H, J=8.5, 2.3 Hz), 6.98 (d, 1 H, J=8.5 Hz), 6.59 (br s, 1 H), 6.55 (br s, 1 H), 6.46 (t, 1 H, J=2.1 Hz), 4.19 (t, 2 H, J=6.1 Hz), 3.98 (s, 3 H), 2.85 (td, 2 H, J=6.1, 1.4 Hz), 2.29 (s, 3 H) and 2.25 (s, 3 H).

d) 2-[2-[3-(2-Methoxy-5-methylphenylsulfonyloxy)-5-methylphenoxy]ethyl-1-methylene]hydrazinecarboximidamide nitrate To 305 mg (0.837 mmol) of 3-[3-(2-methoxy-5-methylphenylsulfonyloxy)-5-methylphenoxy]propionaldehyde, as prepared in the preceding step, in 8.0 mL of absolute ethanol was added 230 mg (1.67 mmol) of aminoguanidine nitrate and the mixture stirred at ambient temperature for three days. The mixture was diluted slowly with 40 mL of water, stirred for 10 min and filtered washing with 5 mL of cold water. The solid was air-dried under suction followed by high vacuum to afford 290 mg (72%) of the title compound as a white solid: $^1$H-NMR (300 MHz; DMSO-d$_6$) δ 11.20 (br s, 1 H), 7.55 (m, 3 H), 7.45 (br s, 3 H), 7.27 (d, 1 H, J=8.6 Hz), 6.73 (s, 1 H), 6.48 (s, 1 H), 6.44 (s, 1 H), 4.14 (t, 2 H, J=6.3 Hz), 3.95 (s, 3 H), 2.68 (dd, 2 H, J=11.3,6.2 Hz), 2.26 (s, 3 H) and 2.22 (s, 3 H). Mass spectrum (MALDI-TOF, α-cyano-4-hydroxycinnamic acid matrix) calcd. for C$_{19}$H$_{24}$N$_4$O$_5$S: 421.2 (M+H). Found: 421.3.

EXAMPLE 15

2-[2-[5-Methyl-3-(quinolinyl-8-sulfonyloxy)phenoxy]ethyl-1-methylene]hydrazinecarboximidamide acetate a) 5-Methyl-3-(quinolinyl-8-sulfonyloxy)phenol A mixture of orcinol monohydrate (4.0 g, 28 mmol) and 8-quinolinesulfonyl chloride (6.1 g, 26.7 mmol) in diethyl ether (120 mL) and saturated aqueous sodium bicarbonate (120 mL) was vigorously stirred at ambient temperature for 4 days. The reaction mixture was extracted into ethyl acetate, dried (MgSO$_4$), and concentrated. Crystallization from diethyl ether/ethyl acetate/hexane gave 4.48 g (50%) of the title compound as a tan powder. $^1$H-NMR (300 MHz, DMSO-d$_6$) δ 9.62 (br s, 1 H), 9.23 (dd, 1 H, J 2, 4 Hz), 8.63(dd, 1 H, J=2, 8 Hz),8.45 (dd, 1 H, J=2, 8 Hz), 8.36 (dd, 1 H, J=2, 8 Hz), 7.74–7.83 (m, 2 H), 6.44 (br s, 1 H), 6.29 (br s, 1 H), 6.10 (t, 1 H, J=2 Hz), 2.09 (s, 3 H). Mass spectrum (MALDI-TOF, α-cyano-4- hydroxycinnamic acid matrix) calcd. for $C_{16}H_{13}NO_4S$: 316.1 (M+H), 338.0 (M+Na). Found 316.0, 338.1.

b) 3-[5-Methyl-3-(quinolinyl-8-sulfonyloxy)phenoxy] propanol

To 5-methyl-3-(quinolinyl-8-sulfonyloxy)phenol (3.0 g, 9.0 mmol), as prepared in the preceding step, 1,3-propanediol (4 mL, 55.2 mmol), and 1,1'-(azodicarbonyl) dipiperidine (3.42 g, 13.6 mmol) at 0° C. in anhydrous tetrahydrofuran (60 mL) was added slowly tri-n-butylphosphine (3.36 mL, 13.5 mmol). The cold bath was removed, and the reaction mixture was stirred at ambient temperature overnight. TLC analysis showed starting material. To the reaction mixture was added sequentially 1,1'-(azodicarbonyl)dipiperidine (1.9 g) and tri-n-butylphosphine (1.7 mL). The reaction mixture was stirred at ambient temperature for 2 h. The reaction mixture was diluted with diethyl ether and the resulting suspension was filtered. The filtrate was concentrated and purified by flash chromatography using elutions of dichloromethane/ethyl acetate (3:1 then 2:3) to give 3.19 g of the title compound as an oil. $^1$H-NMR (300 MHz, CDCl$_3$) δ 9.27 (dd, 1 H, J=2,4Hz), 8.41 (dd, 1 H, J=2,7Hz), 8.31 (dd, 1 H, J=2, 8 Hz), 8.14 (dd, 1 H, J=2, 7 Hz), 7.61–7.65 (m, 2 H), 6.54 (br s, 1 H), 6.49 (br s, 1 H), 6.42 (t, 1 H, J=2 Hz), 3.92 (t, 2 H, J=6 Hz), 3.77 (t, 2 H), 2.17 (s, 3 H). Mass spectrum (MALDI-TOF, α-cyano-4-hydroxycinnamic acid matrix) calcd. for $C_{19}H_{19}NO_5S$: 374.1 (M+H), 396.1 (M+Na). Found: 374.0, 396.2.

c) 3-[5-Methyl-3-(quinolinyl-8-sulfonyloxy)phenoxy] propionaldehyde

To a solution of 3-[5-methyl-3-(quinolinyl-8-sulfonyloxy) phenoxy]propanol (4.33 g, 11.1 mmol), as prepared by the procedure of step b of this example, 3.9 mL (22 mmol) of N,N-diisopropylethylamine, and 1.4 ml (18.1 mmol) of anhydrous dimethyl sulfoxide in anhydrous dichloromethane (70 mL) at 0° C. was added portionwise 2.84 g (18 mmol) of sulfur trioxide pyridine complex. The reaction mixture was stirred at 0° C for 45 min, then another 150 μL of anhydrous dimethyl sulfoxide and 290 mg of sulfur trioxide pyridine complex were added. The reaction mixture was stiffed at 0° C. for another 45 min. The reaction mixture was diluted with 70 mL of toluene and concentrated. The oily residue was diluted with 160 mL of diethyl ether and 40 mL of ethyl acetate, washed with 4×100 mL water, dried (MgSO$_4$), and concentrated to provide 3.94 g of the title compound oil which was used directly in the next reaction. $^1$H-NMR (300 MHz, CD$_3$OD; partial) δ 9.13–9.16 (m, 1 H), 8.50 (dd, 1 H, J=1.7, 8.4 Hz), 8.30–8.37 (m, 2 H), 7.74 (dd, 2 H, J=4.0, 8 Hz), 7.68 (t, 1 H, J=7.4 Hz), 6.56 (s, 1 H), 6.38 (t, 1 H, J=0.7 Hz), 6.22 (t, 1 H, J=2 Hz). Mass spectrum (MALDI-TOF, α-cyano-4-hydroxycinnamic acid matrix) calcd. for $C_{19}H_{17}NO_5S$: 372.1 (M+H),394.1 (M+Na),410.0 (M+K). Found: 372.1, 394.1, 410.0.

d) 2-[2-[5-Methyl-3-(quinolinyl-8-sulfonyloxy)phenoxy] ethyl-1-methylene]-hydrazinecarboximidamide acetate A solution of 3.94 g (10 mmol) of 3-[5-methyl-3-(quinolinyl-8-sulfonyloxy)phenoxy]propionaldehyde, as prepared in the preceding step, in ethanol (25 mL) was treated with 1.6 g (11.7 mmol) of aminoguanidine nitrate. The reaction mixture was stirred overnight and then treated with another 1.0 g of aminoguanidine nitrate. The reaction mixture was stirred at ambient temperature for 1 h and then quenched with 10 mL of 2N NaOH. The reaction mixture was diluted with water (50 mL) and extracted into dichloromethane (4×50 mL). The organic extracts were washed with 5 mL of 2N NaOH and then water (4×50 mL). The organic extract was dried (K$_2$CO$_3$), filtered, and diluted with 200 mL of diethyl ether. The precipitate, 2-[2-[5-methyl-3-(quinolinyl-8-sulfonyloxy)phenoxy]ethyl-1-methylene] hydrazinecarboximidamide (1.60 g), was collected after standing for 1 h at 0° C. $^1$H-NMR (300 MHz, CD$_3$OD) δ 9.14 (dd, 1 H, J=1.7,4.3 Hz), 8.50 (dd, 1 H, J=1.7, 8 Hz), 8.30–8.37 (m, 2 H), 7.73 (dd, 1 H, J=4,8Hz),7.69(t, 1 H, J=8 Hz),7.36(t, 1 H, J=5 Hz),6.58(s, 1 H), 6.40 (s,1 H), 6.22 (t, 1 H, J=2 Hz), 3.88 (t, 2 H, J=6.6 Hz), 2.52 (q, 2 H, J=6.6 Hz), 2.13 (s, 3 H).

The free base of the title compound was dissolved in methanol/dichloromethane (10 mL; 9:1) and was treated with 550 μL (9.6 mmol) of glacial acetic acid. The solution was further diluted with diethyl ether, the solvent was removed in vacuo, and the residue was repeatedly concentrated from methanol/diethyl ether/dichloromethane/ petroleum ether to give 1.9 g of the title compound as a foam. $^1$H-NMR (300 MHz, CD$_4$OD) δ 9.13 (dd, 1 H, J=1.8, 4.3 Hz), 8.52 (dd, 1 H, J=1.7, 8.4 Hz), 8.31–8.38 (m, 2 H), 7.73 (dd, 1 H, J=4.3, 8.4 Hz), 7.69 (t, 1 H, J=6.4 Hz), 7.47 (t, 1 H, J=5.2 Hz), 6.61 (s, 1 H), 6.37 (t, 1 H, J=2 Hz), 6.34(s, 1 H), 4.01 (t, 2 H, J=6.3 Hz), 2.66 (q, 2 H, J=6.2 Hz), 2.11 (s, 3 H), 1.92 (s, 3 H). Mass spectrum (MALDI-TOF, α-cyano-4-hydroxycinnamic acid matrix) calcd. for $C_{20}H_{21}N_5O_4S$: 428.1 (M+Na). Found: 428.2.

EXAMPLE 16

2-[2-[3-(2,5-Dimethoxyphenylsulfonyloxy)-5-methylphenoxy]ethyl-1-methylene] hydrazinecarboximidamide nitrate a) 3-(2,5-Dimethoxyphenylsulfonyloxy)-5-methylphenol To a solution of 1.00 g (8.05 mmol) of orcinol monohydrate and 1.75 g (7.38 mmol) of 2,5-dimethoxybenzenesulfonyl chloride in 20 mL of diethyf ether was added 20 mL of saturated aqueous NaHCO$_3$ and the biphasic mixture stirred vigorously at ambient temperature for 3 days. The layers were separated and the aqueous layer extracted with 2×30 mL of ethyl acetate. The combined organic layers were washed with 50 mL of brine, dried (Na$_2$SO$_4$) and concentrated to give an amber-colored solid. Recrystallization from ethyl acetate-hexane afforded 1.29 g (54%) of the title compound as a cream-colored powder: $^1$H-NMR (300 MHz; CDCl$_3$) δ 7.34 (d, 1 H, J=3.1 Hz), 7.15 (dd, 1 H, J=9.1, 3.1 Hz), 7.02 (d, 1 H, J=9.1 Hz), 6.53 (m, 2 H), 6.42 (t, 1H, J=2.2 Hz), 5.08 (br s, 1 H),3.95 (s,3 H), 3.76 (s, 3 H), and 2.23 (s, 3 H).

b) 3-[3-(2,5-Dimethoxyphenyisulfonyloxy)-5-methylphenoxy]propanol

To 500 mg (1.54 mmol) of 3-(2,5-dimethoxyphenylsulfonyloxy)-5-methylphenol, as prepared in the preceding step, 1.1 mL (15 mmol) of 1,3-propanediol and 808 mg (3.08 mmol) of triphenylphosphine in 12 mL of anhydrous tetrahydrofuran was added 485 mg (3.08 mmol) of diethyl azodicarboxylate dropwise over 15 min. After stirring at ambient temperature for 1 h, the reaction mixture was concentrated to a yellow syrup. The resulting mixture was flash chromatographed on 40 g of silica gel with 50–75% ethyl acetate-hexane to afford a mixture of the desired product and triphenylphosphine oxide. Chromatography on 35 g of silica gel with 4% acetone-dichloromethane afforded 483 mg (82% yield) of the title compound as a colorless resin: $^1$H-NMR (300 MHz; CDCl$_3$) δ 7.34 (d, 1 H, J=3.1 Hz), 7.15 (dd, 1 H, J=9.1, 3.1 Hz), 7.03 (d, 1 H, J=9.1 Hz), 6.59 (m, 1 H), 6.53 (m, 1 H), 6.48 (t, 1 H, J=2.1 Hz), 4.01 (t, 2 H, J=6.0 Hz), 3.97 (s, 3 H), 3.81 (dd, 2 H, J=11.2, 5.8 Hz), 3.76 (s, 3 H), 2.25 (s, 3 H) and 1.98 (pentet, 2 H, J=6.0 Hz).

c) 3-[3-(2,5-Dimethoxyph enyls ulfonyloxy)-5-methylphenoxy]propionaldehyde

To a cooled (0° C.), stirred solution of 360 mg (0.941 mmol) of 3-[3-(2,5-dimethoxyphenylsulfonyloxy)-5-methylphenoxy]propanol, as prepared in the preceding step, 344 μL (1.98 mmol) of N,N-diisopropylethylamine and 200 μL (2.82 mmol) of anhydrous dimethyl sulfoxide in 6.0 mL of anhydrous dichloromethane was added 300 mg (1.88 mmol) of sulfur trioxide pyridine complex. The mixture was warmed to ambient temperature over 30 min and stirred for 16 h. The mixture was then poured into 15 mL of dichloromethane and washed with 5% (w/v) aqueous citric acid (2×25 mL). Each wash was extracted with 5 mL of dichloromethane and the combined extracts were washed with brine (25 mL), dried over $Na_2SO_4$ and concentrated. The resulting material was chromatographed on 35 g of silica gel with dichloromethane followed by 2.5% ethyl acetate-dichloromethane to afford 268 mg (75%) of the title compound as a colorless resin: $^1$H-NMR (300 MHz; $CDCl_3$) δ 9.83 (t, 1 H, J=1.4 Hz), 7.34 (d, 1 H, J=3.1 Hz), 7.15 (dd, 1 H, J=9.1, 3.1 Hz), 7.03 (d, 1 H, J=9.1 Hz), 6.59 (m, 1 H), 6.56 (m, 1 H), 6.47 (t, 1 H, J=2.1 Hz), 4.20 (t, 2 H, J=6.1 Hz), 3.97 (s, 3 H), 3.76 (s, 3 H), 2.86 (td, 2 H, J=6.1, 1.4 Hz), and 2.25 (s, 3 H).

d) 2-[2-[3-(2,5-Dimethoxyphenylsulfonyloxy)-5-methylphenoxy]ethyl-1-methylene]hydrazinecarboximidamide nitrate To 200 mg (0.526 mmol) of 3-[3-(2,5-dimethoxyphenylsulfonyloxy)-5-methylphenoxy]propionaldehyde, as prepared in the preceding step, in 4.0 mL of absolute ethanol was added 144 mg (1.05 mmol) of aminoguanidine nitrate and the mixture stirred at ambient temperature for 48 h. The mixture was diluted slowly with 20 mL of water, stirred for 10 min and filtered washing with 2 mL of cold water. The solid was air-dried under suction followed by high vacuum to afford 228 mg (87%) of the title compound as a white solid: $^1$H-NMR (300 MHz; DMSO-$d_6$) δ 7.54 (t, 1 H, J=5.0 Hz), 7.45 (br s, 3 H), 7.34 (m, 2 H), 7.17 (d, 1 H, J=2.7Hz), 6.73 (s, 1 H), 6.50 (s, 1 H), 6.45 (t, 1 H, J=2.1 Hz), 4.15 (t, 2 H, J=6.4 Hz), 3.93 (s, 3 H), 3.73 (s, 3 H), 2.68 (dd, 2 H, J=11.2, 6.2 Hz) and 2.22 (s, 3 H). Mass spectrum (MALDI-TOF, α-cyano-4-hydroxycinnamic acid matrix) calcd. for $C_{19}H_{24}N_4O_6S$: 437.1 (M+H). Found: 437.3.

EXAMPLE 17

2-[2-[3-(2,5-Dimethylphenylsulfonyloxy)-5-methylphenoxy]ethyl-1-methylene]hydrazinecarboximidamide nitrate a) 3-(2,5-Dimethylphenylsulfonyloxy)-5-methylphenol Orcinol monohydrate (1.42 g, 10.0 mmol) and 2,5-dimethylbenzenesulfonyl chloride (2.05 g, 10.0 mmol) were mixed in saturated aqueous $NaHCO_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over $Na_2SO_4$. After removing the solvent in vacuo, the residue was purified by flash column chromatography (dichloromethane to 2% ethyl acetate in dichloromethane) to give the title compound as a pale yellow oil (2.10 g, 72%). $^1$H-NMR (300 MHz, $CDCl_3$) δ 7.65 (s, 1H), 7.29 (m, 1H), 7.25 (m, 1H), 6.50 (s, 1H), 6.38 (s, 1H), 6.30 (s, 1H), 5.27 (br s, 1H), 2.30 (s, 3H), 2.18 (s, 3H), 2.03 (s, 3H).

b) 3-[3-(2,5-Dimethylphenylsulfonyloxy)-5-methylphenoxy]propanol

To a solution of 3-(2,5-dimethylphenylsulfonyloxy)-5-methylphenol (585 mg, 2.0 mmol), as prepared in the preceding step, tri-n-butylphosphine (607 mg, 3.0 mmol) and 1,3-propanediol (760 mg, 10 mmol) in anhydrous tetrahydrofuran (20 mL) was added 1,1'-(azodicarbonyl)dipiperidine (757 mg, 3.0 mmol). The mixture was stirred at ambient temperature overnight. Hexane (30 mL) was added to the mixture, and the precipitates were removed by filtration. The filtrate was evaporated in vacuo, and the residue was purified by flash column chromatography (1:1 hexane/ethyl acetate) to give the title compound as a pale yellow oil (650 mg, 93%). $^1$H-NMR (300 MHz, $CDCl_3$) δ 7.69 (s, 1H), 7.34 (d, J=8.0 Hz, 1H), 7.29 (s, 1H), 6.60 (s, 1H), 6.43 (s, 1H), 6.37 (s, 1H), 3.99 (t, J=6.0 Hz, 2H), 3.81 (m, 2), 2.70 (s, 3H), 2.33 (s, 3H), 2.24 (s, 3H), 1.98 (m, 2H), 1.63 (s, 1H).

c) 3-[3-(2,5-Dimethylphenylsulfonyloxy)-5-methylphenoxy]propionaldehyde

Sulfur trioxide pyridine complex (800 mg, 5.0 mmol) was added to a solution of 3-[3-(2,5-dimethylphenylsulfonyloxy)-5-methylphenoxy]propanol (600 mg, 1.7 mmol), as prepared in the preceding step, N,N-diisopropylethylamine (0.7 mL, 5.5 mmol) and anhydrous dimethyl sulfoxide (0.4 mL, 5.6 mmol) in anhydrous dichloromethane (20 mL). The reaction mixture was stirred at ambient temperature for 1 hour and then quenched with 10% aqueous citric acid (60 mL). The mixture was extracted into dichloromethane (3×50 mL), and the dichloromethane solution was washed with 10% aqueous citric acid (40 mL) and dried over $Na_2SO_4$. After removing the solvent in vacuo, the residue was purified by flash column chromatography (dichloromethane) to give the title compound as a colorless oil (530 mg, 89%). $^1$H-NMR (300 MHz, $CDCl_3$) δ 9.82 (s, 1H), 7.68 (s, 1H), 7.33 (d, J=7.8 Hz, 1H), 7.29 (s, 1H), 6.60 (s, 1H), 6.45 (s, 1H), 6.35 (s, 1H), 4.17 (t, J=6.1 Hz, 2H), 2.85 (t, J=6.1 Hz, 2H), 2.70 (s, 3H), 2.33 (s, 3H), 2.24 (s, 3H).

d) 2-[2-[3-(2,5-Dimethylphenylsulfonyloxy)-5-methylphenoxy]ethyl-1-methylene]hydrazinecarboximidamide nitrate A solution of 3-[3-(2,5-dimethylphenylsulfonyloxy)-5-methylphenoxy]propionaldehyde (520 mg, 1.5 mmol), as prepared in the preceding step, and aminoguanidine nitrate (410 mg, 3.0 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (560 mg, 80%). $^1$H-NMR (300 MHz, DMSO-$d_6$) δ 11.21 (br s, 1H), 7.62 (s, 1H), 7.45–7.55 (m, 8 H), 6.75 (s, 1H), 6.45 (s, 1H), 6.40 (s, 1H), 4.13 (t, J=6.2 Hz, 2H), 2.67 (t, J=6.2 Hz, 2H), 2.63 (s, 3H), 2.31 (s, 3H), 2.21 (s, 3H). Mass spectrum (MALDI-TOF, α-cyano-4-hydroxycinnamic acid matrix) calcd. for $C_{19}H_{24}N_4O_4S$: 405.1 (M+H), 427.0 (M+Na). Found: 405.0, 427.1.

EXAMPLE 18

2-[2-[3-(5-Chloro-2-methoxyphenylsulfonyloxy)-5-methylphenoxy]ethyl-1-methylene]hydrazinecarboximidamide hydrochloride a) 3-[3-(5-Chloro-2-methoxyphenylsulfonyloxy)-5-methylphenoxy]propanol Tri-n-butylphosphine (7.6 mL, 30.4 mmol) was added dropwise over 20 min to 3-(5-chloro-2-methoxyphenylsulfonyloxy)-5-methylphenol (5.00 g, 15.2 mmol, as prepared in step a of example 8), 1,3-propanediol (3.3 mL, 45.6 mmol) and 1,1'-(azodicarbonyl)dipiperidine (7.68 g, 30.4 mmol) in anhydrous tetrahydrofuran (80 mL) at 0° C. under a nitrogen atmosphere. Dichloromethane (150 mL) was added mid-way through the tri-n-butylphosphine addition to aid stirring. The slurry was stirred for an additional 5 min at 0° C. then at ambient temperature for 3 h. Diethyl ether (400 mL) was added, and the mixture was stirred for 10 min then filtered. The filtrate was concentrated and the product was purified by flash column chromatography (25% to 60% ethyl acetate in hexane) to give the title compound (4.07 g, 69%) as a gold oil. $^1$H-NMR (300 MHz, CDCl$_3$) δ 7.82 (d, 1 H, J=2.8 Hz), 7.56 (dd, 1 H, J=2.6, 8.9 Hz), 7.03 (d, 1 H, J=8.9 Hz), 6.62 (br s, 1 H), 6.52 (br s, 1 H), 6.47 (t, 1 H, J=2.3 Hz), 4.03 (t, 2 H, J=6 Hz), 4.01 (s, 3 H), 3.80–3.85 (m, 2 H), 2.26 (s, 3 H), 2.00 (pentet, 2H, J=6 Hz), 1.64 (t, 1 H, J=5 Hz). Mass spectrun (MALDI-TOF, α-cyano-4-hydroxycinnamic acid matrix) calcd. for C$_{17}$H$_{19}$ClO$_6$S: 409.0 (M+Na). Found: 409.0.

b) 3-[3-(5-Chloro-2-methoxyphenylsulfonyloxy)-5-methylphenoxy]propionaldehyde

To a cooled (0° C.) solution of 3-[3-(5-chloro-2-methoxyphenylsulfonyloxy)-5-methylphenoxy]propanol (3.32 g, 8.58 mmol), N,N-diisopropylethylamine (3.14 mL, 18.0 mmol), and anhydrous dimethyl sulfoxide (1.83 mL, 25.7 mmol) in anhydrous dichloromethane (20 mL) under nitrogen was added sulfur trioxide pyridine complex (2.73 g, 17.1 mmol) portionwise over 23 minutes. The solution was stirred at 0° C. for 1 hour then quenched with 5% w/v aqueous citric acid (200 mL, 48 mmol). The mixture was extracted with diethyl ether (250 mL). The aqueous layer was extracted with diethyl ether (2×100 mL), and the combined organic extracts were washed with pH 7 buffer (100 mL) and brine (100 mL). The organic layer was dried over Na$_2$SO$_4$, filtered, and evaporated. Crude product was purified by flash column chromatography through silica gel (50% to 70% diethyl ether in hexane) to give the title compound as a gold oil (2.34 g, 71%). $^1$H-NMR (300 MHz, CDCl$_3$) δ 9.81 (t, 1 H, J=1.5 Hz), 7.79 (d, 1 H, J=2.7 Hz), 7.54 (dd, 1 H, J=2.7, 8.9 Hz), 7.01 (d, 1 H, J=8.9 Hz), 6.54–6.60 (m, 1 H), 6.52–6.53 (m, 1 H), 6.43–6.44 (m, 1 H), 4.19 (t, 2 H, J=6.1 Hz), 3.99 (s, 3 H), 2.85 (td, 2 H, J=1.5, 6.1 Hz), 2.25 (d, 3 H, J=0.5 Hz). Mass spectrum (MALDI-TOF, α-cyano4- hydroxycinnamic acid matrix) calcd. for C$_{17}$H$_{17}$ClO$_6$S: 407.0 (M+Na). Found: 407.0.

c) 2-[2-[3-(5-Chloro-2-methoxyphenylsulfonyloxy)-5-methylphenoxy]ethyl-1-methylene]hydrazinecarboximidamide hydrochloride A mixture of 3-[3-(5-chloro-2-methoxyphenylsulfonyloxy)-5-methylphenoxy]propionaldehyde (1.83 g, 4.77 mmol, as prepared in the preceding step), aminoguanidine nitrate (1.31 g, 9.57 mmol) and ethanol (39 mL) was stirred for 2 days at ambient temperature. Water (70 mL) was added dropwise, and the nitrate salt of the title compound was isolated by filtration as a white solid (1.74 g, 72%). The nitrate salt (0.892 g) was converted to the free base by mixing with dichloromethane (25 mL) and basic water (25 mL of 0.4N NaOH). The aqueous layer was extracted with dichloromethane (2×25 mL). The combined organic layers were washed with brine (75 mL) and dried over K$_2$CO$_3$. The mixture was filtered, and the filtrate was concentrated to give the free base of the title compound as a white foam. The free base was dissolved in methanol and added dropwise to ethanolic HCl (2.9 ml of 1.1M HCl in ethanol) in diethyl ether (250 mL). The mixture was concentrated in vacuo. The residue was dissolved in warm 2-propanol (6 mL at 55° C.) and added dropwise to anhydrous diethyl ether (400 mL). The title compound was isolated by filtration as a gummy solid which turned to an off-white foam under high vacuum (0.45 g). $^1$H-NMR (300 MHz, DMSO-d$_6$) δ 7.86 (dd, 1 H, J=2.7, 9.0 Hz), 7.65 (d, 1 H, J=2.7 Hz), 7.55 (t, 1 H, J=5.0 Hz), 7.43 (d, H, J=9.0 Hz), 6.76 (br s, 1 H), 6.50 (br s, 1 H), 6.46 (t, 1 H,J=2Hz),4.16 (t,2H, J=6.4 Hz),4.01 (s, 3 H), 2.65–2.71 (m, 2 H), 2.23 (s, 3 H). Mass spectrum (MALDI-TOF, α-cyano-4-hydroxycinnamic acid matrix) calcd. for C$_{18}$H$_{21}$ClN$_4$O$_5$S: 441.1 (M+H), 463.1 (M+Na). Found: 441.2, 463.4.

EXAMPLE 19

2-[2-[3-(5-Chlorothiophenyl-2-sulfonyloxy)-5-methylphenoxylethy]-1-methylene] hydrazinecarboximidamide nitrate a) 3-(5-Chlorothiophenyl-2-sulfonyloxy)-5-methylphenol A mixture of orcinol monohydrate (5.0 g, 35.2 mmol) and 5-chlorothiophene-2-sulfonyl chloride (7.64 g, 35.2 mol) in 50 mL of saturated aqueous sodium bicarbonate, 50 mL of diethyl ether, and 15 mL of tetrahydrofuran was stirred at 60° C. for 2 h and then at 40° C. overnight. The reaction mixture was extracted into diethyl ether, dried (MgSO$_4$), and passed through a thick pad of silica gel (ca. 500 mL) using elutions of dichloromethane and then 3% diethyl ether/dichloromethane to provide 5.49 g (51%) of the title compound as a pale orange oil. $^1$H-NMR (300 MHz, CDCl$_3$) δ 7.40 (d, 1H, J=4 Hz), 6.94 (d, 1H, J=4 Hz), 6.59 (br s, 1H), 6.49 (br s, 1H), 6.40 (t, 1H, J=2 Hz), 5.38 (s, 1H), 2.26 (3H). Mass spectrum (MALDI-TOF gentisic acid matrix) calcd. for C$_{11}$H$_9$ClO$_4$S$_2$ 327.0 (M+Na). Found: 327.0.

b) 3-[3-(5-Chlorothiophenyl-2-sulfonyloxy)-5-methylphenoxy]propanol

Tri-n-butylphosphine (6.1 mL, 24 mmol) was added dropwise over 5 min to 3-(5-chlorothiophenyl-2-sulfonyloxy)-5-methylphenol (3.49 g, 11.5 mmol, as prepared in the preceding step), 1,3-propanediol (2.2 mL, 30 mmol) and 1,1'-(azodicarbonyl)dipiperidine (6.16 g, 24 mmol) in anhydrous tetrahydrofuran (45 mL) at 0° C. under a nitrogen atmosphere. Dichloromethane (70 mL) and additional tetrahydrofuran (10 mL) were added mid-way through the tri-n-butylphosphine addition to aid stirring. The slurry was stirred at ambient temperature for 2.5 h, then diethyl ether (300 mL) was added and the mixture was filtered. The filtrate was concentrated and the residue was purified by flash column chromatography (25% to 40% ethyl acetate in hexane) to give the title compound (3.11 g, 75%) as a gold oil. $^1$H-NMR (300 MHz, CDCl$_3$) δ 7.41 (d, 1H, J=4.1 Hz), 6.95 (d, 1H, J=4.1 Hz), 6.66 (br s, 1H), 6.50 (br s, 1H), 6.45 (t, 1H, J=2.2 Hz), 4.04 (t, 1H, J=6.0 Hz), 3.83 (t, 2H, J=6.0 Hz), 2.28 (s, 3 H), 2.01 (pentet, 2H, J=6.0 Hz). Mass spectrum (MALDI-TOF, gentisic acid matrix) calcd. for C$_{14}$H$_{15}$ClO$_5$S$_2$: 385.0 (M+Na). Found: 385.1.

c) 3-[3-(5-Chlorothiophenyl-2-sulfonyloxy)-5-methylphenoxy]propionaldehyde

To 3-[3-(5-chlorothiophenyl-2-sulfonyloxy)-5-methylphenoxy]propanol (1.77 g, 4.88 mmol, as prepared in the preceding step) in anhydrous dichloromethane (30 mL) containing anhydrous dimethyl sulfoxide (760 μL, 9.08 mmol) and N,N-diisopropylethylamine (4 mL, 23 mmol) at 0° C. was added slowly sulfur trioxide pyridine complex (1.55 g, 9.8 mmol). The reaction mixture was stirred for 20 min, quenched with excess 5% aqueous citric acid (acidic to pH paper), and extracted into diethyl ether. The organic phase was washed with additional 5% aqueous citric acid, dried (MgSO$_4$), and purified by flash chromatography (dichloromethane to 3% diethyl ether in dichloromethane) to give 1.13 g of the title compound as an oil. $^1$H-NMR (300 MHz, CDCl$_3$) δ 9.84 (t, 1H, J=1 Hz), 7.40 (d, 1H, J=4 Hz), 6.95 (d, 1H, J=4 Hz), 6.65 (br s, 1H), 6.51 (br s, 1H),6.44 (t, 1H, J=2 Hz), 4.22 (t, 2H, J=6 Hz), 2.89 (td, 2H, J=1, 6 Hz), 2.28 (s, 3H). Mass spectrum (MALDI-TOF, α-cyano-4- hydroxycinnamic acid matrix) calcd. for $C_{14}H_{13}ClO_5S_2$: 383.0 (M+Na). Found: 382.9.

d) 2-[2-[3-(5-Chlorothiophenyl-2-sulfonyloxy)-5-methylphenoxy]-ethyl-1-methylene] hydrazinecarboximidamide nitrate A mixture of 3-[3-(5-chlorothiophenyl-2-sulfonyloxy)-5-methylphenoxy] propionaldehyde (1.60 g, 4.4 mmol, as prepared in the preceding step) and aminoguanidine nitrate (0.73 g, 0.53 mmol) in ethanol (15 mL) was stirred overnight at ambient temperature. Water (25 mL) was added dropwise over 15 min. The mixture was stirred for 30 min and then filtered to give the title compound (1.75 g, 87%) as a white solid. $^1$H-NMR (300 MHz, DMSO-d$_6$) δ 7.76 (d, 1H, J=4.2 Hz), 7.55 (t, 1H, J=5.0 Hz), 7.40 (d, 1H, J=4.2 Hz), 6.81 (br s, 1H), 6.55 (br s, 1H), 6.52 (t, 1H, J=2.2 Hz), 4.17 (t, 2H, J=6.4 Hz), 2.70 (m, 2H), 2.26 (s, 3H). Mass spectrum (MALDI-TOF, α-cyano-4-hydroxycinnamic acid matrix) calcd. for $C_{15}H_{17}ClN_4O_4S_2$: 417.0 (M+H). Found: 416.5.

EXAMPLE 20

2-[2-[3-(5-Chloro-1,3-dimethylpyrazole-4-sulfonyloxy)-5-methylphenoxy]-ethyl-1-methylene] hydrazinecarboximidamide acetate a) 3-(5-Chloro-1,3-Dimethylpyrazole-4-sulfonyloxy)-5-methylphenol A mixture of orcinol monohydrate (650 mg, 4.58 mmol) and 1.03 g (4.50 mmol) of 5-chloro-1,3-dimethylpyrazole-4-sulfonyl chloride in diethyl ether (20 mL) and saturated aqueous sodium bicarbonate (20 mL) was stirred overnight. To the reaction mixture was added 15 mL of tetrahydrofuran, and the reaction mixture was heated to 50° C. for 1 h and at 70° C. for 1 h. The reaction mixture was cooled to room temperature, extracted into ethyl acetate, dried (MgSO$_4$), and purified by flash chromatography (dichloromethane/diethyl ether (100:0 to 95:5 to 93:7)) to give the title compound (558 mg, 37% yield) as an oil. $^1$H-NMR (300 MHz, CDCl$_3$) δ 6.91–6.92 (m, 1H), 6.57–6.61 (m, 1H), 6.41–6.50 (m, 1H), 5.93 (s, 1H), 3.82 (s, 3H), 2.29 (s, 3H), 2.25 (s, 3H). Mass spectrum (MALDI-TOF, α-cyano-4-hydroxycinnamic acid matrix) calcd. for $C_{12}H_{13}ClN_2O_4S$: 316.9 (M+H). Found: 317.0.

b) 3-[3-(5-Chloro-1,3-dimethylpyrazole-4-sulfonyloxy)-5-methylphenoxy]propanol

To a solution of 318 mg (0.951 mmol) of 3-(5-chloro-1,3-dimethyl-pyrazole-4-sulfonyloxy)-5-methylphenol, as prepared in the preceding step, in 5 mL of anhydrous tetrahydrofuran containing 360 mg (1.42 mmol) of 1,1'-(azodicarbonyl)dipiperidine and 150 μL (2.07 mmol) of 1,3-propanediol was added slowly 350 μL (1.41 mmol) of tri-n-butylphosphine. The reaction mixture was stirred for 1 h at ambient temperature, diluted with diethyl ether, and filtered. The filtrate was concentrated and purified by flash chromatography (ethyl acetate/dichloromethane (2:1)) to give 227 mg (64% yield) of the title compound as an oil. $^1$H-NMR (300 MHz, CDCl$_3$) δ 6.64–6.65 (m, 1H), 6.52–6.54 (m, 1H), 6.46–6.47 (t, 1H), 4.06 (t, 2H, J=6 Hz), 3.83 (t, 2H, J=6 Hz), 3.82 (s, 3H), 2.29 (s, 3H), 2.28 (s, 3H), 2.00 (pentet, 2H, J=6 Hz). Mass spectrum (MALDI-TOF, α-cyano-4-hydroxycinnamic acid matrix) calcd. for $C_{15}H_{19}ClN_2O_5S$: 375.1 (M+H), 397.1 (M+Na). Found: 374.9, 397.1.

c) 3-[3-(5-Chloro-1,3-dimethylpyrazole-4-sulfonyloxy)-5-methylphenoxy]propionaldehyde To 227 mg (0.660 mmol) of 3-[3-(5-chloro-1,3-dimethyl-pyrazole-4-sulfonyloxy)-5-methylphenoxy]propanol, as prepared in the preceding step, in dichloromethane (2 mL) containing 61 μL (0.79 mmol) of anhydrous dimethyl sulfoxide and 275 μL (1.58 mmol) of N,N-diisopropylethylamine was added 124 mg (0.78 mmol) of sulfur trioxide pyridine complex. The reaction mixture was stirred at ambient temperature for 60 min and then purified by flash chromatography (dichloromethane then 20% ethyl acetate/dichloromethane) to give 75 mg of the title compound as an unstable oil. TLC clearly showed 3-(5-chloro-1,3-dimethylpyrazole-4-sulfonyloxy)-5-methylphenol as the major byproduct. $^1$H-NMR (300 MHz, CDCl$_3$) δ 9.85 (t, 1H, J=1.5 Hz), 6.64 (s, 1H), 6.51–6.57 (m, 2H), 6.46 (t, 1H, J=2 Hz), 6.42 (t, 1H, J=2 Hz), 4.23 (t, 2H, J=6 Hz), 3.82 (s, 3H), 2.89 (td, 2H, J=1, 6 Hz), 2.29 (s, 3H), 2.26 (s, 3H).

d) 2-[2-[3-(5-Chloro-1,3-dimethylpyrazole-4-sulfonyloxy)-5-methylphenoxy]ethyl-1-methylene] hydrazinecarboximidamideacetate To all of 3-[3-(5-chloro-1,3-dimethylpyrazole-4-sulfonyloxy)-5-methylphenoxy]propionaldehyde, as prepared in the preceding step, in ethanol (1 mL) was added 56 mg (0.41 mmol) of aminoguanidine nitrate. The reaction mixture was stirred at ambient temperature for 2 days. The reaction mixture was treated with 250 μL (0.5 mmol) of 2.5N NaOH, extracted into dichloromethane, dried (MgSO$_4$), and concentrated. The residue was treated with 300 μL of glacial acetic acid and concentrated. The residue was purified by flash chromatography (dichloromethane/methanol/glacial acetic acid (95:3.5:1.5)) to give 26.9 mg of the title compound as a solid. $^1$H-NMR (300 MHz, DMSO-d$_6$) δ 7.40 (t, 1H, J=5 Hz), 6.79 (s, 1H), 6.52 (s, 1H), 6.44 (t, 1H, J=2 Hz), 4.10 (t, 2H, J=6 Hz), 3.80 (s, 3H), 2.73 (q, 2H, J=6 Hz), 2.25 (s, 3H), 2.13 (s, 3H), 1.79 (s, 3H). Mass spectrum (MALDI-TOF, α-cyano-4-hydroxycinnamic acid matrix) calcd. for $C_{16}H_{21}ClN_6O_4S$: 429.1 (M+H), 451.1 (M+Na). Found: 429.1, 451.1.

EXAMPLE 21

2-[2-[3-(3-Chlorophenylsulfonyloxy)-5-methylphenoxy]ethyl-1-methylene]-hydrazinecarboximidamide nitrate a) 3-(3-Chlorophenylsulfonyloxy)-5-methylphenol Orcinol monohydrate (1.42 g, 10.0 mmol) and 3-chlorobenzenesulfonyl chloride (2.21 g, 10.0 mmol) were mixed in saturated aqueous NaHCO$_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over Na$_2$SO$_4$. After removing the solvent in vacuo, the residue was purified by flash column chromatography (dichloromethane to 2% ethyl acetate in dichloromethane) to give the title compound as a pale yellow oil (2.08 g, 69%). $^1$H-NMR (300 MHz, CDCl$_3$) δ 7.86 (s, 1H), 7.74 (d, J=7.8 Hz, 1H), 7.64 (d, J=8.0 Hz, 1H), 7.48 (t, J=8.0 Hz, 1H), 6.57 (s, 1H), 6.40 (s, 1H), 6.33 (s, 1H), 5.32 (s, 1H), 2.24 (s, 3H).

b) 3-[3-(3-Chlorophenylsulfonyloxy)-5-methylphenoxy] propanol

To a solution of 3-(3-chlorophenylsulfonyloxy)-5-methylphenol (450 mg, 1.5 mmol), as prepared in the preceding step, tri-n-butylphosphine (607 mg, 3.0 mmol) and 1,3-propanediol (760 mg, 10 mmol) in anhydrous tetrahydrofuran (20 mL) was added 1,1'-(azodicarbonyl) dipiperidine (757 mg, 3.0 mmol). The mixture was stirred at ambient temperature overnight. Hexane (30 mL) was added to the mixture, and the precipitates were removed by filtration. The filtrate was evaporated in vacuo, and the residue was purified by flash column chromatography (1:1 hexane/ethyl acetate) to give the title compound as a colorless oil (480 mg, 90%). $^1$H-NMR (300 MHz, CDCl$_3$) δ 7.86 (s, 1H), 7.74 (d, J=7.8 Hz, 1H), 7.64 (d, J=8.1 Hz, 1H), 7.49 (t, J=8.0 Hz, 1H), 6.64 (s, 1H), 6.41 (s, 1H), 6.37 (s, 1H), 4.01 (t, J=6.0 Hz, 2H), 3.82 (t, J=6.0 Hz, 2H), 2.25 (s, 3H), 1.99 (m, 2H), 1.65 (br s, 1H).

c) 3-[3-(3-Chlorophenylsulfonyloxy)-5-methylphenoxy]propionaldehyde

Sulfur trioxide pyridine complex (480 mg, 4.0 mmol) was added to a solution of 3-[3-(2,3-dichlorophenylsulfonyloxy)-5-methylphenoxy]propanol (460 mg, 1.3 mmol), as prepared in the preceding step, N,N-diisopropylethylamine (0.5 mL, 3.9 mmol) and anhydrous dimethyl sulfoxide (0.3 mL, 4.2 mmol) in anhydrous dichloromethane (10 mL). The reaction mixture was stirred at ambient temperature for 1 hour and then quenched with 10% aqueous citric acid (50 mL). The mixture was extracted into dichloromethane (3×50 mL), and the dichloromethane solution was washed with 10% aqueous citric acid (40 mL) and dried over Na$_2$SO$_4$. After removing the solvent in vacuo, the residue was purified by flash column chromatography (dichloromethane) to give the title compound as a colorless oil (420 mg, 91%). $^1$H-NMR (300 MHz, CDCl$_3$) δ 9.84 (s, 1H), 7.86 (s, 1H), 7.74 (d, J=7.9 Hz, 1H), 7.64 (d, J=8.0 Hz, 1H), 7.49 (t, J=8.0 Hz, 1H), 6.63 (s, 1H), 6.44 (s, 1H), 6.37 (s, 1H), 4.20 (t, J=6.1 Hz, 2H), 2.87 (t, J=6.1 Hz, 2H), 2.26 (s, 3H).

d) 2-[2-[3-(3-Chlorophenylsulfonyloxy)-5-methylphenoxy]ethyl-1-methylene]hydrazinecarboximidamide nitrate A solution of 3-[3-(3-chlorophenylsulfonyloxy)-5-methylphenoxy]-propionaldehyde (390 mg, 1.1 mmol), as prepared in the preceding step, and aminoguanidine nitrate (343 mg, 2.5 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (370 mg, 69%). $^1$H-NMR (300 MHz, DMSO-d$_6$) δ 11.21 (br s, 1H), 7.93 (s, 2H), 7.86 (d, J=7.9 Hz, 1H), 7.71 (t, J=8.1 Hz, 1H), 7.54 (t, J=5.0 Hz, 1H), 7.52 (br s, 4H), 6.78 (s, 1H), 6.49 (s, 2H), 4.15 (t, J=6.1 Hz, 2H), 2.69 (m, 2H), 2.23 (s, 3H). Mass spectrum (MALDI-TOF, α-cyano-4-hydroxycinnamic acid matrix) calcd. for C$_{17}$H$_{19}$ClN$_4$O$_4$S: 411.1 (M+H), 433.1 (M+Na). Found: 410.8, 433.0.

EXAMPLE 22

2-[2-[5-Methyl-3-(2-methyl-5-nitrophenylsulfonyloxy)phenoxy]ethyl-1-methylene]hydrazinecarboximidamide nitrate a) 5-Methyl-3-(2-methyl-5-nitrophenylsulfonyloxy)phenol Orcinol monohydrate (2.84 g, 20.0 mmol) and 2-methyl-5-nitrobenzenesulfonyl chloride (4.71 g, 20.0 mmol) were mixed in saturated aqueous NaHCO$_3$ (60 mL) and diethyl ether (60 mL). The biphasic mixture was stirred vigorously at ambient temperature overnight. The reaction mixture was diluted with water (100 mL) and extracted into ethyl acetate (3×60 mL). The organic phase was washed with brine (2×50 mL) and dried over Na$_2$SO$_4$. After removing the solvent in vacuo, the residue was purified by flash column chromatography (dichloromethane to 5% ethyl acetate in dichloromethane) to give the title compound as a pale yellow solid (4.20 g, 72%). $^1$H-NMR (300 MHz, CDCl$_3$) δ 8.71 (s, 1H), 8.37 (d, J=8.4 Hz, 1H), 7.62 (d, J=8.4 Hz, 1H), 6.56 (s, 1H), 6.44 (s, 1H), 6.33 (s, 1H), 5.42 (s, 1H), 2.91 (s, 3H), 2.23 (s, 3H).

b) 3-[5-Methyl-3-(2-methyl-5-nitrophenylsulfonyloxy)phenoxy]propanol

To a solution of 5-methyl-3-(2-methyl-5-nitrophenylsulfonyloxy)phenol (1.46 g, 5.0 mmol), as prepared in the preceding step, tri-n-butylphosphine (1.6 g, 8.0 mmol) and 1,3-propanediol (2.3 g, 30 mmol) in anhydrous tetrahydrofuran (50 mL) was added 1,1'-(azodicarbonyl)dipiperidine (2.0 g, 8.0 mmol). The mixture was stirred at ambient temperature overnight. Hexane (80 mL) was added to the mixture, and the precipitates were removed by filtration. The filtrate was evaporated in vacuo, and the residue was purified by flash column chromatography (1:1 hexane/ethyl acetate) to give the title compound as a yellow oil (920 mg, 48%). $^1$H-NMR (300 MHz, CDCl$_3$) δ 8.72 (s, 1H), 8.37 (d, J=8.3 Hz, 1H), 7.62 (d, J=8.4 Hz, 1H), 6.63 (s, 1H), 6.43 (s, 1H), 6.40 (s, 1H), 4.02 (t, J=6.0 Hz, 2H), 3.81 (t, J=6.0 Hz, 2H), 2.89 (s, 3H), 2.25 (s, 3H), 1.99 (m, 2H), 1.58 (s, 1H).

c) 3-[5-Methyl-3-(2-methyl-5-nitrophenylsulfonyloxy)phenoxy]propionaldehyde

Sulfur trioxide pyridine complex (960 mg, 6.0 mmol) was added to a solution of 3-[5-methyl-3-(2-methyl-5-nitrophenylsulfonyloxy)phenoxy]propanol (760 mg, 2.0 mmol), as prepared in the preceding step, N,N-diisopropylethylamine (0.7 mL, 5.5 mmol) and anhydrous dimethyl sulfoxide (0.4 mL, 5.6 mmol) in anhydrous dichloromethane (20 mL). The reaction mixture was stirred at ambient temperature for 1 hour and then quenched with 10% aqueous citric acid (70 mL). The mixture was extracted into dichloromethane (3×50 mL), and the dichloromethane solution was washed with 10% aqueous citric acid (40 mL) and dried over Na$_2$SO$_4$. After removing the solvent in vacuo, the residue was purified by flash column chromatography (dichloromethane) to give the title compound as a colorless oil (590 mg, 78%). $^1$H-NMR (300 MHz, CDCl$_3$) δ 9.83 (s, 1H), 8.72 (s, 1H), 8.38 (d, J=8.4 Hz, 1H), 7.63 (d, J=8.4 Hz, 1H), 6.63 (s, 1H), 6.46 (s, 1H), 6.39 (s, 1H), 4.21 (t, J=6.0 Hz, 2H), 2.89 (s, 3H), 2.87 (t, J=6.0 Hz, 2H), 2.26 (s, 3H).

d) 2-[2-[5-Methyl-3-(2-methyl-5-nitrophenylsulfonyloxy)phenoxy]ethyl-1-methylene]hydrazinecarboximidamide nitrate A solution of 3-[5-methyl-3-(2-methyl-5-nitrophenylsulfonyloxy)-phenoxy]propionaldehyde (570 mg, 1.5 mmol), as prepared in the preceding step, and aminoguanidine nitrate (410 mg, 3.0 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (640 mg, 85%). $^1$H-NMR (300 MHz, DMSO-d$_6$) δ 8.54 (d, J=8.4 Hz, 1H), 8.43 (s, 1H), 7.91 (d, J=8.4 Hz, 1H), 7.54 (t, J=5.0 Hz, 1H), 7.46 (br s, 4H), 6.79 (s, 1H), 6.52 (s, 1H), 6.49 (s, 1H), 4.15 (t, J=6.0 Hz, 2H), 2.81 (s, 3H), 2.68 (m, 2H), 2.21 (s, 3H). Mass spectrum (MALDI-TOF, α-cyano-4-hydroxycinnamic acid matrix) calcd. for C$_{18}$H$_{21}$N$_5$O$_6$S: 436.1 (M+H), 458.1 (M+Na). Found: 436.2, 458.2.

EXAMPLE 23

2-[3-[3-(2-Methoxyphenylsulfonyloxy)-5-methylphenoxy]propyl-1-methylene]hydrazinecarboximidamide nitrate a) 4-[3-(2-Methoxyphenylsulfonyloxy)-5-methylphenoxy]butanol A solution of 3-(2-methoxyphenylsulfonyloxy)-5-methylphenol (177 mg, 0.60 mmol, as prepared in step b of example 8), 1,4-butanediol (0.53 mL, 6.0 mmol), triphenylphosphine (316 mg, 1.2 mmol), and anhydrous tetrahydrofuran (4 mL) was cooled to 0° C., then diethyl azodicarboxylate (0.20 mL, 1.2 mmol) was added dropwise over 5 minutes. The solution was stirred at 0° C. for 15 min and then at ambient temperature overnight. Additional triphenylphosphine (3×320 mg) and diethyl azodicarboxylate (3×0.20 mL) were added over the next 3 days. The mixture was filtered, and the filtrate was concentrated. The residue was triturated with 40% ethyl acetate in hexane, then the mixture was filtered and the filtrate was concentrated. Crude product was purified by flash column chromatography through silica gel (40% to 70% ethyl acetate in hexane, then 0% to 2% acetone in dichloromethane in a separate chromatographic separation) to give the title compound as a colorless oil (85.4 mg, 39%). $^1$H-NMR (300 MHz, CDCl$_3$) δ 7.83 (dd, 1H, J=1.8, 7.9 Hz), 7.61 (ddd, 1H, J=1.7, 7.4, 8.4 Hz), 7.08 (d, 1H, J=8 Hz), 6.99–7.04 (m, 1H), 6.57 (br s, 1H), 6.50 (br s, 1H), 6.44 (t, 1H, J=2.2 Hz), 4.02 (s, 3H), 3.88 (t, 2H, J=6.0 Hz), 3.70 (q, 2H, J=6 Hz), 2.24 (s, 3H), 1.65–1.87 (m, 4H), 1.45 (t, 1H, J=6 Hz).

b) 4-[3-(2-Methoxyphenylsulfonyloxy)-5-methylphenoxy]butyraldehyde

A solution of 4-[3-(2-methoxyphenylsulfonyloxy)-5-methylphenoxy]butanol (85.7 mg, 0.23 mmol, as prepared in the preceding step), N,N-diisopropylethylamine (86 uL, 0.49 mmol), anhydrous dimethyl sulfoxide (50 uL, 0.70 mmol) and anhydrous dichloromethane (1 mL) was cooled to 0° C. under nitrogen. Sulfur trioxide pyridine complex was added in portions over 8 minutes. The solution was stirred at 0° C. for 3 hours and at ambient temperature for 1 hour. The reaction was diluted with dichloromethane (25 mL) and extracted with 5% aqueous citric acid (10 mL). The aqueous layer was extracted with dichloromethane (10 mL). The combined organic layers were washed with 5% aqueous citric acid (25 mL), and the aqueous layer was extracted. The combined organic layers were washed with pH 7 buffer (25 mL) and brine (25 mL) and dried over Na$_2$SO$_4$. The mixture was filtered, and the filtrate was concentrated to give the title compound as a colorless oil (86.0 mg, 100%). This product was used in the next step without purification. $^1$H-NMR (300 MHz, CDCl$_3$) δ 9.81 (t, 1H, J=1.3 Hz), 7.82 (dd, 1H, J=1.7, 7.9 Hz), 7.62 (ddd, 1H, J=1.7, 7.4, 8.4 Hz), 7.09 (d, 1H, J=8.4 Hz), 6.99–7.05 (m, 1H), 6.55 (br s, 1H), 6.51 (br s, 1H), 6.42 (t, 1H, J=2 Hz), 4.02 (s, 3H), 3.88 (t, 2H, J=6.0 Hz), 2.62 (td, 2H, J=1.3, 7.0 Hz), 2.24 (s, 3H), 2.01–2.15 (m, 2H). Mass spectrum (MALDI-TOF, α-cyano-4-hydroxycinnamic acid matrix) calcd. for C$_{18}$H$_{20}$O$_6$S: 387.1 (M+Na). Found: 387.0.

c) 2-[3-[3-(2-Methoxyphenylsulfonyloxy)-5-methylphenoxy]propyl-1-methylene]hydrazinecarboximidamide nitrate A mixture of 4-[3-(2-methoxyphenylsulfonyloxy)-5-methylphenoxy]-butyraldehyde (84 mg, 0.23 mmol, as prepared in the preceding step), aminoguanidine nitrate (64 mg, 0.47 mmol) and ethanol (1 mL) was stirred overnight at ambient temperature. Water (5 mL) was added, and the solvent was decanted. The residue was dissolved in ethanol/diethyl ether/hexane, and the solution was concentrated to remove water. The residue was treated with ethanol (2 mL), hexane (10 mL) and diethyl ether (5 mL); the product solidified from the oil. The title compound was isolated by filtration as a white solid (78 mg, 70%). $^1$H-NMR (300 MHz, DMSO-d$_6$) δ 7.76 (ddd, 1H, J=1.7, 7.4, 8.4 Hz), 7.69 (dd, 1H, J=1.7, 7.9 Hz), 7.53 (t, 1H, J=5.0 Hz), 7.37 (d, 1H, J=8 Hz), 7.07–7.12 (m, 1H), 6.68 (br s, 1H), 6.46 (br s, 1H), 6.38 (t, 1H, J=2.1 Hz), 3.99 (s, 3H), 3.90 (t, 2H, J=6.2 Hz), 2.34–2.41 (m, 2H), 2.20 (s, 3H), 1.91 (pentet, 2H, 6 Hz). Mass spectrum (MALDI-TOF, α-cyano-4-hydroxycinnamic acid matrix) calcd. for C$_{19}$H$_{24}$N$_4$O$_5$S: 421.2 (M+H). Found: 421.3.

EXAMPLE 24

2-[2-[3-(5-Fluoro-2-methylphenylsulfonyloxy)-5-methylphenoxy]ethyl-1-methylene]hydrazinecarboximidamide nitrate a) 3-(5-Fluoro-2-methylphenylsulfonyloxy)-5-methylphenol To a solution of 1.00 g (8.05 mmol) of orcinol monohydrate and 1.63 g (7.38 mmol) of 5-fluoro-2-methylbenzenesulfonyl chloride in 20 mL of diethyl ether was added 20 mL of saturated aqueous NaHCO$_3$ and the biphasic mixture stirred vigorously at ambient temperature for 3 days. The layers were separated and the aqueous layer extracted with 2×30 mL of ethyl acetate. The combined organic layers were washed with 50 mL of brine, dried (Na$_2$SO$_4$) and concentrated to give 2.2 g of an orange syrup. Crystallization from dichloromethane-hexane (two crops) afforded 1.24 g (54%) of the title compound as a light orange powder: $^1$H-NMR (300 MHz; CDCl$_3$) δ 7.57 (dd, 1H, J=8.2, 2.8 Hz), 7.36 (dd, 1H, J=8.6, 5.2 Hz), 7.22 (td, 1H, J=8.4, 2.8 Hz), 6.52 (m, 1H), 6.39 (m, 1H), 6.30 (t, 1H, J=2.2 Hz), 2.69 (s, 3H) and 2.21 (s, 3H).

b) 3-[3-(5-Fluoro-2-methylphenylsulfonyloxy)-5-methylphenoxy]propanol

To 458 mg (1.49 mmol) 3-(5-fluoro-2-methylphenylsulfonyloxy)-5-methylphenol, as prepared in the preceding step, 1.08 mL (14.9 mmol) of 1,3-propanediol and 782 mg (2.98 mmol) of triphenylphosphine in 10 mL of anhydrous tetrahydrofuran was added 0.470 mL (2.98 mmol) of diethyl azodicarboxylate dropwise over 15 min. After stirring at ambient temperature for 2 h, the reaction mixture was concentrated to a semisolid. The resulting mixture was flash chromatographed on 50 g of silica gel with 8–10% ethyl acetate-dichloromethane. Impure fractions were re-chromatographed on 40 g of silica gel with 50–100% ethyl acetate-hexane. Material from the two purifications was combined to afford 530 mg (97% yield) of the title compound as a colorless oil: $^1$H-NMR (300 MHz; CDCl$_3$) δ 7.59 (dd, 1H, J=8.3, 2.8 Hz), 7.38 (dd, 1H, J=8.4, 5.3 Hz), 7.25 (td, 1H, J=8.4, 2.8 Hz), 6.62 (m, 1H), 6.1 (m, 1H), 6.37 (t, 1H, J=2.1 Hz), 4.00 (t, 2H, J=6.0 Hz), 3.83 (dd, 2H, J=11.3, 5.8 Hz), 2.73 (s, 3H), 2.24 (s, 3H) and 1.99 (pentet, 2H, J=6.0 Hz). Mass spectrum (MALDI-TOF, α-cyano-4-hydroxycinnamic acid matrix) calcd. for C$_{17}$H$_{19}$FO$_5$S: 377.1 (M+Na). Found: 377.0.

c) 3-[3-(5-Fluoro-2-methylphenylsulfonyloxy)-5-methylphenoxy]propionaldehyde

To a cooled (0° C.), stirred solution of 528 mg (1.44 mmol) of 3-[3-(5-fluoro-2-methylphenylsulfonyloxy)-5-methylphenoxy]propanol, as prepared in the preceding step, 527 μL (3.02 mmol) of N,N-diisopropylethylamine and 307 μL (4.32 mmol) of anhydrous dimethyl sulfoxide in 6.0 mL of anhydrous dichloromethane was added 459 mg (2.88 mmol) of sulfur trioxide pyridine complex. The mixture was warmed to ambient temperature over 30 min and stirred for 16 h. The mixture was then poured into 15 mL of dichloromethane and washed with 5% (w/v) aqueous citric acid (2×25 mL). Each wash was extracted with 5 mL of dichloromethane and the combined extracts were washed with brine (25 mL), dried over Na$_2$SO$_4$ and concentrated. The resulting material was chromatographed on 35 g of silica gel with dichloromethane followed by 3% ethyl acetate-dichloromethane to afford 320 mg (61%) of the title compound as a colorless syrup: Mass spectrum (MALDI-TOF, α-cyano-4-hydroxycinnamic acid matrix) calcd. for C$_{17}$H$_{17}$FO$_5$S: 375.1 (M+Na). Found: 375.0.

d) 2-[2-[3-(5-Fluoro-2-methylphenylsulfonyloxy)-5-methylphenoxy]ethyl-1-methylene] hydrazinecarboximidamide nitrate To 305 mg (0.837 mmol) of 3-[3-(5-fluoro-2-methylphenylsulfonyloxy)-5-methylphenoxy] propionaldehyde, as prepared in the preceding step, in 8.0 mL of absolute ethanol was added 230 mg (1.67 mmol) of aminoguanidine nitrate and the mixture stirred at ambient temperature for three days. The mixture was diluted slowly with 40 mL of water, stirred for 10 min and filtered washing with 5 mL of cold water. The solid was air-dried under suction followed by high vacuum to afford 290 mg (72%) of the title compound as a white solid: $^1$H-NMR (300 MHz; DMSO-d$_6$) δ 11.21 (br s, 1H), 7.64 (m, 3H), 7.54 (t, 1H, J=5.0 Hz), 7.45 (br s, 3H), 6.77 (s, 1H), 6.45 (s, 2H), 4.15 (t, 2H, J=6.4 Hz), 2.68 (dd, 2H, J=11.7, 6.3 Hz), 2.66 (s, 3H) and 2.21 (s, 3H). Mass spectrum (MALDI-TOF, α-cyano-4-hydroxycinnamic acid matrix) calcd. for C$_{18}$H$_{21}$FN$_4$O$_4$S: 409.1 (M+H). Found: 409.1.

EXAMPLE 25

2-[2-[5-Methyl-3-(1-naphthalenylsulfonyloxy) phenoxy]ethyl-1-methylene]-hydrazinecarboximidamide nitrate a) 5-Methyl-3-(1-naphthalenylsulfonyloxy)phenol Orcinol monohydrate (1.42 g, 10.0 mmol) and 1-naphthalenesulfonyl chloride (2.27 g, 10.0 mmol) were mixed in saturated aqueous NaHCO$_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over Na$_2$SO$_4$. After removing the solvent in vacuo, the residue was purified by flash column chromatography (dichloromethane to 3% ethyl acetate in dichloromethane) to give the title compound as a pale yellow oil (2.15 g, 68%). $^1$H-NMR (300 MHz, CDCl$_3$) δ 8.79 (d, J=8.5 Hz, 1H), 8.14 (d, J=7.0 Hz, 2H), 7.98 (d, J=8.4 Hz, 1H), 7.78 (t, J=8.5 Hz, 1H), 7.67 (t, J=8.1 Hz, 1H), 7.49 (t, J=8.0 Hz, 1H), 6.46 (s, 1H), 6.34 (s, 1H), 6.17 (s, 1H), 2.14 (s, 3H).

b) 3-[5-Methyl-3-(1-naphthalenylsulfonyloxy)phenoxy] propanol

To a solution of 5-methyl-3-(1-naphthalenylsulfonyloxy) phenol (620 g, 2.0 mmol), as prepared in the preceding step, tri-n-butylphosphine (607 mg, 3.0 mmol) and 1,3-propanediol (760 mg, 10 mmol) in anhydrous tetrahydrofuran (20 mL) was added 1,1'-(azodicarbonyl)dipiperidine (757 mg, 3.0 mmol). The mixture was stirred at ambient temperature overnight. Hexane (50 mL) was added to the mixture, and the precipitates were removed by filtration. The filtrate was evaporated in vacuo, and the residue was purified by flash column chromatography (1:1 hexane/ethyl acetate) to give the title compound as a yellow oil (650 mg, 87%). $^1$H-NMR (300 MHz, CDCl$_3$) δ 8.80 (d, J=8.6 Hz, 1H), 8.14 (d, J=7.3 Hz, 2H), 7.98 (d, J=8.2 Hz, 1H), 7.78 (t, J=8.5 Hz, 1H), 7.67 (t, J=8.1 Hz, 1H), 7.49 (t, J=8.1 Hz, 1H), 6.54 (s, 1H), 6.33 (s, 1H), 6.22 (s, 1H), 3.84 (t, J=6.0 Hz, 2H), 3.75 (t, J=6.0 Hz, 2H), 2.15 (s, 3H), 1.90 (m, 2H), 1.59 (s, 1H).

c) 3-[5-Methyl-3-(1-naphthalenylsulfonyloxy)phenoxy] propionaldehyde

Sulfur trioxide pyridine complex (800 mg, 5.0 mmol) was added to a solution of 3-[5-methyl-3-(1-naphthalenylsulfonyloxy)phenoxy]propanol (600 mg, 1.6 mmol), as prepared in the preceding step, N,N-diisopropylethylamine (0.7 mL, 5.5 mmol) and anhydrous dimethyl sulfoxide (0.4 mL, 5.6 mmol) in anhydrous dichloromethane (15 mL). The reaction mixture was stirred at ambient temperature for 1 hour and then quenched with 10% aqueous citric acid (60 mL). The mixture was extracted into dichloromethane (3×50 mL), and the dichloromethane solution was washed with 10% aqueous citric acid (40 mL) and dried over Na$_2$SO$_4$. After removing the solvent in vacuo, the residue was purified by flash column chromatography (dichloromethane) to give the title compound as a colorless oil (540 mg, 90%). $^1$H-NMR (300 MHz, CDCl$_3$) δ 9.76 (s, 1H), 8.80 (d, J=8.6 Hz, 1H), 8.14 (d, J=7.7 Hz, 2H), 7.99 (d, J=8.1 Hz, 1H), 7.78 (t, J=8.1 Hz, 1H), 7.67 (t, J=8.1 Hz, 1H), 7.50 (t, J=7.8 Hz, 1H), 6.53 (s, 1H), 6.35 (s, 1H), 6.20 (s, 1H), 4.02 (t, J=6.1 Hz, 2H), 2.76 (t, J=6.1 Hz, 2H), 2.15 (s, 3H).

d) 2-[2-[5-Methyl-3-(1-naphthalenylsulfonyloxy) phenoxy]ethyl-1-methylene] hydrazinecarboximidamide nitrate A solution of 3-[5-methyl-3-(1-naphthalenylsulfonyloxy) phenoxy]-propionaldehyde (520 mg, 1.4 mmol), as prepared in the preceding step, and aminoguanidine nitrate (410 mg, 3.0 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (610 mg, 89%). $^1$H-NMR (300 MHz, DMSO-d$_6$) δ 8.63 (d, J=8.5 Hz, 1H), 8.42 (d, J=8.3 Hz, 1H), 8.21 (d, J=8.2 Hz, 1H), 8.15 (d, J=7.4 Hz, 1H), 7.91 (t, J=8.4 Hz, 1H), 7.79 (t, J=8.1 Hz, 1H), 7.68 (t, J=7.9 Hz, 1H), 7.48 (br m, 5H), 6.69 (s, 1H), 6.30 (s, 1H), 6.23 (s, 1H), 4.03 (t, J=6.4 Hz, 2H), 2.58 (m, 2H), 2.14 (s, 3H). Mass spectrum (MALDI-TOF, α-cyano-4-hydroxycinnamic acid matrix) calcd. for C$_{21}$H$_{22}$N$_4$O$_4$S: 427.1 (M+H), 449.1 (M+Na). Found: 427.1, 449.0.

EXAMPLE 26

2-[2-[3-(2-Chloro-5-trifluoromethylphenylsulfonyloxy)-5-methylphenoxy]-ethyl-1-methylene] hydrazinecarboximidamide nitrate a) 3-(2-Chloro-5-trifluoromethylphenylsulfonyloxy)-5-methylphenol Orcinol monohydrate (1.42 g, 10.0 mmol) and 2-chloro-5-trifluoromethylbenzenesulfonyl chloride (2.79 g, 10.0 mmol) were mixed in saturated aqueous NaHCO$_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over Na$_2$SO$_4$. After removing the solvent in vacuo, the residue was purified by flash column chromatography (dichloromethane to 3% ethyl acetate in dichloromethane) to give the title compound as a pale yellow oil (1.50 g, 41%). $^1$H-NMR (300 MHz, CDCl$_3$) δ 8.24 (d, J=1.9 Hz, 1H), 7.83 (dd, J=8.3, 2.1 Hz, 1H), 7.76 (d, J=8.4 Hz, 1H), 6.57 (s, 1H), 6.55 (s, 1H), 6.46 (s, 1H), 5.07 (br s, 1H), 2.24 (s, 3H).

b) 3-[3-(2-Chloro-5-trifluoromethylphenylsulfonyloxy)-5-methyl-phenoxy]propanol

To a solution of 3-(2-chloro-5-trifluoromethylphenylsulfonyloxy)-5-methylphenol (734 mg, 2.0 mmol), as prepared in the preceding step, tri-n-butylphosphine (607 mg, 3.0 mmol) and 1,3-propanediol (760 mg, 10 mmol) in anhydrous tetrahydrofuran (20 mL) was added 1,1'-(azodicarbonyl)dipiperidine (757 mg, 3.0 mmol). The mixture was stirred at ambient temperature overnight. Hexane (30 mL) was added to the mixture, and the precipitates were removed by filtration. The filtrate was evaporated in vacuo, and the residue was purified by flash column chromatography (1:1 hexane/ethyl acetate) to give the title compound as a pale yellow oil (650 mg, 76%). $^1$H-NMR (300 MHz, CDCl$_3$) δ 8.24 (d, J=1.9 Hz, 1H), 7.84 (dd, J=8.4, 2.1 Hz, 1H), 7.77 (d, J=8.4 Hz, 1H), 6.64 (s, 1H), 6.54 (s, 1H), 6.51 (s, 1H), 4.03 (t, J=6.0 Hz, 2H), 3.82 (t, J=6.0 Hz, 2H), 2.26 (s, 3H), 2.00 (t, J=6.0 Hz, 2H), 1.60 (s, 1H).

c) 3-[3-(2-Chloro-5-trifluoromethylphenylsulfonyloxy)-5-methyl-phenoxy]propionaldehyde Sulfur trioxide pyridine complex (720 mg, 4.5 mmol) was added to a solution of 3-[3-(2-chloro-5-trifluoromethylphenylsulfonyloxy)-5-methylphenoxy]propanol (600 mg, 1.4 mmol), as prepared in the preceding step, N,N-diisopropylethylamine (0.6 mL, 4.7 mmol) and anhydrous dimethyl sulfoxide (0.3 mL, 4.2 mmol) in anhydrous dichloromethane (20 mL). The reaction mixture was stirred at ambient temperature for 1 hour and then quenched with 10% aqueous citric acid (50 mL). The mixture was extracted into dichloromethane (3×50 mL), and the dichloromethane solution was washed with 10% aqueous citric acid (40 mL) and dried over Na$_2$SO$_4$. After removing the solvent in vacuo, the residue was purified by flash column chromatography (dichloromethane) to give the title compound as a colorless oil (410 mg, 69%). $^1$H-NMR (300 MHz, CDCl$_3$) δ 9.83 (s, 1H), 8.24 (d, J=2.1 Hz, 1H), 7.84 (dd, J=8.4, 2.1 Hz, 1H), 7.78 (d, J=8.4 Hz, 1H), 6.64 (s, 1H), 6.57 (s, 1H), 6.51 (s, 1H), 4.21 (t, J=6.0 Hz, 2H), 2.88 (t, J=6.0 Hz, 2H), 2.27 (s, 3H).

d) 2-[2-[3-(2-Chloro-5-trifluoromethylphenylsulfonyloxy)-5-methylphenoxy]ethyl-1-methylene]hydrazinecarboximidamide nitrate A solution of 3-[3-(2-chloro-5-trifluoromethylphenylsulfonyloxy)-5-methylphenoxy]propionaldehyde (400 mg, 0.95 mmol), as prepared in the preceding step, and aminoguanidine nitrate (275 mg, 2.0 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (420 mg, 81%). $^1$H-NMR (300 MHz, DMSO-d$_6$) δ 8.25 (dd, J=8.4, 2.1 Hz, 1H), 8.15 (d, J=8.5 Hz, 1H), 8.12 (t, J=2.1 Hz, 1H), 7.54 (t, J=5.0 Hz, 1H), 7.45 (br s, 4H), 6.80 (s, 1H), 6.55 (s, 1H), 6.51 (s, 1H), 4.16 (t, J=6.4 Hz, 2H), 2.68 (m, 2H), 2.22 (s, 3H). Mass spectrum (MALDI-TOF, α-cyano-4-hydroxycinnamic acid matrix) calcd. for C$_{18}$H$_{18}$ClF$_3$N$_4$O$_4$S: 479.1 (M+H), 501.1 (M+Na). Found: 479.3, 501.5.

EXAMPLE 27

2-Amino-[2-[2-[3-(5-chloro-2-methoxyphenylsulfonyloxy)-5-methylphenoxylethy]-1-methylene]hydrazine]carboximidamine acetate a) 2-Amino-[2-[2-[3-(5-chloro-2-methoxyphenylsulfonyloxy)-5-methylphenoxy]ethyl-1-methylene]hydrazine]carboximidamine acetate A mixture of 3-[3-(5-chloro-2-methoxyphenylsulfonyloxy)-5-methylphenoxy]propionaldehyde (245 mg, 0.64 mmol, prepared in step b of example 18), N,N'-diaminoguanidine monohydrochloride (827 mg, 6.6 mmol), ethanol (5 mL) and methanol (10 mL) was stirred overnight at ambient temperature. Solvent was removed in vacuo, and the residue was triturated with dichloromethane. The mixture was filtered through Celite, and the filtrate was concentrated to a foam. The foam was dissolved in dichloromethane and extracted with aqueous NaOH (pH 12). The aqueous layer was extracted with dichloromethane, and the combined organic layers were washed with brine. The organic layer was dried over K$_2$CO$_3$, filtered and evaporated to give the free base of the title compound as an orange foam. The free base was dissolved in dichloromethane (3 mL) and treated with glacial acetic acid (0.18 mL). The solution was concentrated, and crude product was purified by flash column chromatography through silica gel (0.2:2:98 to 1:10:90 acetic acid/methanol/dichloromethane) to give the title compound as an unstable light brown oil (98.7 mg, 30%) which converts to 1,3-di-[[3-(5-chloro-2-methoxy-phenylsulfonyloxy)-5-methylphenoxy]-3-propylideneamino]guanidine acetate upon standing. Mass spectrum of the title compound (MALDI-TOF, α-cyano-4-hydroxy-cinnamic acid matrix) calcd. for C$_{18}$H$_{22}$ClN$_5$O$_5$S: 456.1 (M+H). Found: 456.5. $^1$H-NMR of 1,3-di-[[3-(5-chloro-2-methoxyphenylsulfonyloxy)-5-methylphenoxy]-3-propylideneamino]guanidine acetate (300 MHz, CDCl$_3$) δ 7.81 (d, 2H, J=2.6 Hz), 7.61 (t, 2H, J=5 Hz), 7.56 (dd, 2H, J=2.6, 8.9 Hz), 7.04 (d, 2H, J=8.9 Hz), 6.60 (br s, 2H), 6.52 (br s, 2H), 6.47 (m, 2H), 4.09 (t, 4H, J=6.3 Hz), 4.01 (s, 6H), 2.72 (q, 4H, J=6 Hz), 2.26 (s, 6H). Mass spectrum of 1,3-di-[[3-(5-chloro-2-methoxyphenylsulfonyloxy)-5-methylphenoxy]-3-propylideneamino]guanidine acetate (MALDI-TOF, α-cyano-4-hydroxycinnamic acid matrix) calcd. for C$_{35}$H$_{37}$Cl$_2$N$_5$O$_{10}$S$_2$: 822.1 (M+H). Found: 822.9.

EXAMPLE 28

1-Amino-2-[2-[3-(5-chloro-2-methoxyphenylsulfonyloxy)-5-methylphenoxy]ethyl-1-methylene]hydrazinecarboximidamine acetate A mixture of 3-[3-(5-chloro-2-methoxyphenylsulfonyloxy)-5-methylphenoxy]propionaldehyde (231 mg, 0.60 mmol, prepared in step b of example 18), N',N'-diaminoguanidine monohydrochloride (758 mg, 6.0 mmol), ethanol (5 mL) and methanol (10 mL) was stirred overnight at ambient temperature. Solvent was removed in vacuo, and the residue was triturated with dichloromethane. The mixture was filtered through Celite, and the filtrate was concentrated to a light pink foam. The foam was dissolved in dichloromethane and extracted with aqueous NaOH (pH 10). The aqueous layer was extracted with dichloromethane, and the combined organic layers were washed with brine. The organic layer was dried over K$_2$CO$_3$, filtered and evaporated to give the free base of the title compound as a brown foam. The free base was dissolved in dichloromethane (3 mL) and treated with glacial acetic acid (0.18 mL). The solution was concentrated, and crude product was purified by flash column chromatography through silica gel (0.2:2:98 to 1:10:90 acetic acid/methanol/dichloromethane) to give the title compound as an unstable brown oil (66 mg, 21%) which converts to 1,1-di-[[3-(5-chloro-2-methoxy-phenylsulfonyloxy)-5-methylphenoxy]-3-propylideneamino]guanidine acetate. Mass spectrum of title compound (MALDI-TOF, α-cyano-4-hydroxycinnamic acid matrix) calcd. for $C_{18}H_{22}ClN_5O_5O_5S$: 456.1 (M+H). Found: 456.1. $^1$H-NMR of 1,1-di-[[3-(5-chloro-2-methoxyphenylsulfonyloxy)-5-methylphenoxy]-3-propylideneamino]guanidine acetate (300 MHz, CDCl$_3$) δ 7.81 (d, 2H, J=2.6H), 7.60 (br s, 2H), 7.56 (dd, 2H, J=2.6, 8.9 Hz), 7.04 (d, 2H, J=8.9 Hz), 6.60 (br s, 2H), 6.53 (br s, 2H), 6.47 (t, 2H, J=2.1 Hz), 4.09 (t, 4H, J=6.3 Hz), 4.01 (s, 6H), 2.72 (q, 4H, J=6 Hz), 2.26 (d, 6H, J=0.2 Hz). Mass spectrum of 1,1-di-[[3-(5-chloro-2-methoxyphenylsulfonyloxy)-5-methylphenoxy]-3-propylideneamino]guanidine acetate (MALDI-TOF, α-cyano-4-hydroxycinnamic acid matrix) calcd. for $C_{35}H_{37}Cl_2N_5O_{10}S_2$: 822.1 (M+H), 844.1 (M+Na). Found: 822.6, 844.8.

EXAMPLE 29

2-[3-(2-Methoxyphenylsulfonyloxy)-5-methylphenoxy]methyl-1-methylene]-hydrazinecarboximidamide nitrate a) 2-[3-(2-Methoxyphenylsulfonyloxy)-5-methylphenoxy]ethanol A solution of 3-(2-methoxyphenylsulfonyloxy)-5-methylphenol (245 mg, 0.83 mmol, prepared in step b of example 8), ethylene glycol (0.23 mL, 4.1 mmol), 1,1'-(azodicarbonyl)dipiperidine (420 mg, 1.66 mmol) and anhydrous tetrahydrofuran (6 mL) was cooled to 0° C. under nitrogen. Tri-n-butylphosphine (0.41 mL, 1.66 mmol) was added dropwise over 2.5 minutes. The mixture was stirred at 0° C. for 5 hours, then more 1,1'-(azodicarbonyl)dipiperidine (210 mg) and tri-n-butylphosphine (0.21 mL) were added. The reaction was stirred overnight at ambient temperature, then more 1,1'-(azodicarbonyl)dipiperidine (420 mg) and tri-n-butylphosphine (0.41 mL) were added. The mixture was stirred overnight at ambient temperature, then diethyl ether (50 mL) was added and the mixture was filtered. The filtrate was concentrated, and the residue was purified by flash column chromatography through silica gel (3:2 ethyl acetate/hexane) to give the title compound as a colorless oil (190 mg, 67%). $^1$H-NMR (300 MHz, CDCl$_3$) δ 7.82 (dd, 1H, J=1.7, 7.9 Hz), 7.62 (ddd, 1H, J=1.8, 7.4, 8.4 Hz), 7.09 (dd, 1H, J=0.8, 8.4 Hz), 6.99–7.05 (m, 1H), 6.60–6.61 (m, 1H), 6.53–6.55 (m, 1H), 6.46–6.48 (m, 1H), 4.02 (s, 3H), 3.89–4.01 (m, 4H), 2.25 (d, 3H, J=0.6 Hz). Mass spectrum (MALDI-TOF, α-cyano-4-hydroxycinnamic acid matrix) calcd. for $C_{16}H_{18}O_6S$: 361.1 (M+Na). Found: 360.6.

b) 3-(2-Methoxyphenylsulfonyloxy)-5-methylphenoxyacetaldehyde

A solution of 2-[3-(2-methoxyphenylsulfonyloxy)-5-methylphenoxy]-ethanol (322 mg, 0.95 mmol, as prepared in the preceding step), N,N-diisopropylethylamine (0.35 mL, 2.0 mmol), anhydrous dimethyl sulfoxide (0.20 mL, 2.9 mmol) and anhydrous dichloromethane (2.5 mL) was cooled to 0° C. under nitrogen. Sulfur trioxide pyridine complex (308 mg, 1.9 mmol) was added in portions over 10 minutes. The solution was stirred at 0° C. for 5 hours, then the reaction was quenched with 5% aqueous citric acid (25 mL). Diethyl ether (25 mL) was added, and the mixture was extracted. The aqueous layer was extracted with diethyl ether (25 mL), and the combined organic layers were washed with 5% aqueous citric acid (25 mL). The aqueous layer was extracted with diethyl ether (25 mL), and the combined organic layers were washed with pH 7 buffer (0.5M, 2×40 mL) and brine (40 mL). The organic layer was dried over Na$_2$SO$_4$, filtered, and concentrated to an oil. Crude product was purified by flash column chromatography through silica gel (0% to 5% acetone in dichloromethane) to give the title compound as a colorless oil (195 mg, 61%). $^1$H-NMR (300 MHz, CDCl$_3$) δ 9.76 (t, 1H, J=1 Hz), 7.81 (dd, 1H, J=1.7, 7.9 Hz), 7.60–7.65 (m, 1H), 7.09 (d, 1H, J=8 Hz), 7.00–7.05 (m, 1H), 6.63 (br s, 1H), 6.59 (br s, 1H), 6.41 (t, 1H, J=2.2 Hz), 4.45 (d, 2H, J=1 Hz), 4.03 (s, 3H), 2.27 (s, 3H). Mass spectrum (MALDI-TOF, α-cyano-4-hydroxycinnamic acid matrix) calcd. for $C_{16}H_{16}O_6S$: 359.1 (M+Na). Found: 358.8.

c) 2-[3-(2-Methoxyphenylsulfonyloxy)-5-methylphenoxy]methyl-1-methylene]hydrazinecarboximidamide nitrate A mixture of 3-(2-methoxyphenylsulfonyloxy)-5-methylphenoxy-acetaldehyde (193 mg, 0.57 mmol, as prepared in the preceding step), aminoguanidine nitrate (159 mg, 1.2 mmol), ethanol (4.7 mL) and methanol (1.0 mL) was stirred overnight at ambient temperature. The mixture was concentrated in vacuo to remove methanol, then water (24 mL) was added dropwise. The title compound was isolated by filtration as a white solid (208 mg, 80%). $^1$H-NMR (300 MHz, DMSO-d$_6$) δ 7.74–7.80 (m, 1H), 7.70 (dd, 1H, J=1.5, 7.8 Hz), 7.37 (d, 1H, J=8.5 Hz), 7.10 (t, 1H, J=7.4 Hz), 6.79 (br s, 1H), 6.49 (br s, 2H), 4.65 (d, 2H, J=5.0 Hz), 3.99 (s, 3H), 2.22 (s, 3H). Mass spectrum (MALDI-TOF, α-cyano-4-hydroxycinnamic acid matrix) calcd. for $C_{17}H_{20}N_4O_5S$: 393.1 (M+H). Found: 393.3.

EXAMPLE 30

2-[2-[3-(2-Cyano-5-methylphenylsulfonyloxy)-5-methylphenoxy]ethyl-1-methylene]hydrazinecarboximidamide nitrate a) 2-Amino-4-methylbenzonitrile A mixture of 4-methyl-2-nitrobenzonitrile (4.9 g, 30 mmol) and 10% palladium on carbon (500 mg) in 1,4-dioxane (60 mL) was stirred under hydrogen (balloon) overnight. The catalyst was removed by filtration through the Celite, and the filtrate was concentrated in vacuo. The residue was purified by flash chromatography (dichloromethane) to give the title compound as a pale yellow solid (3.3 g, 83%). $^1$H-NMR (300 MHz, CDCl$_3$) δ 7.26 (d, J=8.3 Hz, 1H), 6.56 (s, 1H), 6.55 (s, 1H), 4.32 (br s, 2H), 2.29 (s, 3H).

b) 2-Cyano-5-methylbenzenesulfonyl chloride

To a solution of 2-amino-4-methylbenzonitrile (2.65 g, 20 mmol), as prepared in the preceding step, in 30% aqueous HCl (7 mL) was added 40% aqueous sodium nitrite (6 mL) at 0°–5° C. After 15 minute, to the diazo solution were added 30% HCl (15 mL), copper sulfate (100 mg) and 40% aqueous sodium bisulfite (15 mL) at 5°–10° C. The mixture was stirred for 30 minute, then additional water (50 mL) was added. The mixture was extracted into dichloromethane (3×50 mL), and the dichloromethane solution was washed with brine (50 mL) and dried over Na$_2$SO$_4$. After removing the solvent in vacuo, the residue was purified by flash column chromatography (2:1 dichloromethane/hexane) to give the title compound as a white solid (2.1 g, 52%). $^1$H-NMR (300 MHz, CDCl$_3$) δ 8.03 (s, 1H), 7.87 (d, J=7.8 Hz, 1H), 7.66 (d, J=7.8 Hz, 1H), 2.59 (s, 3H).

c) 3-(2-Cyano-5-methylphenylsulfonyloxy)-5-methylphenol

Orcinol monohydrate (1.42 g, 10.0 mmol) and 2-cyano-5-methylbenzene-sulfonyl chloride (2.0 g, 9.0 mmol), as prepared in the preceding step, were mixed in saturated aqueous NaHCO$_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over Na$_2$SO$_4$. After removing the solvent in vacuo, the residue was purified by flash column chromatography (dichloromethane to 4% ethyl acetate in dichloromethane) to give the title compound as a pale yellow oil (2.1 g, 69%). $^1$H-NMR (300 MHz, CDCl$_3$) δ 7.91 (s, 1H), 7.81 (d, J=7.8 Hz, 1H), 7.57 (d, J=7.9 Hz, 1H), 6.59 (s, 1H), 6.58 (s, 1H), 6.51 (s, 1H), 5.61 (s, 1H), 2.51 (s, 3H), 2.29 (s, 3H).

d) 3-[3-(2-Cyano-5-methylphenylsulfonyloxy)-5-methylphenoxy]propanol

To a solution of 3-(2-cyano-5-methylphenylsulfonyloxy)-5-methylphenol (910 mg, 3.0 mol), as prepared in the preceding step, tri-n-butylphosphine (900 mg, 4.5 mmol) and 1,3-propanediol (1.14 g, 15 mmol) in anhydrous tetrahydrofuran (30 mL) was added 1,1'-(azodicarbonyl)dipiperidine (1.14 g, 4.5 mmol). The mixture was stirred at ambient temperature overnight. Hexane (50 mL) was added to the mixture, and the precipitates were removed by filtration. The filtrate was evaporated in vacuo, the residue was purified by flash column chromatography (5% ethyl acetate in dichloromethane) to give the title compound as a colorless oil (950 mg, 88%). $^1$H-NMR (300 MHz, CDCl$_3$) δ 7.91 (s, 1H), 7.81 (d, J=7.9 Hz, 1H), 7.58 (d, J=7.8 Hz, 1H), 6.66 (s, 1H), 6.60 (s, 1H), 6.58 (s, 1H), 4.05 (t, J=6.0 Hz, 2H), 3.82 (t, J=5.9 Hz, 2H), 2.51 (s, 3H), 2.27 (s, 3H), 2.02 (t, J=6.0 Hz, 2H), 1.75 (br s, 1H).

e) 3-[3-(2-Cyano-5-methylphenylsulfonyloxy)-5-methylphenoxy]propionaldehyde

Sulfur trioxide pyridine complex (1.0 g, 6.5 mmol) was added to a solution of 3-[3-(2-cyano-5-methylphenylsulfonyloxy)-5-methylphenoxy]-propanol (720 mg, 2.0 mmol), as prepared in the preceding step, N,N-diisopropylethylamine (0.7 mL, 5.5 mmol) and anhydrous dimethyl sulfoxide (0.4 mL, 5.6 mmol) in anhydrous dichloromethane (20 mL). The reaction mixture was stirred at ambient temperature for 1 hour and then quenched with 10% aqueous citric acid (60 mL). The mixture was extracted into dichloromethane (3×50 mL), and the dichloromethane solution was washed with 10% aqueous citric acid (40 mL) and dried over Na$_2$SO$_4$. After removing the solvent in vacuo, the residue was purified by flash column chromatography (dichloromethane) to give the title compound as a colorless oil (520 mg, 72%). $^1$H-NMR (300 MHz, CDCl$_3$) δ 9.81 (s, 1H), 7.89 (s, 1H), 7.79 (d, J=7.8 Hz, 1H), 7.55 (d, J=7.9 Hz, 1H), 6.62 (s, 1H), 6.60 (s, 1H), 6.56 (s, 1H), 4.22 (t, J=6.0 Hz, 2H), 2.85 (t, J=6.0 Hz, 2H), 2.49 (s, 3H), 2.25 (s, 3H).

f) 2-[2-[3-(2-Cyano-5-methylphenylsulfonyloxy)-5-methylphenoxy]-ethyl-1-methylene]hydrazinecarboximidamide nitrate A solution of 3-[3-(2-cyano-5-methylphenylsulfonyloxy)-5-methylphenoxy]propionaldehyde (500 mg, 1.4 mmol), as prepared in the preceding step, and aminoguanidine nitrate (410 mg, 3.0 mmol) in ethanol (10 mL) was stirred at ambient temperature overnight. Water (50 mL) was added to the reaction mixture. The precipitates were collected, washed with water (2×30 mL) and diethyl ether (2×30 mL), and dried under high vacuum to give the title compound as a white solid (580 mg, 86%). $^1$H-NMR (300 MHz, DMSO-d$_6$) δ 8.16 (d, J=7.9 Hz, 1H), 7.96 (s, 1H), 7.84 (d, J=7.9 Hz, 1H), 7.55 (t, J=5.0 Hz, 1H), 7.46 (br s, 4H), 6.81 (s, 1H), 6.54 (s, 1H), 6.52 (s, 1H), 4.17 (t, J=6.2 Hz, 2H), 2.70 (t, J=6.1 Hz, 2H), 2.51 (s, 3H), 2.24 (s, 3H). Mass spectrum (MALDI-TOF, α-cyano-4-hydroxycinnamic acid matrix) calcd. for C$_{19}$H$_{21}$N$_5$O$_4$S: 416.1 (M+H), 438.1 (M+Na). Found: 415.9, 437.9.

EXAMPLE 31

2-[2-[(3-Methyl-5-(N-(4-phenylbutyl)-N-(2-trifluoromethylphenylsulfonyl))-amino)phenoxy]ethyl-1-methylene]hydrazinecarboximidamide acetate a) 1-[3-Benzyloxy-5-methylphenyl-(2-trifluoromethylphenyl)-sulfonylamino]-4-phenylbutane To 350 mg (0.731 mmol) of 3-benzyloxy-5-methyl-1-(2-trifluoromethylphenylsulfonylamino)benzene, as prepared in step f of example 5, in anhydrous tetrahydrofuran (3 mL) containing 169 μL (1.1 mmol) of 3-phenylbutanol and 221 mg (0.877 mmol) of 1,1'-(azodicarbonyl)dipiperidine was added 194 μL (0.88 mmol) of tri-n-butylphosphine. The reaction mixture was stirred for 3 h. To the partially completed reaction mixture was added another 169 μL of 4-phenylbutanol, 221 mg of 1,1'-(azodicarbonyl)dipiperidine, and 194 μL of tri-n-butylphosphine. The reaction mixture was stirred at ambient temperature for 4 days. The reaction mixture was concentrated and purified by flash chromatography (dichloromethane/hexane (1:1 to 100:0)) to give 480 mg of the title compound as a colorless oil (impure) which was used directly in the next reaction. $^1$H-NMR (300 MHz, CDCl$_3$) δ 7.84 (d, 1H, J=8 Hz), 7.70 (d, 1H, J=8 Hz), 7.59 (t, 1H, J=8 Hz), 7.46 (td, 1H, J=1, 8 Hz), 7.10–7.38 (m, 10H), 6.7 (s, 1H), 6.51–6.52 (m, 2H), 4.93 (s, 2H), 3.69 (t, 2H, J=7 Hz), 2.57 (t, 2H, J=7 Hz), 2.22 (s, 3H), 1.42–1.7 (m, 4H).

b) [5-Methyl-3-(N-(4-phenylbutyl)-N-(2-trifluoromethylphenylsulfonyl))amino]phenol A mixture 480 mg of 1-[3-benzyloxy-5-methylphenyl-(2-trifluoromethylphenyl)sulfonylamino]-4-phenylbutane, as prepared in the preceding step, and 100 mg of 10% palladium on carbon in tetrahydrofuran (5 mL) was hydrogenated at atmospheric pressure and ambient temperature for 1 h. The reaction mixture was filtered through Celite and concentrated to give 430 mg of nearly pure title compound as a colorless oil which was used directly in the next reaction. $^1$H-NMR (300 MHz, CDCl$_3$) δ 7.85 (d, 1H, J=7.5 Hz), 7.74 (d, 1H, J=7.5 Hz), 7.61 (t, 1H, J=7.5 Hz), 7.50 (t, 1H, J=6 Hz), 7.12–7.28 (m, 5H), 6.55 (s, 1 H), 6.43 (s, 1H), 6.37 (t, 1H, J=2 Hz), 3.70 (t, 2H, J=7 Hz), 2.59 (t, 2H, J=7.5 Hz), 2.19 (s, 3H), 1.68 (pentet, 2H), 1.48 (pentet, 2H). Mass spectrum (MALDI-TOF, α-cyano-4-hydroxycinnamic acid matrix) calcd. for C$_{24}$H$_{24}$F$_3$NO$_3$S: 486.3 (M+Na). Found: 486.1.

c) 3-[(5-Methyl-3-(N-(4-phenylbutyl)-N-(2-trifluoromethylphenylsulfonyl)) amino)phenoxy]propanol To a solution of 430 mg of [5-methyl-3-(N-(4-phenylbutyl)-N-(2-trifluoromethylphenylsulfonyl))amino]phenol, as prepared in the preceding step, in anhydrous tetrahydrofuran (5 mL) containing 250 μL (3.45 mmol) of 1,3-propanediol and 564 mg (22.4 mmol) of 1,1'-(azodicarbonyl)dipiperidine was added 557 μL (2.24 mmol) of tri-n-butylphosphine. The reaction mixture was stirred overnight, diluted with diethyl ether, filtered, and purified by flash chromatography (3% to 5% to 10% diethyl ether/dichloromethane) to give 220 mg (58% yield from 3-benzyloxy-5-methyl-1-(2-trifluoromethylphenylsulfonylamino)benzene) of the title compound as a colorless oil. $^1$H-NMR (300 MHz, CDCl$_3$) δ

7.85 (d, 1H, J=7.2 Hz), 7.75 (d, 1H, J=8 Hz), 7.61 (t, 1H, J=7.5 Hz), 7.51 (t, 1H, J=6 Hz), 7.11–7.27 (m, 5H), 6.63 (s, 1H), 6.48 (s, 1H), 6.47 (s, 1H), 3.99 (t, 2H, J=6 Hz), 3.82 (q, 2H, J=6 Hz), 3.70 (t, 2H, J=7 Hz), 2.58 (t, 2H, J=7.6 Hz), 2.21 (s, 3H), 1.99 (pentet, 2H, J=5 Hz), 1.44–1.72 (m, 4H). Mass spectrum (MALDI-TOF, α-cyano-4-hydroxycinnamic acid matrix) calcd. for $C_{27}H_{30}F_3NO_4S$: 544.2 (M+Na). Found: 543.6.

d) 3-[(5-Methyl-3-(N-(4-phenylbutyl)-N-(2-trifluoromethylphenylsulfonyl)) amino)phenoxy] propionaldehyde To a solution of 221 mg (0.422 mmol) of 3-[(5-methyl-3-(N-(4-phenylbutyl)-N-(2-trifluoromethylphenylsulfonyl))-amino)phenoxy]propanol, as prepared in the preceding step, 230 μL of N,N-diisopropylethylamine, and 52 μL (0.67 mmol) of anhydrous dimethyl sulfoxide in anhydrous dichloromethane (2 mL) at 0° C. was added 100 mg (0.63 mmol) of sulfur trioxide pyridine complex. The reaction mixture was stirred at 0° C. for 20 min. The reaction mixture was quenched with 5% aqueous citric acid, extracted into dichloromethane, dried ($MgSO_4$), and concentrated to give title compound which was used directly in the next reaction. $^1$H-NMR (300 MHz, $CDCl_3$) δ 9.84 (t, 1H, J=1.5 Hz), 7.86 (d, 1H, J=7.5 Hz), 7.74 (d, 1H, J=7.5 Hz), 7.62 (t, 1H, J=7.5 Hz), 7.53 (t, 1H, J=6 Hz), 7.11–7.28 (m, 5H), 6.62 (s, 1H), 6.50 (s, 1H), 6.45–6.47 (m, 1H), 4.17 (t, 2H, J=6 Hz), 3.70 (t, 2H, J=7 Hz), 2.85 (dd, 2H, J=1.5, 6 Hz), 2.58 (t, 2H, J=6 Hz), 2.21 (s, 3H), 1.4–1.7 (m, 4H). Mass spectrum (MALDI-TOF, gentisic acid matrix) calcd. for $C_{27}H_{28}F_3NO_4S$: 542.2 (M+Na). Found: 541.9.

e) 2-[2-[(3-Methyl-5-(N-(4-phenylbutyl)-N-(2-trifluoromethylphenylsulfonyl))amino)phenoxy]ethyl-1-methylene]hydrazinecarboximidamide acetate A mixture of 3-[(5-methyl-3-(N-(4-phenylbutyl)-N-(2-trifluoromethylphenylsulfonyl))amino)phenoxy] propionaldehyde, as prepared in the preceding step, and 350 mg (2.55 mmol) of aminoguanidine nitrate in 4 mL of ethanol was stirred overnight. The reaction mixture was basified with 2N NaOH, diluted with water, and extracted into dichloromethane. The reaction mixture was dried ($K_2CO_3$) and concentrated. The reaction mixture was purified through a 10 g Waters Sep-Pak silica gel column using an elution of 33:60:6:1 tetrahydrofuran/dichloromethane/methanol/glacial acetic acid to give 119.6 mg of the title compound as an oily residue. $^1$H-NMR (300 MHz, DMSO-$d_6$) δ 7.92 (d, 1H, J=8 Hz), 7.82 (d, 1H, J=8 Hz), 7.75 (t, 1H, J=7 Hz), 7.67 (dt, 1H, J=1, 8 Hz), 7.53 (t, 1H, J=7 Hz), 7.11–7.24 (m, 5H), 6.71 (s, 1H), 6.53 (t, 1H, J=1 Hz), 6.46 (s, 1H), 2.74 (q, 2H, J=5 Hz), 2.57 (t, 2H, J=7 Hz), 2.19 (s, 3H), 1.91 (s, 3H). Mass spectrum (MALDI-TOF, α-cyano-4-hydroxycinnamic acid matrix) calcd. for $C_{28}H_{32}F_3N_5O_3S$: 576.2 (M+Na). Found: 576.2.

EXAMPLE 32

2-[2-[3-(5-Isoquinolinylsulfonyloxy)-5-methylphenoxy]ethyl-1-methylene]-hydrazinecarboximidamide nitrate a) 5-Isoquinolinesulfonyl chloride A mixture of 5-isoquinolinesulfonic acid (4.18 g, 20 mmol), and phosphorus pentachloride (6.24 g, 30 mmol) in phosphorus oxychloride (20 mL) was heated at 120° C. for two days. The reaction mixture was cooled to ambient temperature and diluted with dry chloroform (60 mL). The white precipitate was collected, washed with dry chloroform and dried under high vacuum to give the title compound as a white solid (4.40 g, 83%) which was used for the next step without further purification. $^1$H-NMR (300 MHz, $CDCl_3$) δ 9.95 (s, 1H), 9.16 (d, J=6.8 Hz, 1H), 8.74 (d, J=6.8 Hz, 1H), 8.52 (t, J=7.0 Hz, 2H), 7.99 (t, J=7.3 Hz, 1H).

b) 3-(5-Isoquinolinylsulfonyloxy)-5-methylphenol

Orcinol monohydrate (1.42 g, 10.0 mmol) and 5-isoquinolinesulfonyl chloride (2.64 g, 10.0 mmol), as prepared in the preceding step, were mixed in saturated aqueous $NaHCO_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over $Na_2SO_4$. After removing the solvent in vacuo, the residue was triturated from ether/hexane to give the title compound as a pale yellow solid (1.15 g, 37%). $^1$H-NMR (300 MHz, $CDCl_3$) δ 9.67 (s, 1H), 9.60 (s, 1H), 8.86 (d, J=6.1 Hz, 1H), 8.63 (d, J=8.2 Hz, 1H), 8.37 (t, J=6.1 Hz, 2H), 7.86 (t, J=7.8 Hz, 1H), 6.46 (s, 1H), 6.23 (s, 1H), 5.97 (s, 1H), 2.08 (s, 3H).

c) 3-[3-(5-Isoquinolinylsulfonyloxy)-5-methylphenoxy]propanol

To a solution of 3-(5-isoquinolinylsulfonyloxy)-5-methylphenol (630 mg, 2.0 mmol), as prepared in the preceding step, tri-n-butylphosphine (607 mg, 3.0 mmol) and 1,3-propanediol (760 mg, 10 mmol) in anhydrous tetrahydrofuran (20 mL) was added 1,1'-(azodicarbonyl) dipiperidine (757 mg, 3.0 mmol). The mixture was stirred at ambient temperature overnight. Hexane (30 mL) was added to the mixture and the precipitates were removed by filtration. The filtrate was evaporated in vacuo, and the residue was purified by flash column chromatography (4:1 ethyl acetate/dichloromethane) to give the title compound as a colorless oil (620 mg, 82%). $^1$H-NMR (300 MHz, $CDCl_3$) δ 9.41 (s, 1H), 8.80 (d, J=6.1 Hz, 1H), 8.54 (d, J=6.1 Hz, 1H), 8.33 (d, J=7.2 Hz, 1H), 8.29 (d, J=7.6 Hz, 1H), 7.67 (t, J=7.7 Hz, 1H), 6.56 (s, 1H), 6.29 (s, 1H), 6.24 (s, 1H), 3.89 (t, J=6.1 Hz, 2H), 3.75 (t, J=6.0 Hz, 2H), 2.16 (s, 3H), 2.05 (m, 2H), 1.90 (br s, 1H).

d) 3-[3-(5-Isoquinolinylsulfonyloxy)-5-methylphenoxy]propionaldehyde

Sulfur trioxide pyridine complex (240 mg, 1.5 mmol) was added to a solution of 3-[3-(5-isoquinolinylsulfonyloxy)-5-methylphenoxy]propanol (190 mg, 0.5 mmol), as prepared in the preceding step, N,N-diisopropylethylamine (0.2 mL, 1.6 mmol) and anhydrous dimethyl sulfoxide (0.1 mL, 1.4 mmol) in anhydrous dichloromethane (20 mL). The reaction mixture was stirred at ambient temperature for 1 hour and then quenched with 10% aqueous citric acid (30 mL). The mixture was extracted into dichloromethane (3×30 mL), and the dichloromethane solution was washed with 10% aqueous citric acid (30 mL) and dried over $Na_2SO_4$. After removing the solvent in vacuo, the residue was purified by flash column chromatography (3:1 ethyl acetate/dichloromethane) to give the title compound as a colorless oil (135 mg, 72%). $^1$H-NMR (300 MHz, $CDCl_3$) δ 9.79 (s, 1H), 9.46 (s, 1H), 8.80 (d, J=6.2 Hz, 1H), 8.59 (d, J=5.8 Hz, 1H), 8.37 (d, J=7.5 Hz, 1H), 8.34 (d, J=8.3 Hz, 1H), 7.71 (t, J=7.7 Hz, 1H), 6.56 (s, 1H), 6.32 (s, 1H), 6.24 (s, 1H), 4.09 (t, J=6.0 Hz, 2H), 2.81 (t, J=6.0 Hz, 2H), 2.17 (s, 3H).

e) 2-[2-[3-(5-Isoquinolinylsulfonyloxy)-5-methylphenoxy]ethyl-1-methylene] hydrazinecarboximidamide nitrate A solution of 3-[3-(5-isoquinolinylsulfonyloxy)-5-methylphenoxy]-propionaldehyde (110 mg, 0.3 mmol), as prepared in the preceding step, and aminoguanidine nitrate (137 mg, 1.0 mmol) in ethanol (5 mL) was stirred at ambient temperature overnight. Water (20 mL) was added to the reaction mixture. The precipitates were collected, washed with water (2×10 mL) and diethyl ether (2×10 mL), and dried under high vacuum to give the title compound as a white solid (120 mg, 81%). $^1$H-NMR (300 MHz, DMSO-$d_6$) δ 9.59 (s, 1H), 8.85 (d, J=6.1 Hz, 1H), 8.63 (d, J=8.3 Hz, 1H), 8.40 (d, J=7.5 Hz, 1H), 8.38 (d, J=6.0 Hz, 1H), 7.86 (t, J=7.7 Hz, 1H), 6.50 (t, J=5.0 Hz, 1H), 7.45 (br s, 4H), 6.71 (s, 1H), 6.32 (s, 1H), 6.30 (s, 1H), 4.05 (t, J=6.3 Hz, 2H), 2.61 (t, J=6.2 Hz, 2H), 2.13 (s, 3H). Mass spectrum (MALDI-TOF, α-cyano-4-hydroxycinnamic acid matrix) calcd. for $C_{20}H_{21}N_5O_4S$: 428.1 (M+H), 450.1 (M+Na). Found: 427.8, 449.9.

EXAMPLE 33

2-[[1-[5-Methyl-3-(quinolinyl-8-sulfonyloxy) phenoxy]methyl]cyclopropyl-1-methylene] hydrazinecarboximidamide acetate a) [1-[5-Methyl-3-(quinolinyl-8-sulfonyloxy)phenoxy] methyl]-cyclopropylmethanol To 250 mg (0.75 mmol) of 5-methyl-3-(quinolinyl-8-sulfonyloxy)phenol, as prepared in step a of example 15, 170 mg (1.7 mmol) of 1,1-di(hydroxymethyl)cyclopropane (as prepared in U.S. Pat. No. 5,472,964), and 370 μL (1.49 mmol) of tri-n-butylphosphine in 5 mL of anhydrous tetrahydrofuran was added 378 mg (1.5 mmol) of 1,1'-(azodicarbonyl)dipiperidine. The reaction mixture was stirred at ambient temperature for 2 days. The reaction mixture was diluted with diethyl ether, filtered, and the filtrate concentrated. The residue was purified by flash chromatography (dichloromethane/ethyl acetate (2:1 to 1:1)) to give the title compound as a gum (177 mg, 59%). $^1$H-NMR (300 MHz, CDCl$_3$) δ 9.27 (dd, 1H, J=2, 4 Hz), 8.42 (dd, 1H, J=1.5, 7.5 Hz), 8.30 (dd, 1H, J=2, 8 Hz), 7.06–7.65 (m, 2H), 6.56 (s, 1H), 6.44–6.47 (m, 2H), 3.73 (s, 2H), 3.56 (d, 2H, J=5.5 Hz), 2.17 (s, 3H), 1.79 (t, 1H, J=5.5 Hz), 0.53–0.62 (m, 4H). Mass spectrum (MALDI-TOF, α-cyano-4-hydroxycinnamic acid matrix) calcd. for $C_{21}H_{21}NO_5S$: 400.1 (M+H). Found: 399.8.

b) [1-[5-Methyl-3-(quinolinyl-8-sulfonyloxy)phenoxy]- methyl]cyclopropylcarboxaldehyde To a solution of 177 mg (0.44 mmol) of [1-[5-methyl-3-(quinolinyl-8-sulfonyloxy)phenoxy]methyl] cyclopropylmethanol, as prepared in the preceding step, in anhydrous dichloromethane (2 mL) containing 230 μL (1.32 mmol) of N,N-diisopropylethylamine and 55 μL (0.71 mmol) of anhydrous dimethyl sulfoxide was added 104 mg (0.65 mmol) of sulfur trioxide pyridine complex. The reaction mixture was stirred for 1 h, and to the partially completed reaction mixture was added another 100 μL of N,N-diisopropylethylamine, 25 μL of anhydrous dimethyl sulfoxide, and 50 mg of sulfur trioxide pyridine complex. The reaction mixture was stirred for 40 min, diluted with 30 mL of dichloromethane, washed with water, dried ($K_2CO_3$), concentrated, and purified by passing through a 10 mL pad of silica gel using elutions of 2–10% diethyl ether/dichloromethane to give 153 mg (87%) of the title compound as an oil. $^1$H-NMR (300 MHz, CDCl$_3$) δ 9.26 (dd, 1H, J=2, 4 Hz), 8.96 (s, 1H), 8.42 (dd, 1H, J=1.5, 7.5 Hz), 8.31 (dd, 1H, J=2, 8 Hz), 8.15 (dd, 1H, J=1.5, 8 Hz), 7.60–7.65 (m, 2H), 6.54–6.56 (m, 1H), 6.47–6.49 (m, 1H), 6.43 (t, 1H, J=2 Hz), 3.99 (s, 2H), 2.17 (s, 3H), 1.1–1.34 (m, 4H). Mass spectrum (MALDI-TOF, α-cyano-4-hydroxycinnamic acid matrix) calcd. for $C_{21}H_{19}NO_5S$: 398.1 (M+H), 420.1 (M+Na). Found: 397.6, 419.7.

c) 2-[[1-[5-Methyl-3-(quinolinyl-8-sulfonyloxy) phenoxy]methyl]-cyclopropyl-1-methylene] hydrazinecarboximidamide acetate A mixture of 153 mg (0.385 mmol) of [1-[5-methyl-3-(quinolinyl-8-sulfonyloxy) phenoxy]methyl] cyclopropylcarboxaldehyde, as prepared in the preceding step, and 112 mg (0.82 mmol) of aminoguanidine nitrate in ethanol (3 mL) was stirred at ambient temperature overnight then at 50° C. for 2 h. The reaction mixture was basified with 2N NaOH, diluted with water, and extracted into dichloromethane. The organic phase was dried ($K_2CO_3$), concentrated, and purified over a Waters Sep-Pak silica gel column (10 g) using elutions of dichloromethane, then dichloromethane/methanol/glacial acetic acid (92.7:6.3:1 to 89:9.5:1) to give 148.8 mg of the title compound. $^1$H-NMR (300 MHz, CD$_3$OD) δ 9.14 (dd, 1H, J=1.7, 4 Hz), 8.53 (dd, 1H, J=1.8, 8 Hz), 8.32–8.39 (m, 2H), 7.64–7.7 (m, 2H), 6.62 (s, 1H), 6.35–6.38 (m, 2H), 3.96 (s, 2H), 2.12 (s, 3H), 1.93 (s, 3H), 0.87–1.1 (m, 4H). Mass spectrum (MALDI-TOF, α-cyano-4-hydroxycinnamic acid matrix) calcd. for $C_{22}H_{22}N_5O_4S$: 453.1 (M+H). Found: 453.3.

EXAMPLE 34

2-[2-[5-Methyl-3-(3-pyridinylsulfonyloxy)phenoxy] ethyl-1-methylene]-hydrazinecarboximidamide acetate a) 5-Methyl-3-(3-pyridinylsulfonyloxy)phenol A mixture of orcinol monohydrate (1.42 g, 0.01 mol) and 3-pyridylsulfonyl chloride hydrochloride (2.13 g, 0.01 mol), as prepared in J. Am. Chem. Soc., 114:4889 (1992), in saturated aqueous sodium bicarbonate (17.5 mL) and dichloromethane (50 mL) was stirred rapidly at ambient temperature for 2 days. The dichloromethane was separated and the aqueous layer was extracted with ethyl acetate (3×25 mL). The ethyl acetate and dichloromethane extracts were combined and washed with brine, dried over anhydrous sodium sulfate, and evaporated to dryness. The residue was recrystallized from ether and hexane, collected by filtration, and dried under high vacuum to give 1.54 g of a white solid (58% yield). $^1$H-NMR (300 MHz, CDCl$_3$) δ 9.03 (d, 1H), 8.88 (dd, 1H), 8.16 (dt, 1H), 7.5 (m, 1H), 6.57 (d, 1H), 6.42 (s, 1H), 6.32 (t, 1H), 2.24 (s, 3H).

b) 3-[5-Methyl-3-(3-pyridinylsulfonyloxy)phenoxy] propanol

A solution of triphenylphosphine (1.52 g, 0.0058 mol), 5-methyl-3-(3-pyridinylsulfonyloxy)phenol (1.54 g, 0.0058 mol), as prepared in the preceding step, and 1,3-propanediol (0.42 mL, 0.0058 mol) in anhydrous tetrahydrofuran (50 mL) was treated with diethyl azodicarboxylate (0.92 mL, 0.0058 mol) and allowed to stir at ambient temperature for 3 days. The tetrahydrofuran was evaporated, and the solid residue was treated with hexane. Solvent was decanted and the solid was treated with dichloromethane and diluted with hexane to produce a crystalline solid which was collected by filtration. The filtrate was evaporated to dryness and partitioned between water and diethyl ether. The aqueous layer was separated and extracted with diethyl ether (2×50 mL). The diethyl ether extracts were combined, washed with brine, and dried over anhydrous sodium sulfate. The diethyl ether extract was evaporated to a gum which was purified further by silica gel chromatography using 10% ethyl acetate/90% dichloromethane, followed by 15% ethyl acetate/85% dichloromethane, 20% ethyl acetate/80% dichloromethane, and finally 25% ethyl acetate/75% dichloromethane. The appropriate fractions were combined and evaporated to a gum (1.3 g). $^1$H-NMR (300 MHz, CDCl$_3$) δ 9.03 (d, 1H), 8.89 (dd, 1H), 8.14 (m, 1H), 6.64 (s, 1H), 6.42 (s, 1H), 6.37 (t, 1H), 4.00 (t, 2H), 3.81 (q, 2H), 2.25 (s, 3H), and 1.99 (pentet, 2H). Mass spectrum (MALDI-TOF, α-cyano-4-hydroxycinnamic acid matrix) calcd. for C$_{15}$H$_{17}$NO$_5$S: 278.0 (M–C$_3$H$_7$O+Na). Found: 278.9.

c) 3-[5-Methyl-3-(3-pyridinylsulfonyloxy)phenoxy]propionaldehyde

At 0° C. to a solution of 276 mg (0.855 mmol) of 3-[5-methyl-3-(3-pyridinylsulfonyloxy)phenoxy]propanol, as prepared in the preceding step, in anhydrous dichloromethane (2 mL) containing 450 µL (2.58 mmol) of N,N-diisopropylethylamine and 92 µL (1.19 mmol) of anhydrous dimethyl sulfoxide was added 204 mg (1.28 mmol) of sulfur trioxide pyridine complex. The reaction mixture was stirred at 0° C. for 30 min, diluted with 20 mL of toluene, and concentrated to an oil which was used directly in the next reaction.

d) 2-[2-[5-Methyl-3-(3-pyridinylsulfonyloxy)phenoxy]ethyl-1-methylene]-hydrazinecarboximidamide diacetate A mixture of 3-[5-methyl-3-(3-pyridinylsulfonyloxy)phenoxy]-propionaldehyde, as prepared in the preceding step, and 386 mg (2.82 mmol) of aminoguanidine nitrate in 3 mL of ethanol was stirred at ambient temperature overnight. The reaction mixture was quenched with excess 2N NaOH, extracted into dichloromethane, dried (K$_2$CO$_3$), and concentrated. The reaction mixture was diluted with dichloromethane, treated with 800 µL of glacial acetic acid, and concentrated. The residue was purified by chromatography over a Waters Sep-Pak silica gel column (10 g) using elutions of dichloromethane/methanol/glacial acetic acid (89:9.5:1.5 to 78:19:3) to give 141 mg of the title compound. $^1$H-NMR (300 MHz, CD$_3$OD) δ 8.87–8.91 (m, 2H), 8.27 (td, 1H, J=1.6, 8 Hz), 7.64–7.69 (m, 1H), 7.52 (t, 1H, J=5.2 Hz), 6.74 (s, 1H), 6.44 (s, 2H), 4.13 (t, 2H, J=6Hz), 2.73 (q, 2H, J=6Hz), 2.24 (s, 3H), 1.93 (s, 6H). Mass spectrum (MALDI-TOF, α-cyano-4-hydroxycinnamic acid matrix) calcd. for C$_{16}$H$_{19}$N$_5$O$_4$S: 378.1 (M+H). Found: 379.3.

EXAMPLE 35

2-[2-[3-(3-Fluorophenylsulfonyloxy)-5-methylphenoxy]ethyl-1-methylene]-hydrazinecarboximidamide nitrate a) 3-(3-Fluorophenylsulfonyloxy)-5-methylphenol To a solution of 0.704 g (5.67 mmol) of orcinol monohydrate and 1.00 g (5.15 mmol) of 3-fluorobenzenesulfonyl chloride in 25 mL of diethyl ether was added 25 mL of saturated aqueous NaHCO$_3$ and the biphasic mixture was stirred vigorously at ambient temperature for 3 days. The layers were separated and the aqueous layer extracted with 2×30 mL of ethyl acetate. The combined organic layers were washed with 50 mL of brine, dried (Na$_2$SO$_4$) and concentrated to 1.41 g of a pale amber-colored oil. This material was flash chromatographed on 65 g of silica gel with 3% ethyl acetate-dichloromethane to afford 935 mg (68%) of the desired product as a colorless syrup: $^1$H-NMR (300 MHz; CDCl$_3$) δ 7.66 (ddd, 1H, J=7.8, 1.7, 1.1 Hz), 7.55 (m, 2H), 7.38 (tdd, 1H, J=8.3, 2.6, 1.1 Hz), 6.56 (m, 1H), 6.40 (m, 1H), 6.33 (td, 1H, J=2.2, 0.5 Hz), 5.29 (s, 1H) and 2.23 (s, 3H).

b) 3-[3-(3-Fluorophenylsulfonyloxy)-5-methylphenoxy]propanol

A solution of 3-(3-fluorophenylsulfonyloxy)-5-methylphenol (930 mg, 3.3 mmol, as prepared in the preceding step), 1,3-propanediol (0.75 mL, 10 mmol), 1,1'-(azodicarbonyl)dipiperidine (1.76 g, 7.0 mmol), and anhydrous tetrahydrofuran (20 mL) was cooled to 0° C. under nitrogen. Tri-n-butylphosphine (1.7 mL, 7.0 mmol) was added dropwise over 8.5 minutes. The mixture was stirred at 0° C. for 5 minutes then at ambient temperature for 5.5 hours. Diethyl ether (100 mL) was added, and the mixture was stirred for 15 minutes. The mixture was filtered, and the filtrate was concentrated. The residue was purified by flash column chromatography through silica gel (25% to 35% ethyl acetate in hexane) to give the title compound as a yellow oil (877 mg, 78%). $^1$H-NMR (300 MHz, CDCl$_3$) δ 7.65–7.68 (m, 1H), 7.50–7.60 (m, 2H), 7.35–7.41 (m, 1H), 6.63 (br s, 1H), 6.41 (br s, 1H), 6.38 (br t, 1H, J=2.1 Hz), 4.01 (t, 2H, J=6.0 Hz), 3.82 (br t, 2H, J=6.0 Hz), 2.25 (s, 3H), 1.99 (pentet, 2H, J=6.0 Hz). Mass spectrum (MALDI-TOF, α-cyano-4-hydroxycinnamic acid matrix) calcd. for C$_{16}$H$_{17}$FO$_5$S: 363.1 (M+Na), 379.0 (M+K). Found: 362.8, 378.9.

c) 3-[3-(3-Fluorophenylsulfonyloxy)-5-methylphenoxy]propionaldehyde

A solution of 3-[3-(3-fluorophenylsulfonyloxy)-5-methylphenoxy]-propanol (840 mg, 2.5 mmol, as prepared in the preceding step), N,N-diisopropylethylamine (0.90 mL, 25.2 mmol), anhydrous dimethyl sulfoxide (0.52 mL, 27.4 mmol), and anhydrous dichloromethane (25.9 mL) was cooled to 0° C. under nitrogen. Sulfur trioxide pyridine complex (830 mg, 5.2 mmol) was added in portions over 13 minutes. The solution was stirred at 0° C. for 2.75 hours, then the reaction was quenched with 10% aqueous citric acid (60 mL). Diethyl ether (60 mL) was added, and the mixture was extracted. The aqueous layer was extracted with diethyl ether (30 mL), and the combined organic layers were washed with 5% aqueous citric acid (100 mL). The aqueous layer was extracted with diethyl ether (30 mL), and the combined organic layers were washed with pH 7 buffer (50 mL) and brine (50 mL). The organic layer was dried over Na$_2$SO$_4$, filtered, and concentrated to an oil. The crude product was purified by flash column chromatography through silica gel (40% diethyl ether in hexane) to give the title compound as a pale yellow oil (468 mg, 56%). $^1$H-NMR (300 MHz, CDCl$_3$) δ 9.84 (t, 1H, J=1.4 Hz), 7.51–7.68 (m, 3H), 7.35–7.42 (m, 1H), 6.63 (br s, 1H), 6.44 (br s, 1H), 6.37 (br t, 1H, J=2.2 Hz), 4.20 (t, 2H, J=6.1 Hz), 2.87 (td, 2H, J=1.4, 6.1 Hz), 2.26 (s, 3H). Mass spectrum (MALDI-TOF, α-cyano-4-hydroxycinnamic acid matrix) calcd. for C$_{16}$H$_{15}$FO$_5$S: 361.1 (M+Na). Found: 361.3.

d) 2-[2-[3-(3-Fluorophenylsulfonyloxy)-5-methylphenoxy]ethyl-1-methylene]hydrazinecarboximidamide nitrate A mixture of 3-[3-(3-fluorophenylsulfonyloxy)-5-methylphenoxy]-propionaldehyde (458 mg, 1.4 mmol, as prepared in the preceding step), aminoguanidine nitrate (372 mg, 2.7 mmol) and ethanol (11 mL) was stirred for 6 days at ambient temperature. Water was added dropwise over 15 minutes, and the mixture was stirred for an additional 30 minutes. The title compound was isolated by filtration as a white solid (377 mg, 61%). $^1$H-NMR (300 MHz, DMSO-d$_6$) δ 7.70–7.81 (m, 4H), 7.54 (t, 1H, J=5.0 Hz), 6.77 (br s, 1H), 6.48–6.49 (m, 2H), 4.14 (t, 2H, J=6.4 Hz), 2.68 (td, 2H, J=5.0, 6.4 Hz), 2.22 (s, 3H). Mass spectrum (MALDI-TOF, α-cyano-4-hydroxycinnamic acid matrix) calcd. for C$_{17}$H$_{19}$FN$_4$O$_4$S: 395.1 (M+H). Found: 394.8.

EXAMPLE 36

2-[2-[3-(3-Cyanophenylsulfonyloxy)-5-methylphenoxy]ethyl-1-methylene]-hydrazinecarboximidamide nitrate a) 3-(3-Cyanophenylsulfonyloxy)-5-methylphenol Orcinol monohydrate (1.42 g, 10.0 mmol) and 3-cyanobenzenesulfonyl chloride (2.02 g, 10.0 mmol) were mixed in saturated aqueous NaHCO$_3$ (30 mL) and diethyl ether (30 mL). The biphasic mixture was stirred vigorously at ambient temperature overnight. The reaction mixture was diluted with water (50 mL) and extracted into ethyl acetate (3×50 mL). The organic phase was washed with brine (2×50 mL) and dried over Na$_2$SO$_4$. After removing the solvent in vacuo, the residue was purified by flash column chromatography (dichloromethane to 5% ethyl acetate in dichloromethane) to give the title compound as a pale yellow oil (2.40 g, 83%). $^1$H-NMR (300 MHz, CDCl$_3$) δ 8.12 (s, 1H), 8.07 (d, J=8.0 Hz, 1H), 7.93 (d, J=7.8 Hz, 1H), 7.68 (t, J=7.9 Hz, 1H), 6.56 (s, 1H), 6.36 (s, 1H), 6.30 (s, 1H), 5.35 (s, 1H), 2.22 (s, 3H).

b) 3-[3-(3-Cyanophenylsulfonyloxy)-5-methylphenoxy]propanol

To a solution of 3-(3-cyanophenylsulfonyloxy)-5-methylphenol (2.30 g, 8.0 mmol), as prepared in the preceding step, tri-n-butylphosphine (2.4 g, 12.0 mmol) and 1,3-propanediol (3.0 g, 40 mmol) in anhydrous tetrahydrofuran (50 mL) was added 1,1'-(azodicarbonyl)dipiperidine (3.0 g, 12.0 mmol). The mixture was stirred at ambient temperature overnight. Hexane (100 mL) was added to the mixture, and the precipitates were removed by filtration. The filtrate was evaporated in vacuo, and the residue was purified by flash column chromatography (10% ethyl acetate in dichloromethane) to give the title compound as a colorless oil (2.2 g, 79%). $^1$H-NMR (300 MHz, CDCl$_3$) δ 8.13 (s, 1H), 8.10 (d, J=8.0 Hz, 1H), 7.95 (d, J=7.9 Hz, 1H), 7.71 (t, J=7.9 Hz, 1H), 6.65 (s, 1H), 6.40 (s, 1H), 6.37 (s, 1H), 4.02 (t, J=6.0 Hz, 2H), 3.82 (t, J=6.0 Hz, 2H), 2.26 (s, 3H), 2.00 (t, J=6.0 Hz, 2H), 1.67 (br s, 1H).

c) 3-[3-(3-Cyanophenylsulfonyloxy)-5-methylphenoxy]propionaldehyde

Sulfur trioxide pyridine complex (1.10 g, 7.0 mmol) was added to a solution of 3-[3-(3-cyanophenylsulfonyloxy)-5-methylphenoxy]propanol (1.05 g, 3.0 mmol), as prepared in the preceding step, N,N-diisopropylethylamine (0.7 mL, 5.5 mmol) and anhydrous dimethyl sulfoxide (0.4 mL, 5.6 mmol) in anhydrous dichloromethane (20 mL). The reaction mixture was stirred at ambient temperature for 1 hour and then quenched with 10% aqueous citric acid (80 mL). The mixture was extracted into dichloromethane (3×60 mL), and the dichloromethane solution was washed with 10% aqueous citric acid (50 mL) and dried over Na$_2$SO$_4$. After removing the solvent in vacuo, the residue was purified by flash column chromatography (dichloromethane) to give the title compound as a colorless oil (770 mg, 74%). $^1$H-NMR (300 MHz, CDCl$_3$) δ 9.84 (s, 1H), 8.14 (s, 1H), 8.09 (d, J=8.0 Hz, 1H), 7.96 (d, J=8.0 Hz, 1H), 7.72 (t, J=7.9 Hz, 1H), 6.65 (s, 1H), 6.42 (s, 1H), 6.37 (s, 1H), 4.21 (t, J=6.0 Hz, 2H), 2.89 (t, J=6.0 Hz, 2H), 2.27 (s, 3H).

d) 2-[2-[3-(3-Cyanophenylsulfonyloxy)-5-methylphenoxy]ethyl-1-methylene]hydrazinecarboximidamide nitrate A solution of 3-[3-(3-cyanophenylsulfonyloxy)-5-methylphenoxy]-propionaldehyde (690 mg, 2.0 mmol), as prepared in the preceding step, and aminoguanidine nitrate (550 mg, 4.0 mmol) in ethanol (10 mL) was stirred at ambient temperature overnight. Water (60 mL) was added to the reaction mixture. The precipitates were collected, washed with water (2×40 mL) and diethyl ether (2×40 mL), and dried under high vacuum to give the title compound as a white solid (750 mg, 81%). $^1$H-NMR (300 MHz, DMSO-d$_6$) δ 11.21 (s, 1H), 8.45 (s, 1H), 8.30 (d, J=7.8 Hz, 1H), 8.19 (d, J=8.1 Hz, 1H), 7.88 (t, J=7.9 Hz, 1H), 7.55 (t, J=4.9 Hz, 1H), 7.45 (br s, 4H), 6.78 (s, 1H), 6.51 (s, 2H), 4.15 (t J=6.3 Hz, 2H), 2.69 (t, J=6.2 Hz, 2H), 2.23 (s, 3H). Mass spectrum (MALDI-TOF, α-cyano-4-hydroxycinnamic acid matrix) calcd. for C$_{18}$H$_{19}$N$_5$O$_4$S: 402.1 (M+H), 424.1 (M+Na). Found: 402.2, 424.1.

EXAMPLE 37

2-[2-[3-(3-Bromophenylsulfonyloxy)-5-methylphenoxy]ethyl-1-methylene]hydrazinecarboximidamide nitrate a) 3-(3-Bromophenylsulfonyloxy)-5-methylphenol To a solution of 534 mg (4.30 mmol) of orcinol monohydrate and 1.00 g (3.91 mmol) of 3-bromobenzenesulfonyl chloride in 25 mL of diethyl ether was added 25 mL of saturated aqueous NaHCO$_3$ and the biphasic mixture was stirred vigorously at ambient temperature for 3 days. The layers were separated and the aqueous layer extracted with 2×30 mL of ethyl acetate. The combined organic layers were washed with 50 mL of brine, dried (Na$_2$SO$_4$) and concentrated to 1.4 g of an amber-colored resin. Chromatography on 65 g of silica gel with 3% ethyl acetate-dichloromethane afforded 870 mg (65%) of the desired product as a colorless syrup: $^1$H-NMR (300 MHz; CDCl$_3$) δ 8.02 (t, 1H, J=1.8 Hz), 7.79 (m, 2H), 7.41 (t, 1H, J=7.9 Hz), 6.57 (m, 1H), 6.40 (m, 1H), 6.33 (t, 1H, J=2.2 Hz) and 2.24 (s, 3H).

b) 3-[3-(3-Bromophenylsulfonyloxy)-5-methylphenoxy]propanol

To a cooled (0° C.) solution of 0.815 g (2.37 mmol) 3-(3-bromophenylsulfonyloxy)-5-methylphenol, as prepared in the preceding step, 0.51 mL (7.12 mmol) of 1,3-propanediol and 1.20 g (4.75 mmol) of 1,1'-(azodicarbonyl)dipiperidine in 15 mL of anhydrous tetrahydrofuran was added 1.18 mL (4.75 mmol) of tri-n-butylphosphine dropwise over 8 min. Dichloromethane (10 mL) was added to aid stirring. After stirring at ambient temperature for 5.5 h, the reaction mixture was diluted with 100 mL of diethyl ether. The resulting mixture was stirred for 30 min, filtered and the filtrate concentrated to give a pale yellow semisolid. This residue was flash chromatographed on 80 g of silica gel with 25–50% ethyl acetate-hexane to afford 0.914 g (96% yield) of the title compound as a colorless resin: $^1$H-NMR (300 MHz; CDCl$_3$) δ 8.01 (t, 1H, J=1.8 Hz), 7.79 (m, 2H), 7.42 (t, 1H, J=8.0 Hz), 6.64 (s, 1H), 6.41 (s, 1H), 6.37 (t, 1H, J=2.2 Hz), 4.01 (t, 2H, J=6.0 Hz), 3.83 (t, 2H, J=5.6 Hz), 2.26 (s, 3H) and 2.00 (m, 2H).

c) 3-[3-(3-Bromophenylsulfonyloxy)-5-methylphenoxy]propionaldehyde

To a cooled (0° C.), stirred solution of 914 mg (2.28 mmol) 3-[3-(3-bromophenylsulfonyloxy)-5-methylphenoxy]propanol, as prepared in the preceding step, 795 μL of N,N-diisopropylethylamine and 485 μL of anhydrous dimethyl sulfoxide in 15 mL of anhydrous dichloromethane was added 732 mg (4.60 mmol) of sulfur trioxide pyridine complex. The mixture was warmed to ambient temperature over 30 min and stirred for 3 h. The mixture was poured into 15 mL of dichloromethane and washed with 5% (w/v) aqueous citric acid (2×25 mL). Each wash was extracted with 5 mL of dichloromethane and the combined extracts were washed with brine (25 mL) and dried over Na$_2$SO$_4$ to give, after concentration, a white semisolid. This material was chromatographed on 80 g of silica gel with 3% ethyl acetate-dichloromethane to afford 620 mg (68%) of the title compound as a colorless oil: $^1$H-NMR (300 MHz; CDCl$_3$) δ 9.84 (t, 1H, J=1.4 Hz), 8.01 (t, 1H, J=1.8 Hz), 7.79 (m, 2H), 7.43 (t, 1H, J=8.0 Hz), 6.64 (m, 1H), 6.44 (m, 1H), 6.37 (t, 1H, J=2.0 Hz), 4.20 (t, 2H, J=6.1 Hz), 2.87 (td, 2H, J=6.1, 1.4 Hz) and 2.26 (s, 3H). Mass spectrum (MALDI-TOF, α-cyano-4-hydroxycinnamic acid matrix) calcd. for $C_{16}H_{15}BrO_5S$: 423.0 (M+2+ Na, $^{81}Br$ ion). Found: 423.1.

d) 2-[2-[3-(3-Bromophenylsulfonyloxy)-5-methylphenoxy]ethyl-1-methylene]hydrazinecarboximidamide nitrate To 590 mg (1.48 mmol) of 3-[3-(3-bromophenylsulfonyloxy)-5-methylphenoxy] propionaldehyde, as prepared in the preceding step, in 12 mL of absolute ethanol was added 406 mg (2.96 mmol) of aminoguanidine nitrate and the mixture stirred at ambient temperature for three days. The mixture was diluted slowly with 60 mL of water, stirred for 10 min and filtered washing with 5 mL of cold water. The solid was air-dried under suction followed by high vacuum to afford 650 mg (85%) of the title compound as a white solid: $^1$H-NMR (300 MHz; DMSO-$d_6$) δ 8.04 (m, 2H), 7.91 (d, 1H, J=8.0 Hz), 7.65 (t, 1H, J=8.0 Hz), 7.55 (t, 1H, J=5.0 Hz), 7.47 (br s, 3H), 6.79 (s, 1H), 6.49 (m, 2H), 4.15 (t, 2H, J=6.4 Hz), 2.69 (dd, 2H, J=11.4, 6.3 Hz) and 2.23 (s, 3H). Mass spectrum (MALDI-TOF, α-cyano-4-hydroxycinnamic acid matrix) calcd. for $C_{17}H_{19}BrN_4O_4S$: 457.0 (M+2+H, $^{81}Br$ ion). Found: 456.9.

EXAMPLE 38

2-[2-[5-Methyl-3-(2-nitrophenylsulfonyloxy)phenoxy]ethyl-1-methylene]-hydrazinecarboximidamide nitrate a) 5-Methyl-3-(2-nitrophenylsulfonyloxy)phenol Orcinol monohydrate (4.27 g, 30.0 mmol) and 2-nitrobenzenesulfonyl chloride (6.65 g, 30.0 mmol) were mixed in saturated aqueous $NaHCO_3$ (100 mL) and diethyl ether (100 mL). The biphasic mixture was stirred vigorously at ambient temperature overnight. The reaction mixture was diluted with water (150 mL) and extracted into ethyl acetate (3×100 mL). The organic phase was washed with brine (2×100 mL) and dried over $Na_2SO_4$. After removing the solvent in vacuo, the residue was purified by flash column chromatography (dichloromethane to 5% ethyl acetate in dichloromethane) to give the title compound as a pale yellow solid (6.10 g, 73%). $^1$H-NMR (300 MHz, CDCl$_3$) δ 8.09 (d, J=7.8 Hz, 1H), 7.85 (m, 2H), 7.71 (m, 1H), 6.62 (s, 1H), 6.59 (s, 1H), 6.51 (s, 1H), 5.06 (s, 1H), 2.26 (s, 3H).

b) 3-[5-Methyl-3-(2-nitrophenylsulfonyloxy)phenoxy] propanol

To a solution of 5-methyl-3-(2-nitrophenylsulfonyloxy) phenol (1.1 g, 4.0 mmol), as prepared in the preceding step, tri-n-butylphosphine (1.22 g, 6.0 mmol) and 1,3-propanediol (1.52 g, 20 mmol) in anhydrous tetrahydrofuran (40 mL) was added 1,1'-(azodicarbonyl)dipiperidine (1.51 g, 6.0 mmol). The mixture was stirred at ambient temperature overnight. Hexane (60 mL) was added to the mixture, and the precipitates were removed by filtration. The filtrate was evaporated in vacuo, and the residue was purified by flash column chromatography (5% ethyl acetate in dichloromethane) to give the title compound as a pale yellow oil (1.05 g, 71%). $^1$H-NMR (300 MHz, CDCl$_3$) δ 7.99 (d, J=7.7 Hz, 1H), 7.84 (m, 2H), 7.70 (m, 1H), 6.65 (s, 1H), 6.61 (s, 1H), 6.58 (s, 1H), 4.03 (t, J=6.0 Hz, 2H), 3.82 (t, J=5.9 Hz, 2H), 2.27 (s, 3H), 2.00 (t, J=6.0 Hz, 2H), 1.67 (br s, 1H).

c) 3-[5-Methyl-3-(2-nitrophenylsulfonyloxy)phenoxy] propionaldehyde

Sulfur trioxide pyridine complex (1.12 mg, 7.0 mmol) was added to a solution of 3-[5-methyl-3-(2-nitrophenylsulfonyloxy)phenoxy]propanol (920 mg, 2.5 mmol), as prepared in the preceding step, N,N-diisopropylethylamine (0.7 mL, 5.5 mmol) and anhydrous dimethyl sulfoxide (0.4 mL, 5.6 mmol) in anhydrous dichloromethane (20 mL). The reaction mixture was stirred at ambient temperature for 1 hour and then quenched with 10% aqueous citric acid (50 mL). The mixture was extracted into dichloromethane (3×50 mL), and the dichloromethane solution was washed with 10% aqueous citric acid (40 mL) and dried over $Na_2SO_4$. After removing the solvent in vacuo, the residue was purified by flash column chromatography (dichloromethane) to give the title compound as a pale yellow oil (780 mg, 85%). $^1$H-NMR (300 MHz, CDCl$_3$) δ 9.84 (s, 1H), 7.99 (d, J=7.6 Hz, 1H), 7.85 (m, 2H), 7.70 (m, 1H), 6.64 (s, 2H), 6.57 (s, 1H), 4.22 (t, J=6.0 Hz, 2H), 2.88 (t, J=6.0 Hz, 2H), 2.27 (s, 3H).

d) 2-[2-[5-Methyl-3-(2-nitrophenylsulfonyloxy)phenoxy]ethyl-1-methylene]hydrazinecarboximidamide nitrate A solution of 3-[5-methyl-3-(2-nitrophenylsulfonyloxy) phenoxy]-propionaldehyde (730 mg, 2.0 mmol), as prepared in the preceding step, and aminoguanidine nitrate (550 mg, 4.0 mmol) in ethanol (15 mL) was stirred at ambient temperature overnight. Water (60 mL) was added to the reaction mixture. The precipitates were collected, washed with water (2×40 mL) and diethyl ether (2×40 mL), and dried under high vacuum to give the title compound as a white solid (750 mg, 77%). $^1$H-NMR (300 MHz, DMSO-$d_6$) δ 8.21 (d, J=7.9 Hz, 1H), 8.09 (d, J=7.5 Hz, 1H), 8.03 (d, J=7.5 Hz, 1H), 7.90 (t, J 7.7 Hz, 1H), 7.55 (t, J=5.0 Hz, 1H), 7.45 (br s, 4H), 6.82 (s, 1H), 6.56 (s, 2H), 4.17 (t, J=6.3 Hz, 2H), 2.69 (m, 2H), 2.24 (s, 3H). Mass spectrum (MALDI-TOF, α-cyano-4-hydroxycinnamic acid matrix) calcd. for $C_{17}H_{19}N_5O_6S$: 422.1 (M+H), 444.1 (M+Na). Found: 422.2, 444.0.

EXAMPLE 39

2-[[1-[3-(2-Cyanophenylsulfonyloxy)-5-methylphenoxy]-methyl]cyclopropyl-1-methylene] hydrazinecarboximidamide acetate a) [1-[3-(2-Cyanophenylsulfonyloxy)-5-methylphenoxy] methyl]-cyclopropylmethanol To a solution of 3-(2-cyanophenylsulfonyloxy)-5-methylphenol (1.45 g, 5.0 mmol), as prepared in the step a of example 13), tri-n-butylphosphine (1.62 g, 8.0 mmol) and 1,1-dihydroxymethylcyclopropane (1.52 g, 15 mmol), as prepared in U.S. Pat. No. 5,472,964, in anhydrous tetrahydrofuran (50 mL) was added 1,1'-(azodicarbonyl) dipiperidine (2.02, 8.0 mmol). The mixture was stirred at ambient temperature overnight. Hexane (80 mL) was added to the mixture, and the precipitates were removed by filtration. The filtrate was evaporated in vacuo, and the residue was purified by flash column chromatography (10% ethyl acetate in dichloromethane) to give the title compound as a white solid (1.15, 62%). $^1$H-NMR (300 MHz, CDCl$_3$) δ 8.09 (m, 1H), 7.93 (m, 1H), 7.80 (m, 2H), 6.66 (s, 1H), 6.60 (s, 1H), 6.56 (s, 1H), 3.86 (s, 2H), 3.60 (s, 2H), 2.26 (s, 3H), 1.85 (br s, 1H), 0.62 (s, 4H).

b) [1-[3-(2-Cyanophenylsulfonyloxy)-5-methylphenoxy] methyl]-cyclopropylcarboxaldehyde Sulfur trioxide pyridine complex (480 mg, 3.0 mmol) was added to a solution of [1-[3-(2-cyanophenylsulfonyloxy)-5-methylphenoxy]methyl]-cyclopropylmethanol (373 mg, 1.0 mmol), as prepared in the preceding step, N,N-diisopropylethylamine (0.4 mL, 3.1 mmol) and anhydrous dimethyl sulfoxide (0.2 mL, 2.8 mmol) in anhydrous dichloromethane (10 mL). The reaction mixture was stirred at ambient temperature for 1 hour and then quenched with 10% aqueous citric acid (40 mL). The mixture was extracted into dichloromethane (3×40 mL), and the dichloromethane solution was washed with 10% aqueous citric acid (30 mL) and dried over $Na_2SO_4$. After removing the solvent in vacuo, the residue was purified by flash column chromatography (dichloromethane) to give the title compound as a white solid (345 mg, 93%). $^1$H-NMR (300 MHz, $CDCl_3$) δ 8.98 (s, 1H), 8.12 (m, 1H), 8.09 (m, 1H), 7.94 (m, 2H), 6.66 (s, 1H), 6.60 (s, 1H), 6.57 (s, 1H), 4.12 (s, 2H), 2.26 (s, 3H), 1.33 (m, 2H), 1.25 (m, 2H).

c) 2-[[1-[3-(2-Cyanophenylsulfonyloxy)-5-methylphenoxyl-methyl]-cyclopropyl-1-methylene]hydrazinecarboximidamide acetate A solution of [1-[3-(2-cyanophenylsulfonyloxy)-5-methylphenoxy]-methyl]cyclopropylcarboxaldehyde (334 mg, 0.9 mmol), as prepared in the preceding step, and aminoguanidine nitrate (247 mg, 1.8 mmol) in ethanol (10 mL) was stirred at ambient temperature overnight. The mixture was quenched with water (50 mL) and basified to pH 10 by using 2N NaOH. The basified solution was extracted with dichloromethane (3×50 mL). The dichloromethane solution was washed with brine (2×50 mL) and dried over $Na_2SO_4$. After evaporating the solvent in vacuo, the residue was purified by flash column chromatography (90:9:1 dichloromethane/methanol/acetic acid) to give the title compound as a white solid (340 mg, 77%). $^1$H-NMR (300 MHz, DMSO-$d_6$) δ 8.29 (d, J=7.4 Hz, 1H), 8.09 (d, J=7.4 Hz, 1H), 8.03 (t, J=7.1 Hz, 1H), 7.97 (t, J=7.4 Hz, 1H), 7.19 (s, 1H), 6.79 (s, 1H), 6.72 (br s, 4H), 6.48 (s, 1H), 6.44 (s, 1H), 4.03 (s, 2H), 2.21 (s, 3H), 1.78 (s, 3H), 0.97 (m, 2H), 0.89 (m, 2H). Mass spectrum (MALDI-TOF, α-cyano-4-hydroxycinnamic acid matrix) calcd. for $C_{20}H_{21}N_5O_4S$: 428.1 (M+H), 450.1 (M+Na). Found: 428.1, 449.8.

EXAMPLE 40

2-[2-[5-Methyl-3-(phenylmethylsulfonyloxy)phenoxy]ethyl-1-methylene]-hydrazinecarboximidamide acetate a) 5-Methyl-3-(phenylmethylsulfonyloxy)phenol To a solution of 2.0 g (16.1 mmol) of orcinol in diethyl ether (100 mL) containing 10 mL of N,N-diisopropylethylamine was added in a slow steady stream 3.05 g (16 mmol) of α-toluenesulfonyl chloride in a solution of 1:1 diethyl ether/dichloromethane (ca. 30 mL). The reaction mixture was stirred at ambient temperature for 1 h. The reaction mixture was quenched with 10% hydrochloric acid, extracted into diethyl ether, dried ($MgSO_4$), and purified by flash chromatography (dichloromethane/diethyl ether (100:0 to 95:5 to 90:10)) to give 848 mg of the title compound as a colorless oil. $^1$H-NMR (300 MHz, $CDCl_3$) δ 7.37–7.48 (m, 5H), 6.56–6.57 (m, 1H), 6.51–6.52 (m, 1H), 6.43 (t, 1H, J=2 Hz), 5.21 (s, 1H), 4.50 (s, 2H), 2.26 (s, 3H).

b) 3-[5-Methyl-3-phenylmethylsulfonyloxy)phenoxy] propanol

A mixture of 300 mg (1.08 mmol) of 5-methyl-3-(phenylmethylsulfonyloxy)phenol, as prepared in the preceding step, 550 μL (1.1 mmol) of 2N NaOH, and 105 μL (1.12 mmol) of 3-bromopropanol, in 3 mL of tetrahydrofuran was stirred at 50° C. for 4.5 h. The reaction mixture diluted with 2N NaOH, extracted into diethyl ether, dried ($MgSO_4$), and purified by flash chromatography (dichloromethane/diethyl ether (95:5 to 90:10)) to give 171 mg (47% yield) of the title compound. $^1$H-NMR (300 MHz, $CDCl_3$; partial) δ 7.41–7.48 (m, 5H), 6.64–6.65 (m, 1H), 6.53–6.54 (m, 1H), 6.46 (t, 1H, J=2 Hz), 4.51 (s, 2H), 4.04 (t, 2H, J=6 Hz), 2.29 (s, 3H). Mass spectrum (MALDI-TOF, α-cyano-4-hydroxycinnamic acid matrix) calcd. for $C_{17}H_{20}O_5S$: 359.1 (M+Na). Found: 358.9.

c) 3-[5-Methyl-3-phenylmethylsulfonyloxy)phenoxy] propanaldehyde

At 0° C. to 171 mg (0.509 mmol) of 3-[5-methyl-3-(phenylmethylsulfonyloxy)phenoxy]propanol, as prepared in the preceding step, 200 μL (1.15 mmol) of N,N-diisopropylethylamine, and 60 μL (0.77 mmol) of anhydrous dimethyl sulfoxide in anhydrous dichloromethane was added 121 mg (0.77 mmol) of sulfur trioxide pyridine complex. The reaction mixture was stirred at 0° C. for 1 h. To the partially completed reaction mixture was added another 150 μL of N,N-diisopropylethylamine, 60 mg of sulfur trioxide pyridine complex, and 40 μL of anhydrous dimethyl sulfoxide. After 10 min, the reaction mixture was quenched with 10% aqueous citric acid solution, extracted into diethyl ether, dried ($MgSO_4$), and concentrated to give 124 mg of the title compound (73% yield) which was used directly in the next reaction. $^1$H-NMR (300 MHz, $CDCl_3$) δ 9.83 (t, 1H, J=1.5 Hz), 7.39–7.59 (m, 5H), 6.61–6.62 (m, 1H), 6.51–6.53 (m, 1H), 6.41–6.44 (m, 1H), 4.89 (s, 2H), 4.20 (t, 2H, J=6 Hz), 2.86 (td, 1H, J=1.5, 6 Hz),2.27 (s, 3H).

d) 2-[2-[5-Methyl-3-(phenylmethylsulfonyloxy)phenoxy]ethyl-1-methylene]hydrazinecarboximidamide acetate A mixture of all of 3-[5-methyl-3-(phenylmethylsulfonyloxy)phenoxy]-propionaldehyde, as prepared in the preceding step, in 2 mL of ethanol and 120 mg (0.876 mmol) of aminoguanidine nitrate was stirred for 24 h. The reaction mixture was quenched with 2N NaOH (3 mL), extracted into dichloromethane, dried ($K_2CO_3$), and concentrated. The residue was treated with 200 μL of glacial acetic acid and concentrated. The residue was then purified by flash chromatography (dichloromethane/methanol/glacial acetic acid (85:13:2 to 78:19:3)) to give 44 mg of the title compound as a gum. $^1$H-NMR (300 MHz, $CD_3OD$) δ 7.54 (t, 1H, J=5 Hz), 7.40–7.51 (m, 5H), 6.73 (s, 1H), 6.57 (s, 1H), 6.50 (t, 1H, J=2 Hz), 4.17 (t, 2H, J=2 Hz), 2.77 (q, 2H, J=6 Hz), 2.30 (s, 3H), 1.91 (s, 3H). Mass spectrum (MALDI-TOF, α-cyano-4-hydroxycinnamic acid matrix) calcd. for $C_{18}H_{22}N_4O_4S$: 391.1 (M+H). Found: 390.8.

EXAMPLE 41

2-[2-[2-[3-(2-Methoxyphenylsulfonyloxy)-5-methylphenoxy]ethyl-1-methylene]hydrazine]-1-(hydroxycarboximidamidine)

a) 3-[3-(2-Methoxyphenylsulfonyloxy)-5-methylphenoxy]propionaldehyde thiosemicarbazone A mixture of 3-[3-(2-methoxyphenylsulfonyloxy)-5-methylphenoxy-]-propionaldehyde (472.5 mg, 1.35 mmol, as prepared in step d of example 8), thiosemicarbazide (124.5 mg, 1.37 mmol) and ethanol (4.5 mL) was refluxed for 2 hours. The solution was cooled to room temperature and approximately 3 mL ethanol was removed by rotary evaporation. The residual oil in ethanol was heated to 50° C. and the product crystallized. The title compound was isolated by filtration as a white solid (493 mg, 86%). $^1$H-NMR (300 MHz, DMSO-$d_6$) δ 7.76 (ddd, 1H, J=1.8, 7.4, 8.4 Hz), 7.69 (dd, 1H, J=1.7, 7.9 Hz), 7.43 (t, 1H, J=4.8 Hz), 7.36 (d, 1H, J=8.4 Hz), 7.09 (ddd, 1H, J=0.9, 7.4, 7.8 Hz), 6.72 (br s, 1H), 6.48 (br s, 1H), 6.37 (t, 1H, J=2.3 Hz), 4.08 (t, 2H, J=6.5 Hz), 3.99 (s, 3H), 2.58 (q, 2H, J=6.4 Hz), 2.21 (s, 3H). Mass spectrum (MALDI-TOF, α-cyano-4-hydroxycinnamic acid matrix) calcd. for $C_{18}H_{21}N_3O_5S_2$: 424.1 (M+H), 446.1 (M+Na). Found: 423.9, 445.9.

b) 3-[3-(2-Methoxyphenylsulfonyloxy)-5-methylphenoxy]propionaldehyde benzylisothiosemicarbazone A solution of benzyl bromide (15.5 μL, 0.13 mmol) in tetrahydrofuran (1.5 mL) and methanol (0.5 mL) was added dropwise over 20 minutes to a mixture of 3-[3-(2-methoxyphenylsulfonyloxy)-5-methylphenoxy]-propionaldehyde thiosemicarbazone (55.3 mg, 0.13 mmol, as prepared in the preceding step) and sodium bicarbonate (28.8 mg, 0.34 mmol) in tetrahydrofuran (1.5 mL) and methanol (0.5 mL). The reaction was stirred for 5 hours at ambient temperature, then additional benzyl bromide (15.5 μL, 0.13 mmol) in tetrahydrofuran (1 mL) was added dropwise over 5 minutes. The reaction was stirred overnight at ambient temperature then concentrated to remove solvents. The residue was triturated with dichloromethane and filtered through Celite. After concentration, crude product was purified by flash column chromatography through silica gel (1:1 diethyl ether/hexane) to give the title compound as an oil (42 mg, 1:4 mixture of isomers, 62%). $^1$H-NMR (300 MHz, CDCl$_3$) δ 7.80–7.85 (m, 2H), 7.57–7.63 (m, 1H), 7.23–7.40 (m, 5H), 6.98–7.12 (m, 2H), 6.59 (br s, 1H), 6.52 (br s, 1H), 6.46 (t, 1H, J=2 Hz), 4.29 and 4.28 (s, 1H), 4.10 (t, 2H, J=6.5 Hz), 4.01 (s, 3H), 2.94 and 2.73 (q, 2H, J=6 Hz), 1.55 (s, 3H). Mass spectrum (MALDI-TOF, α-cyano-4-hydroxycinnamic acid matrix) calcd. for $C_{25}H_{27}N_3O_5S_2$: 514.1 (M+H). Found: 513.6.

c) 2-[2-[2-[3-(2-Methoxyphenylsulfonyloxy)-5-methylphenoxy]ethyl-1-methylene]hydrazine]-1-(hydroxycarboximidamidine)

A solution of hydroxylamine hydrochloride (5.9 mg, 0.08 mmol) in 15% aqueous methanol (2 mL) was added to 3-[3-(2-methoxyphenylsulfonyloxy)-5-methylphenoxy] propionaldehyde benzylisothiosemicarbazone (43.3 mg, 0.08 mmol, as prepared in the preceding step) in 15% aqueous methanol (0.3 mL) and tetrahydrofuran (0.5 mL). The solution was stirred at ambient temperature for 1 hour, then organic solvent was removed in vacuo. The residue was diluted with water and washed with diethyl ether (3×10 mL). The combined organic extracts were washed with brine, dried over Na$_2$SO$_4$, filtered and evaporated to give the title compound as an off-white solid (35.8 mg, 1:1 mixture of isomers, 100%). $^1$H-NMR (300 MHz, CDCl$_3$) δ 7.84–7.81 (m, 1H), 7.58–7.64 (m, 1H), 7.51 and 6.87 (t, 1H, J=5 Hz),7.08 (d, 1H, J=8.3 Hz), 7.02 (t, 1H, J=7.7 Hz), 6.58 (br s, 1H), 6.53 (br s, 1H), 6.44–6.47 (m, 1H), 4.02 (t, 2H, J=6.3 Hz), 4.02 (s, 3H), 2.80 and 2.63 (q, 2H, J=6 Hz), 2.24 (s, 3H).

EXAMPLE 42

2-[5-Methyl-3-[2-(methylsulfonyl) phenylsulfonyloxy]phenoxy]ethyl-1-methylene] hydrazinecarboximidamide diacetate a) 5-Methyl-3-[2-(methylsulfonyl)phenylsulfonyloxy] phenol A mixture of orcinol monohydrate (1.68 g, 12 mmol) and 2-methylsulfonylbenzenesulfonyl chloride (3.0 g, 11.8 mmol) in saturated aqueous NaHCO$_3$ (25 mL) and dichloromethane (25 mL) was stirred vigorously at room temperature for one week. The reaction mixture was diluted with 50 mL of water and extracted into dichloromethane (3×50 mL). The organic phase was washed with brine (2×50 mL) and dried over Na$_2$SO$_4$. After removing the solvent in vacuo, the residue was treated with dichloromethane and ether to initiate crystallization. The mixture was filtered to provide 1.05 g of a white solid. $^1$H-NMR (300 MHz, CDCl$_3$) δ 2.22 (s, 3H), 3.45 (s, 3H), 5.20 (s, 1H), 6.51 (t, 1H), 6.54 (s, 1H), 6.61 (s, 1H), 7.74 (td, 1H, J=1.4, 7.7 Hz), 7.87 (td, 1H, J=1.3, 7.7 Hz), 8.12 (dd, 1H, J=0.66, 7.8 Hz), and 8.44 (dd, 1H, J 0.52, 7.8 Hz).

b) 3-[5-Methyl-3-[2-(methylsufonyl)phenylsulfonyloxy] phenoxy]propanol

Diethyl azodicarboxylate (0.46 mL, 2.9 mmol) was added slowly to a solution of 1.0 g (2.9 mmol) of 5-methyl-3-[2-(methylsulfonyl)phenylsulfonyloxy]phenol, as prepared in the preceding step, 0.21 mL (2.9 mmol) of 1,3-propanediol, and 760 mg (2.9 mmol) of triphenylphosphine in anhydrous tetrahydrofuran (25 mL). The reaction mixture was stirred at ambient temperature overnight. The reaction mixture was evaporated to dryness. The residue was triturated with hexane under sonification, and the solvent was decanted (4 times). The residue was dissolved in dichloromethane and diluted with hexane to produce a crystalline material which was discarded. The filtrate was diluted with hexane to give an oil, and the solvent was decanted. The oil was dissolved in a minimum of methanol and diluted with water to initiate crystallization. The solid was collected by filtration to afford the title compound (1.16 g, quantitative yield). $^1$H-NMR (300 MHz, CDCl$_3$) δ 8.45 (dd, 1H, J=1.3, 7.8 Hz), 8.12 (dd, 1H, J=1.2, 7.8 Hz), 7.88 (td, 1H, J=1.3, 7.7 Hz), 7.74 (td, 1H, J=1.3, 7.7 Hz), 6.61–6.56 (m, 3H), 4.00 (t, 2H, J=6 Hz), 3.81 (t, 3H, J=5.9 Hz), 3.45 (s, 3H), 2.24 (s, 3H), and 1.97 (pentet, 2H). Mass spectrum (MALDI-TOF, α-cyano-4-hydroxycinnamic acid matrix) calcd. for $C_{17}H_{20}O_7S_2$: 423.1 (M+Na). Found: 423.1.

c) 3-[5-Methyl-3-[2-(methylsulfonyl)phenylsulfonyloxy] phenoxy]propionaldehyde

A solution of 3-[5-methyl-3-[2-(methylsulfonyl) phenylsulfonyloxy]-phenoxy]propanol (1.16 g, 2.9 mmol), as prepared in the preceding step, anhydrous dimethyl sulfoxide (0.62 mL, 8.7 mmol), and N,N-diisopropylethylamine (1.0 mL, 6.1 mmol) in anhydrous dichloromethane (30 mL) was treated with sulfur trioxide pyridine complex (0.97 g 6.1 mmol) at 0° C. The reaction mixture was stirred for 0.75 h before quenching with 10% aqueous citric acid (40 mL). The dichloromethane layer was separated and the aqueous layer was extracted with dichloromethane (4×40 mL). The dichloromethane layers were combined and washed with brine, dried, and evaporated to dryness. The material was used without purification in the next step.

d) 2-[5-Methyl-3-[2-(methylsulfonyl)phenylsulfonyloxy] phenoxy]ethyl-1-methylene] hydrazinecarboximidamide acetate A solution of 3-[5-methyl-3-[2-(methylsulfonyl) phenylsulfonyloxy]-phenoxy]propionaldehyde (2.9 mmol), as prepared in the preceding step, in ethanol (30 mL) was treated with aminoguanidine nitrate (0.79 g, 5.8 mmol) and stirred at ambient temperature overnight. The reaction mixture was diluted with water, and an insoluble precipitate was collected by filtration and washed with water and ether. The solid was purified on a silica gel column (10 g Waters Sep-Pak), eluting first with 10% methanol/90% dichloromethane followed by dichloromethane/methanol/acetic acid (100:25:25). The desired fractions were pooled and evaporated to a crystalline solid, which was recrystallized from ethyl acetate to give 0.268 g of the title compound as a mixture of isomers. $^1$H-NMR (300 MHz, DMSO-d$_6$) δ 8.36 (dd, 1H), 8.14–8.07 (2 dd, 2H), 7.95 (td, 1H), 7.41 (t, 0.78H), 6.78 (m, 1H), 6.61 (t, 0.16H), 6.53–6.40 (m, 1.9H), 6.23 and 6.05 (br m, 0.74H), (4.09(t) and 4.03 (t), 2H), 3.47 (s, 3H), 2.72 (q, 0.35H), and 2.60 (q, 1.43H), 2.22 (s, 2.62H) and 2.16 (s, 0.2H), and 1.83 (s, 6H). Mass spectrum (MALDI-TOF, α-cyano-4-hydroxycinnamic acid matrix) calcd. for $C_{18}H_{22}N_4O_6S_2$: 455.1 (M+H). Found: 454.9.

EXAMPLE 43

In vitro Inhibition of Purified Enzymes

Reagents

All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly-Arg-p-nitroanilide hydrochloride (Sigma B2291), N-p-Tosyl-Gly-Pro-Lys-p-nitroanilide (Sigma T6140), N-succinyl-Ala-Ala-Pro-Phe-p-nitroanilide (Sigma S7388) and N-CBZ-Val-Gly-Arg-p-nitroanilide (Sigma C7271) were obtained from Sigma. N-succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM (King of Prussia, Pa.).

Human α-thrombin, human factor Xa and human plasmin were obtained from Enzyme Research Laboratories (South Bend, Ind.). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.).

$K_i$ Determinations

All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 μL of substrate solution, 10 μL of test compound solution, and the plate allowed to thermally equilibrate at 37° C. in a Molecular Devices plate reader for >15 minutes. Reactions were initiated by the addition of a 10 μL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin

Thrombin activity was assessed as the ability to hydrolyze the substrate N-succinyl-Ala-Ala-Pro-Arg-p-nitroanilide. Substrate solutions were prepared at a concentration of 32 μM (32 μM<<Km=180 μM) in assay buffer. Final DMSO concentration was 4.3%. Purified human α-thrombin was diluted into assay buffer to a concentration of 15 nM. Final reagent concentrations were: =0.5 nM, [substrate N-succinyl-Ala-Ala-Pro-Arg-p-nitroanilide]=32 μM.

Factor X [Fxa]

Fxa activity was assessed as the ability to hydrolyze the substrate N-benzoyl-Ile-Glu-Gly-Arg-p-nitroanilide hydrochloride. Substrate solutions were prepared at a concentration of 51 μM (51<<$K_m$=1.3 mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile-Glu-Gly-Arg-p-nitroanilide hydrochloride] 51 μM.

Plasmin

Plasmin activity was assessed as the ability to hydrolyze the N-p-Tosyl-Gly-Pro-Lys-p-nitroanilide. Substrate solutions were prepared at a concentration of 37 μM (37 μM<<$K_m$=243 μM) in assay buffer. Final DMSO concentration was 4.3%. Purified human plasmin was diluted into assay buffer to a concentration of 240 nM. Final reagent concentrations were: [Plasmin]=8 nM, [N-p-Tosyl-Gly-Pro-Lys-p-nitroanilide] 37 μM.

Chymotrypsin

Chymotrypsin activity was assessed as the ability to hydrolyze N-succinyl-Ala-Ala-Pro-Phe-p-nitroanilide. Substrate solutions were prepared at a concentration of 14 μM (14 μM<<$K_m$=62 μM) in assay buffer. Final DMSO concentration was 4.3%. Purified bovine chymotrypsin was diluted into assay buffer to a concentration of 81 nM. Final reagent concentrations were: [Chymotrypsin] 2.7 nM, [N-succinyl-Ala-Ala-Pro-Phe-p-nitroanilide]=14 μM.

Trypsin

Trypsin activity was assessed as the ability to hydrolyze N-benzoyl-Phe-Val-Arg-p-nitroanilide. Substrate solutions were prepared at a concentration of 13 μM (13 μM<<$K_m$=291 μM) in assay buffer. Final DMSO concentration was 4.3%. Purified bovine trypsin was diluted into assay buffer to a concentration of 120 nM. Final reagent concentrations were: [Trypsin]=4 nM, [N-benzoyl-Phe-Val-Arg-p-nitroanilide] 13 μM.

Elastase

Elastase activity was assessed as the ability to hydrolyze N-succinyl-Ala-Ala-Pro-Val-p-nitroanilide. Substrate solutions were prepared at a concentration of 19 μM (19 μM<<$K_m$=89 μM) in assay buffer. Final DMSO concentration was 4.3%. Purified human leukocyte elastase was diluted into assay buffer to a concentration of 750 nM. Final reagent concentrations were: [Elastase]=25 nM, [N-succinyl-Ala-Ala-Pro-Val-p-nitroanilide]=19 μM.

Urokinase

Urokinase activity was assessed as the ability to hydrolyze N-CBZ-Val-Gly-Arg-p-nitroanilide. Substrate solutions were prepared at a concentration of 100 μM (100 μM<$K_m$=1.2 mM) in assay buffer. Final DMSO concentration was 4.3%. Purified human kidney urokinase was diluted into assay buffer to a concentration of 1.2 μM. Final reagent concentrations were: [Urokinase] 40 nM, and [N-CBZ-Val-Gly-Arg-p-nitroanilide]=100 μM.

A number of compounds were tested for thrombin inhibition. The results are reported in Table 1.

TABLE 1

| Example | Thrombin Ki (μM) |
| --- | --- |
| 1 | 0.0013 |
| 2 | 0.0084 |
| 3 | 0.465 |
| 4 | 1.266 |
| 5 | 0.0264 |
| 6 | 0.0136 |
| 7 | 0.0149 |
| 8 | 0.0064 |
| 9 | 0.0094 |
| 10 | 0.0172 |
| 11 | 0.0296 |
| 12 | 0.0089 |
| 13 | 0.014 |
| 14 | 0.0475 |
| 15 | 0.0107 |
| 16 | 0.0213 |
| 17 | 0.0062 |
| 18 | 0.0047 |
| 19 | 0.014 |
| 20 | 0.0762 |
| 21 | 0.0036 |
| 22 | 0.0636 |
| 23 | 1.673 |
| 24 | 0.0135 |
| 25 | 0.0632 |
| 26 | 1.545 |
| 27 | 0.298 |
| 28 | 0.1861 |
| 30 | 0.0334 |
| 31 | 0.0692 |
| 32 | 0.0249 |
| 34 | 0.056 |
| 35 | 0.031 |
| 36 | 0.068 |
| 39 | 0.052 |

The compound of Example 1 was screened for proteolytic inhibition. The results are given in Table 2.

TABLE 2

| Enzyme | $K_i$ or % Inhibition at Concentration (μM) |
| --- | --- |
| thrombin | $K_i$ = 13 nM |
| chymotrypsin | 0% at 1.6 μM |
| trypsin | 0% at 1.6 μM |
| elastase | 0% at 1.6 μM |
| urokinase | 0% at 1.6 μM |
| plasmin | 0% at 1.6 μM |
| Factor Xa | 0% at 1.6 μM |

The results indicate that the compounds of the present invention are potent inhibitors of seriene proteases, including thrombin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the Formula I:

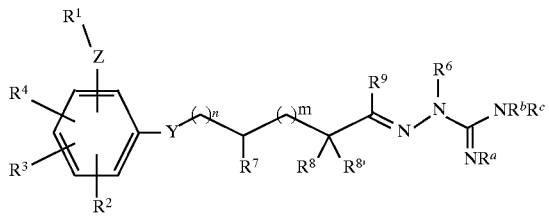

or solvates, hydrates or pharmaceutically acceptable salts thereof, wherein:

$R^1$ is one of cycloalkyl, alkenyl, alkynyl, aryl, aralkyl or heteroaryl, any of which may be optionally substituted;

Z is one of —$NR^{10}SO_2$—, —$SO_2NR^{10}$—, —$NR^{10}C(R^yR^z)$—, —$C(R^yR^z)NR^{10}$—, —$OSO_2$—, —$SO_2O$—, —$OC(R^yR^z)$—, —$C(R^yR^z)O$—, —$NR^{10}CO$— or —$CONR^{10}$—;

$R^y$ and $R^z$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy;

$R^2$, $R^3$ and $R^4$ are each independently one of hydrogen, alkyl, cycloalkyl, alkenyl, alkynyl, aryl, aralkyl, heteroaryl, trifluoromethyl, halogen, hydroxyalkyl, cyano, nitro, carboxamido, —$CO_2R^x$, —$CH_2OR^x$ or —$OR^x$, or when present on adjacent carbon atoms, $R^2$ and $R^3$ may also be taken together to form one of —CH=CH—CH=CH— or —$(CH_2)_q$—, where q is from 2 to 6;

$R^x$, in each instance, is independently one of hydrogen, alkyl or cycloalkyl wherein said alkyl or cycloalkyl groups may optionally have one or more unsaturations;

Y is one of —O—, —$NR^{10}$—, —S—, —$CHR^{10}$— or a covalent bond;

$R^a$, $R^b$ and $R^c$ are independently hydrogen, alkyl, hydroxy, alkoxy, aryloxy, aralkoxy, alkoxycarbonyloxy, cyano or —$CO_2R^w$;

$R^w$ is alkyl, cycloalkyl, phenyl, benzyl,

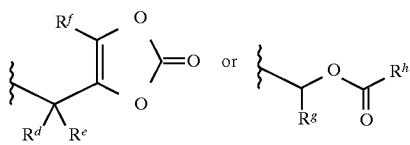

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

$R^6$ is one of hydrogen, alkyl, aralkyl, aryl, amino, hydroxyalkyl, aminoalkyl, monoalkylamino($C_{2-10}$)alkyl, dialkylamino($C_{2-10}$)alkyl or carboxyalkyl;

$R^7$ and $R^8$ are each independently one of hydrogen, alkyl, aralkyl, aryl, hydroxyalkyl or carboxyalkyl, and $R^{8'}$ is hydrogen; or $R^7$ and $R^8$ are taken together to form —$(CH_2)_y$—, where y is zero, 1 or 2, and $R^{8'}$ is hydrogen; or $R^7$ is hydrogen, and $R^8$ and $R^{8'}$ are taken together to form —$(CH_2)_t$—, where t is from 2 to 5;

$R^9$ is one of hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^{10}$, in each instance, is independently one of hydrogen, alkyl, aralkyl, aryl, hydroxyalkyl, aminoalkyl, monoalkylamino($C_{2-10}$)alkyl, dialkylamino($C_{2-10}$) alkyl, carboxyalkyl or alkoxycarbonylalkyl;

n is from zero to 8; and m is from zero to 4.

2. A compound of claim 1, wherein $R^1$ is one of $C_{4-7}$ cycloalkyl, $C_{2-8}$ alkenyl, $C_{2-8}$ alkynyl or $C_{6-14}$ aryl, any of which is optionally substituted.

3. A compound of claim 1, wherein $R^1$ is heteroaryl, optionally substituted by one or more of hydroxy, nitro, trifluoromethyl, halogen, $C_1$-alkoxy, $C_{1-6}$alkyl, amino, mono($C_1$-)alkylamino, di($C_{1-6}$)alkylamino, cyano, amidino, guanidino, carboxyalkoxy, trifluoromethoxy or perfluoroethoxy.

4. A compound of claim 1, wherein $R^1$ is pyridyl, pyrazolyl, thiophenyl, chromenyl, benzoxazolyl, benzthiadiazolyl, quinazolinyl, quinolinyl, isoquinolinyl or tetrahydroquinolinyl, any of which is optionally substituted by one or more substituents independently selected from the group consisting of hydroxy, nitro, trifluoromethyl, halogen, $C_{1-6}$-alkoxy, $C_{1-6}$alkyl, amino, mono($C_{1-6}$)alkylamino, di($C_{1-6}$)alkylamino, cyano, amidino, guanidino, carboxyalkoxy, trifluoromethoxy and perfluoroethoxy.

5. A compound of claim 1, wherein Z is $-SO_2NR^{10}-$, $-SO_2O-$ or $-CH_2O-$.

6. A compound of claim 1, wherein Y is one of $-O-$ or $-NR^{10}-$, and $R^{10}$ in each instance is one of hydrogen, $C_{1-6}$alkyl, benzyl, phenethyl, $C_{2-10}$hydroxyalkyl or $C_{2-7}$carboxyalkyl.

7. A compound of claim 6, wherein Y is $-O-$.

8. A compound of claim 1, wherein $R^a$, $R^b$ and $R^c$ are hydrogen.

9. A compound of claim 1, wherein $R^7$ and $R^8$ are independently hydrogen, $C_{1-6}$alkyl, $C_{6-10}$ar($C_{1-6}$)alkyl, $C_{6-10}$aryl, $C_{2-10}$hydroxyalkyl or $C_{2-7}$carboxyalkyl, and $R^{8'}$ is hydrogen.

10. A compound of claim 1, wherein $R^7$ and $R^8$ are taken together to form $-(CH_2)_y-$, and y is 0, 1 or 2; and $R^{8'}$ is hydrogen.

11. A compound of claim 1, wherein $R^7$ is hydrogen, and $R^8$ and $R^{8'}$ are taken together to form $-(CH_2)_t-$, and t is 2.

12. A compound of claim 1, wherein n is from 0 to 4.

13. A compound of claim 1, wherein m is zero, 1, 2 or 3.

14. A compound of claim 1, wherein m and n are each zero and $R^7$, $R^8$ and $R^{8'}$ are each hydrogen.

15. A compound of claim 1, wherein $R^2$ and $R^4$ are hydrogen and $R^3$ is methyl.

16. A compound of claim 1, wherein:

Z is one of $-SO_2O-$, $-SO_2NR^{10}-$, $-CH_2O-$ or $-OCH_2-$;

$R^1$ is one of phenyl or naphthyl, optionally substituted by one or two of chloro, trifluoromethyl, amino or dimethylamino;

$R^2$ and $R^3$ are each hydrogen or $R^2$ and $R^3$ may also be taken together to form $-CH=CH-CH=CH-$;

$R^4$ is one of hydrogen, methyl, methoxy or trifluoromethyl;

Y is one of O, $NR^{10}$, or a covalent bond;

$R^a$, $R^b$ and $R^c$ are each hydrogen or hydroxy,

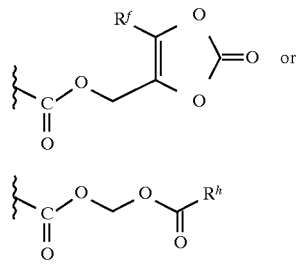

where $R^h$ is benzyl or t-butyl, and where $R^f$ is hydrogen or methyl;

$R^6$ is one of hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$) alkyl, or methylamino($C_{2-8}$)alkyl;

$R^7$ and $R^8$ are independently one of hydrogen, $C_{1-6}$ alkyl, $C_{2-10}$ hydroxyalkyl or $C_{2-10}$ carboxyalkyl, or $R^7$ and $R^8$ are taken together to form $-(CH_2)_y-$, where y is zero, 1 or 2;

$R^9$ is hydrogen or $C_{1-4}$ alkyl;

$R^{10}$, in each instance, is independently hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, methylamino($C_{2-8}$)alkyl;

n is from zero to 4; and m is zero, 1, 2 or 3.

17. A compound having the formula:

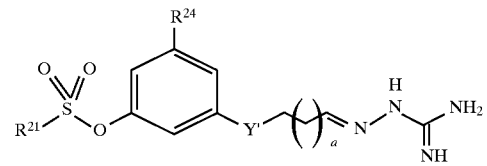

or solvate, hydrate, pharmaceutically acceptable salt or prodrug thereof; wherein $R^{21}$ is one of phenyl, naphthyl, thiophenyl, pyridyl, pyrazolyl, benzthiadiazolyl, quinolinyl, or isoquinolinyl, any of which optionally substituted by one, two or three substituents independently selected from the group consisting of fluoro, chloro, bromo, $C_{1-4}$ alkyl, $C_{1-4}$ alkoxy, trifluoromethyl, cyano, nitro, amino or dimethylamino;

$R^{24}$ is hydrogen or $C_{1-4}$ alkyl;

Y' is one of O, NH or a covalent bond; and a is 0, 1 or 2.

18. A compound having the formula:

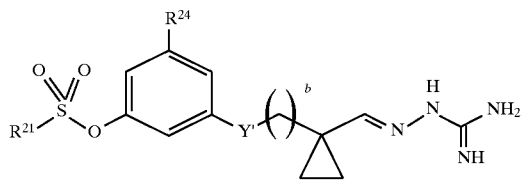

or a solvate, hydrate, pharmaceutically acceptable salt or prodrug thereof; wherein $R^{21}$ is one of phenyl, naphthyl, thiophenyl, pyridyl, pyrazolyl, benzthiadiazolyl, quinolinyl, or isoquinolinyl, any of which optionally substituted by one, two or three substituents independently selected from the group consisting of fluoro, chloro, bromo, $C_{1-4}$ alkyl, $C_{1-4}$ alkoxy, trifluoromethyl, cyano, nitro, amino or dimethylamino;

$R^{24}$ is hydrogen or $C_{1-4}$ alkyl;

Y' is one of O, NH or a covalent bond; and b is 0, 1 or 2.

19. The compound of claim 1, which is:

2-[2-[3-(2-chlorophenylsulfonyloxy)-5-methylphenoxy] ethyl-1-methylene]-hydrazinecarboximidamide hydrochloride;

2-[2-[5-methyl-3-(2-trifluoromethylphenylsulfonyloxy) phenoxy]ethyl-1-methylene]hydrazinecarboximidamide nitrate;

2-[3-[3-($^2$-chlorophenylsulfonyloxy)-5-methoxyphenyl] propyl-1-methylene]-hydrazinecarboximidamide hydrochloride;

2-[2-[3-(2,3-dichlorophenylsulfonyloxy)-5-methylphenoxy] ethyl-1-methylene]hydrazinecarboximidamide nitrate;

2-[2-[3-(2,5-dichlorophenylsulfonyloxy)-5-methylphenoxy] ethyl-1-methylene]hydrazinecarboximidamide nitrate;

2-[2-[3-(2-methoxyphenylsulfonyloxy)-5-methylphenoxy] ethyl-1-methylene]hydrazinecarboximidamide acetate;

2-[2-[3-(5-bromo-2-methoxyphenylsulfonyloxy)-5-methylphenoxy]ethyl-1-methylene] hydrazinecarboximidamide nitrate;

2-[2-[5-methyl-3-(2-trifluoromethoxyphenylsulfonyloxy) phenoxy]ethyl-1-methylene]hydrazinecarboximidamide nitrate;

2-[2-[5-methyl-3-(3-methylphenylsulfonyloxy)phenoxy] ethyl-1-methylene]-hydrazinecarboximidamide nitrate;

2-[2-[3-(2-cyanophenylsulfonyloxy)-5-methylphenoxy] ethyl-1-methylene]-hydrazinecarboximidamide hydrochloride;

2-[2-[3-(2-methoxy-5-methylphenylsulfonyloxy)-5-methylphenoxy]ethyl-1-methylene] hydrazinecarboximidamide nitrate;

2-[2-[3-(2,5-dimethoxyphenylsulfonyloxy)-5-methylphenoxy]ethyl-1-methylene] hydrazinecarboximidamide nitrate;

2-[2-[3-(2,5-dimethylphenylsulfonyloxy)-5-methylphenoxy]ethyl-1-methylene] hydrazinecarboximidamide nitrate;

2-[2-[3-(5-chloro-2-methoxyphenylsulfonyloxy)-5-methylphenoxy]ethyl-1-methylene] hydrazinecarboximidamide hydrochloride;

2-[2-[3-(3-chlorophenylsulfonyloxy)-5-methylphenoxy] ethyl-1-methylene]-hydrazinecarboximidamide nitrate;

2-[2-[5-methyl-3-(2-methyl-5-nitrophenylsulfonyloxy) phenoxy]ethyl-1-methylene]hydrazinecarboximidamide nitrate;

2-[2-[3-(5-fluoro-2-methylphenylsulfonyloxy)-5-methylphenoxy]ethyl-1-methylene] hydrazinecarboximidamide nitrate;

2-[2-[3-(2-chloro-5-trifluoromethylphenylsulfonyloxy)-5-methylphenoxy]-ethyl-1-methylene] hydrazinecarboximidamide nitrate;

2-amino-[2-[2-[3-(5-chloro-2-methoxyphenylsulfonyloxy)-5-methylphenoxy]-ethyl-1-methylene]hydrazine] carboximidamine acetate;

2-[2-[3-(2-cyano-5-methylphenylsulfonyloxy)-5-methylphenoxy]ethyl-1-methylene] hydrazinecarboximidamide nitrate;

2-[2-[3-(3-fluorophenylsulfonyloxy)-5-methylphenoxy] ethyl-1-methylene]-hydrazinecarboximidamide nitrate;

2-[2-[3-(3-cyanophenylsulfonyloxy)-5-methylphenoxy] ethyl-1-methylene]-hydrazinecarboximidamide nitrate;

2-[2-[3-(3-bromophenylsulfonyloxy)-5-methylphenoxy] ethyl-1-methylene]-hydrazinecarboximidamide nitrate;

2-[2-[5-methyl-3-(2-nitrophenylsulfonyloxy)phenoxy] ethyl-1-methylene]-hydrazinecarboximidamide nitrate; and 2-[2-[5-methyl-3-(2-nitrophenylsulfonyloxy)phenoxy] ethyl-1-methylene]-hydrazinecarboximidamide nitrate.

20. The compound of claim 1, which is:

2-[2-[5-methyl-3-(2-trifluoromethylbenzyloxy)phenoxy] ethyl-1-methylene]-hydrazinecarboximidamide nitrate;

2-[2-[(5-methyl-3-(N-(5-ethoxycarbonylpentyl)-N-(2-trifluoromethylphenylsulfonyl)amino)phenoxy]ethyl-1-methylene]hydrazinecarboximidamide nitrate;

2-[2-[3-(benzo-2,1,3-thiadiazole-4-sulfonyloxy)-5-methylphenoxy]ethyl-1-methylene] hydrazinecarboximidamide nitrate;

2-[2-[5-methyl-3-(quinolinyl-8-sulfonyloxy)phenoxy]ethyl-1-methylene]-hydrazinecarboximidamide acetate;

2-[2-[3-(5-chlorothiophenyl-2-sulfonyloxy)-5-methylphenoxy]ethyl-1-methylene] hydrazinecarboximidamide nitrate;

2-[2-[3-(5-chloro-1,3-dimethylpyrazole-4-sulfonyloxy)-5-methylphenoxy]-ethyl-1-methylene] hydrazinecarboximidamide acetate;

2-[3-[3-(2-methoxyphenylsulfonyloxy)-5-methylphenoxy] propyl-1-methylene]hydrazinecarboximidamide nitrate;

2-[2-[5-methyl-3-(1-naphthalenylsulfonyloxy)phenoxy] ethyl-1-methylene]-hydrazinecarboximidamide nitrate;

1-amino-2-[2-[3-(5-chloro-2-methoxyphenylsulfonyloxy)-5-methylphenoxy]-ethyl-1-methylene] hydrazinecarboximidamine acetate;

2-[3-(2-methoxyphenylsulfonyloxy)-5-methylphenoxy] methyl-1-methylene]-hydrazinecarboximidamide nitrate;

2-[2-[(3-methyl-5-(N-(4-phenylbutyl)-N-(2-trifluoromethylphenylsulfonyl))-amino)phenoxy]ethyl-1-methylene]hydrazinecarboximidamide acetate;

2-[2-[3-(5-isoquinolinylsulfonyloxy)-5-methylphenoxy] ethyl-1-methylene]-hydrazinecarboximidamide nitrate;

2-[[1-[5-methyl-3-(quinolinyl-8-sulfonyloxy)phenoxy] methyl]cyclopropyl-1-methylene] hydrazinecarboximidamide acetate;

2-[2-[5-methyl-3-(3-pyridinylsulfonyloxy)phenoxy]ethyl-1-methylene]-hydrazinecarboximidamide diacetate;

2-[[1-[3-(2-cyanophenylsulfonyloxy)-5-methylphenoxy] methyl]cyclopropyl-1-methylene] hydrazinecarboximidamide acetate;

2-[2-[5-methyl-3-(phenylmethylsulfonyloxy)phenoxy] ethyl-1-methylene]-hydrazinecarboximidamide acetate;

2-[2-[2-[3-(2-methoxyphenylsulfonyloxy)-5-methylphenoxy]ethyl-1-methylene]hydrazine]-1-(hydroxycarboximidamidine); and 2-[5-methyl-3-[2-(methylsulfonyl)phenylsulfonyloxy] phenoxy]ethyl-1-methylene]hydrazinecarboximidamide diacetate.

21. A compound having the Formula I:

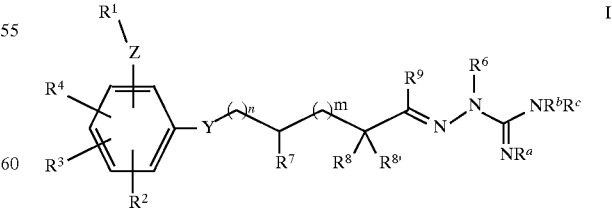

or a solvate, hydrate or pharmaceutically acceptable salt thereof; wherein:

$R^1$ is one of alkyl, cycloalkyl, alkenyl, alkynyl, aryl, aralkyl or heteroaryl, any of which may be optionally substituted;

Z is one of —NR$^{10}$SO$_2$—, —SO$_2$NR$^{10}$—, —NR$^{10}$C(R$^y$R$^z$)—, —C(R$^y$R$^z$)NR$^{10}$—, —OSO$_2$—, —SO$_2$O—, —OC(R$^y$R$^z$)—, —C(R$^y$R$^z$O)—, —NR$^{10}$CO— or —CONR$^{10}$—;

R$^y$ and R$^z$ are each independently one of hydrogen, alkyl, cycloalkyl, aryl, aralkyl, hydroxyalkyl, carboxyalkyl, aminoalkyl, monoalkylaminoalkyl, dialkylaminoalkyl or carboxy;

R$^2$, R$^3$ and R$^4$ are each independently one of hydrogen, alkyl, cycloalkyl, alkenyl, alkynyl, aryl, aralkyl, heteroaryl, trifluoromethyl, halogen, hydroxyalkyl, cyano, nitro, carboxamido, —CO$_2$R$^x$, —CH$_2$OR$^x$ or —OR$^x$, or when present on adjacent carbon atoms, R$^2$ and R$^3$ may also be taken together to form one of —CH=CH—CH=CH— or —(CH$_2$)$_q$—, where q is from 2 to 6;

R$^x$, in each instance, is independently one of hydrogen, alkyl or cycloalkyl wherein said alkyl or cycloalkyl groups may optionally have one or more unsaturations;

Y is one of —O—, —NR$^{10}$—, —S—, —CHR$^{10}$— or a covalent bond;

R$^w$ is alkyl, cycloalkyl, phenyl, benzyl,

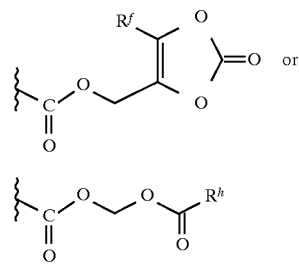

where R$^d$ and R$^e$ are independently hydrogen, C$_{1-6}$ alkyl, C$_{2-6}$ alkenyl or phenyl, R$^f$ is hydrogen or methyl, R$^g$ is hydrogen, C$_{1-6}$ alkyl, C$_{2-6}$ alkenyl or phenyl, and R$^h$ is benzyl or t-butyl; and:

A. R$^7$ and R$^9$ are taken together to form —(CH$_2$)$_o$—, where o is 1, 2 or 3;

R$^8$ is hydrogen, alkyl, aralkyl, aryl, hydroxyalkyl or carboxyalkyl; R$^{8'}$ is hydrogen;

R$^a$, R$^b$ and R$^c$ are hydrogen, hydroxy,

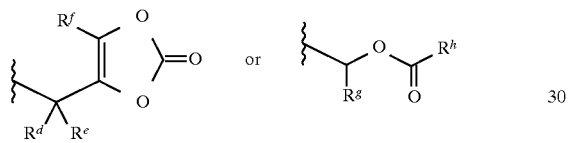

where R$^h$ is benzyl or t-butyl, and where R$^f$ is hydrogen or methyl; and R$^6$ is hydrogen, C$_{1-4}$ alkyl, C$_{2-4}$ hydroxyalkyl, C$_{2-4}$ carboxyalkyl, C$_{2-4}$ aminoalkyl, dimethylamino(C$_{2-8}$)alkyl, or methylamino(C$_{2-8}$)alkyl; or B. R$^7$ is hydrogen, alkyl, aralkyl, aryl, hydroxyalkyl or carboxyalkyl;

R$^8$ and R$^9$ are taken together to form —CH$_2$—CH$_2$—(CH$_2$)$_p$—, where p is 1, 2 or 3;

R$^{8'}$ is hydrogen; and

R$^a$, R$^b$ and R$^c$ are hydrogen, hydroxy,

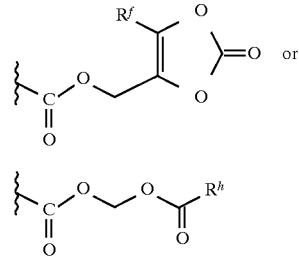

where R$^h$ is benzyl or t-butyl, and where R$^f$ is hydrogen or methyl; and R$^6$ is hydrogen, C$_{1-4}$ alkyl, C$_{2-4}$ hydroxyalkyl, C$_{2-4}$ carboxyalkyl, C$_{2-4}$ aminoalkyl, dimethylamino(C$_{2-8}$)alkyl, or methylamino(C$_{2-8}$)alkyl; or C. R$^6$ and R$^b$ are taken together to form =CH—N=CH—NH— or —CH$_2$—(CH$_2$)$_r$—, where r is 1, 2 or 3; R$^a$ is hydrogen or hydroxy;

R$^c$ is hydrogen, alkyl, hydroxy, alkoxy, aryloxy, aralkoxy, alkoxycarbamoyloxy, cyano or —CO$_2$R$^w$, where R$^w$ is as defined above; R$^7$ and R$^8$ are each independently one of hydrogen, alkyl, aralkyl, aryl, hydroxyalkyl or carboxyalkyl, or R$^7$ and R$^8$ are taken together to form —(CH$_2$)$_y$—, where y is zero, 1 or 2; R$^{8'}$ is hydrogen; and R$^9$ is one of hydrogen, alkyl, cycloalkyl or aryl, wherein said alkyl, cycloalkyl or aryl may be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl; or D. R$^a$ and R$^c$ are taken together to form —CH$_2$—(CH$_2$)$_s$—, where s is 1 or 2;

R$^b$ is hydrogen, hydroxy

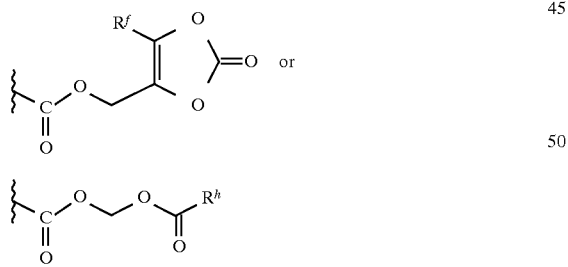

where R$^h$ is benzyl or t-butyl and where R$^f$ is hydrogen or methyl; and

R$^6$ is hydrogen, alkyl, alkoxy, aryloxy, aralkoxy, alkoxycarbonyloxy, cyano or —CO$_2$R$^w$, where R$^w$ is as defined above; R$^7$ and R$^8$ are each independently one of hydrogen, alkyl, aralkyl, aryl, hydroxyalkyl or carboxyalkyl, or R$^7$ and R$^8$ are taken together to form —(CH$_2$)$_y$—, where y is zero, 1 or 2; R$^{8'}$ is hydrogen; and R$^9$ is one of hydrogen, alkyl, cycloalkyl or aryl, wherein said alkyl, cycloalkyl or aryl may be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl.

22. A pharmaceutical composition for inhibiting proteolysis in a mammal, comprising an amount of a compound of claim 1 effective to inhibit proteolysis; and a pharmaceutically acceptable carrier or diluent.

23. The pharmaceutical composition of claim 22 wherein said compound is present in an effective amount to inhibit a trypsin-like protease.

24. A pharmaceutical composition for inhibiting proteolysis in a mammal, comprising an amount of a compound of claim 1 effective to inhibit proteolysis; and a pharmaceutically acceptable carrier or diluent.

25. A pharmaceutical composition for inhibiting proteolysis in a mammal, comprising an amount of a compound of claim 16 effective to inhibit proteolysis; and a pharmaceutically acceptable carrier or diluent.

26. A pharmaceutical composition for inhibiting proteolysis in a mammal, comprising an amount of a compound of claim 17 effective to inhibit proteolysis; and a pharmaceutically acceptable carrier or diluent.

27. A pharmaceutical composition for inhibiting proteolysis in a mammal, comprising an amount of a compound of claim 18 effective to inhibit proteolysis; and a pharmaceutically acceptable carrier or diluent.

28. A pharmaceutical composition for inhibiting proteolysis in a mammal, comprising an amount of a compound of claim 19 effective to inhibit proteolysis; and a pharmaceutically acceptable carrier or diluent.

29. A pharmaceutical composition for inhibiting proteolysis in a mammal, comprising an amount of a compound of claim 21 effective to inhibit proteolysis; and a pharmaceutically acceptable carrier or diluent.

30. A method of inhibiting proteolysis in a mammal, comprising administering to the mammal a composition of claim 22.

31. The method of claim 30, wherein a trypsin-like protease is inhibited.

32. A method of treating pancreatitis, thrombosis, ischemia, stroke, restenosis, emphysema or inflammation in a mammal, comprising administering to the mammal a composition of claim 22.

33. A method of inhibiting thrombin-induced platelet aggregation and clotting of fibrinogen in plasma, comprising administering to the mammal a composition of claim 22.

34. A method of inhibiting proteolysis in a mammal, comprising administering to the mammal a composition of claim 24.

35. The method of claim 24, wherein a trypsin-like protease is inhibited.

36. A method of treating pancreatitis, thrombosis, ischemia, stroke, restenosis, emphysema or inflammation in a mammal, comprising administering to the mammal a composition of claim 24.

37. A method of inhibiting thrombin-induced platelet aggregation and clotting of fibrinogen in plasma, comprising administering to the mammal a composition of claim 24.

38. A method of inhibiting proteolysis in a mammal, comprising administering to the mammal a composition of claim 25.

39. The method of claim 38 wherein a trypsin-like protease is inhibited.

40. A method of treating pancreatitis, thrombosis, ischemia, stroke, restenosis, emphysema or inflammation in a mammal, comprising administering to the mammal a composition of claim 25.

41. A method of inhibiting thrombin-induced platelet aggregation and clotting of fibrinogen in plasma, comprising administering to the mammal a composition of claim 25.

42. A method of inhibiting proteolysis in a mammal, comprising administering to the mammal a composition of claim 26.

43. The method of claim 42, wherein a trypsin-like protease is inhibited.

44. A method of treating pancreatitis, thrombosis, ischemia, stroke, restenosis, emphysema or inflammation in a mammal, comprising administering to the mammal a composition of claim 26.

45. A method of inhibiting thrombin-induced platelet aggregation and clotting of fibrinogen in plasma, comprising administering to the mammal a composition of claim 26.

46. A method of inhibiting proteolysis in a mammal, comprising administering to the mammal a composition of claim 27.

47. The method of claim 46, wherein a trypsin-like protease is inhibited.

48. A method of treating pancreatitis, thrombosis, ischemia, stroke, restenosis, emphysema or inflammation in a mammal, comprising administering to the mammal a composition of claim 27.

49. A method of inhibiting thrombin-induced platelet aggregation and clotting of fibrinogen in plasma, comprising administering to the mammal a composition of claim 27.

50. A method of inhibiting proteolysis in a mammal, comprising administering to the mammal a composition of claim 28.

51. The method of claim 50, wherein a trypsin-like protease is inhibited.

52. A method of treating pancreatitis, thrombosis, ischemia, stroke, restenosis, emphysema or inflammation in a mammal, comprising administering to the mammal a composition of claim 28.

53. A method of inhibiting thrombin-induced platelet aggregation and clotting of fibrinogen in plasma, comprising administering to the mammal a composition of claim 28.

54. A method of inhibiting proteolysis in a mammal, comprising administering to the mammal a composition of claim 29.

55. The method of claim 54, wherein a trypsin-like protease is inhibited.

56. A method of treating pancreatitis, thrombosis, ischemia, stroke, restenosis, emphysema or inflammation in a mammal, comprising administering to the mammal a composition of claim 29.

57. A method of inhibiting thrombin-induced platelet aggregation and clotting of fibrinogen in plasma, comprising administering to the mammal a composition of claim 29.

58. A process for preparing an amidinohydrazone compound of claim 1, comprising reacting an aminoguanidine of Formula II:

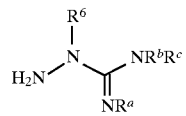

or a salt thereof, wherein $R^6$, $R^a$, $R^b$ and $R^c$ are defined in claim 1, with a carbonyl-containing compound of the formula

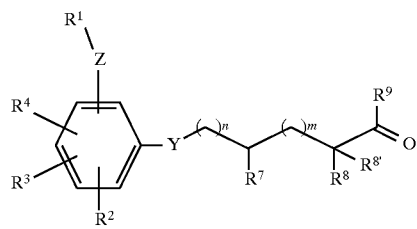

wherein $R^1$–$R^4$, Z, Y n, m, and $R^6$–$R^9$ are as defined in claim 1.

59. The process of claim 58, wherein the aminoguanidine of Formula II is provided as a hydrochloride, acetate or nitrate salt.

60. The process of claim 58, wherein the reaction is conducted at ambient temperature using an alcohol as a solvent.

61. The process of claim 58, wherein an acid is added to the reaction mixture.

62. The process of claim 58, wherein $R^1$ is heteroaryl, optionally substituted by one or more of hydroxy, nitro, trifluoromethyl, halogen, $C_{1-6}$alkoxy, $C_{1-6}$alkyl, amino, mono($C_{1-6}$)alkylamino, di($C_{1-6}$)alkylamino, cyano, amidino, guanidino, carboxyalkoxy, trifluoromethoxy or perfluoroethoxy.

63. The process of claim 62, wherein R' pyridyl, pyrazolyl, thiophenyl, chromenyl, benzoxazolyl, benzthiadiazolyl, quinazolinyl, quinolinyl, isoquinolinyl and tetrahydroquinolinyl, any of which is optionally substituted by one or more substituents independently selected from the group consisting of hydroxy, nitro, trifluoromethyl, halogen, $C_{1-6}$alkoxy, $C_{1-6}$alkyl, amino, mono($C_{1-6}$)alkylamino, di($C_{1-6}$)alkylamino, cyano, amidino, guanidino, carboxyalkoxy, trifluoromethoxy and perfluoroethoxy.

64. The process of claim 58, wherein Z is —$SO_2NR^{10}$—, —$SO_2O$— or —$CH_2O$—.

65. The process of claim 58, wherein Y is one of —O— or —$NR^{10}$—, and $R^{10}$ in each instance is one of hydrogen, $C_{1-6}$alkyl, benzyl, phenethyl, $C_{2-10}$hydroxyalkyl or $C_{2-7}$carboxyalkyl.

66. The process of claim 65, wherein Y is —O—.

67. The process of claim 58, wherein $R^a$, $R^b$ and $R^c$ are hydrogen.

68. The process of claim 58, wherein $R^7$ and $R^8$ are independently hydrogen, $C_{2-7}$alkyl, $C_{6-10}$ar($C_{1-6}$)alkyl, $C_{6-10}$aryl, $C_{2-10}$hydroxyalkyl or $C_{2-7}$carboxyalkyl, and $R^{8'}$ is hydrogen.

69. The process of claim 58, wherein $R^7$ and $R^8$ are taken together to form —$(CH_2)_y$—, and y is 0, 1 or 2; and $R^{8'}$ is hydrogen.

70. The process of claim 58, wherein $R^7$ is hydrogen, and $R^8$ and $R^{8'}$ are taken together to form —$(CH_2)_t$—, and t is 2.

71. The process of claim 58, wherein n is from 0 to 4 and m is zero, 1, 2 or 3.

72. The process of claim 58, wherein m and n are each zero and $R^7$, $R^8$ and $R^{8'}$ are each hydrogen.

73. The process of claim 72, wherein $R^2$ and $R^4$ are hydrogen and $R^3$ is methyl.

74. A compound of claim 1, wherein $R^1$ is $C_{6-10}$aryl, optionally substituted by one or more substituents independently selected from the group consisting of hydroxy; nitro; trifluoromethyl; halogen; alkyl; alkoxy; aminoalkoxy; aminoalkyl; hydroxyalkyl; hydroxyalkoxy; cyano; aryl; amino; monoalkylamino; dialkylamino; carboxy; carboxyalkyl; carboxyalkoxy; mono(hydroxyalkyl)amino; di(hydroxyalkyl) amino; mono(carboxyalkyl)amino; di(carboxyalkyl)amino; alkoxycarbonylamino; alkoxycarbonyl; aralkoxycarbonyl; alkenylcarbonyl; alkynylcarbonyl; alkylsulfonyl; alkenylsulfonyl; alkynylsulfonyl; arylsulfonyl; aralkylsulfonyl; mono- and di-(alkyl)aminosulfonyl; mono- and di-(aryl) aminosulfonyl; mono- and di-(aralkyl)aminosulfonyl; alkylsulfinyl; alkylsulfonamido; arylsulfonamido; aralkylsulfonamido; N-morpholinosulfonyl; N-piperazinylsulfonyl, optionally substituted in the 4-position with alkyl, hydroxyalkyl, aryl, arylalkyl, alkylsulfonyl, arylsufonyl, alkylcarbonyl or arylcarbonyl; N-pyrrolylsulfonyl; N-piperidinylsulfonyl; N-pyrrolidinylsulfonyl; N-dihydropyridylsulfonyl; N-indolylsulfonyl; amidino; guanidino; alkyliminoamino; formyliminoamino; trifluoromethoxy and perfluoroethoxy.

75. A compound of claim 1, wherein:
Z is one of —$SO_2O$—, —$SO_2NR^{10}$—, —$C(R^yR^z)O$— or —$OC(R^yR^z)$—, where $R^y$ and $R^z$ are each hydrogen;
$R^1$ is one of $C_{6-10}$ aryl, pyridinyl, thiophenyl, quinazolinyl, quinolinyl or tetrahydroquinolinyl, any of which is optionally substituted by one or two of hydroxy; nitro; trifluoromethyl; halogen; $C_{1-6}$ alkyl; $C_{6-10}$ aryl; $C_{1-6}$ alkoxy; $C_{1-6}$ aminoalkyl; $C_{1-6}$ aminoalkoxy; amino; mono($C_{1-4}$)alkylamino; di($C_{1-4}$) alkylamino; $C_{2-6}$ alkoxycarbonylamino; $C_{2-6}$ alkoxycarbonyl; carboxy; $C_{1-6}$ hydroxyalkyl; $C_{2-6}$ hydroxyalkoxy; $C_{2-10}$ mono(carboxyalkyl)amino; di($C_{2-10}$ carboxyalkyl)amino; $C_{6-14}$ ar($C_{1-6}$) alkoxycarbonyl; $C_{2-6}$ alkynylcarbonyl; $C_{1-6}$ alkylsulfonyl; $C_{2-6}$ alkenylsulfonyl; $C_{2-6}$ alkynylsulfonyl; $C_{6-10}$ arylsulfonyl; $C_{6-10}$ ar($C_{1-6}$) alkylsulfonyl; mono- and di-(($C_{1-4}$)alkyl)aminosulfonyl; mono- and di- (($C_{6-10}$)aryl) aminosulfonyl; mono- and di-($C_{6-10}$ ar($C_{1-4}$)alkyl) aminosulfonyl; $C_{1-6}$ alkylsulfinyl; $C_{1-6}$ alkylsulfonamido; $C_{6-10}$ arylsulfonamido; $C_{6-10}$ ar($C_{1-6}$) alkylsulfonamido; N-morpholinosulfonyl; N-piperazinylsulfonyl, optionally substituted in the 4-position with $C_{6-10}$ alkyl, $C_{1-6}$ hydroxyalkyl, $C_{6-10}$ aryl, $C_{6-10}$ aryl($C_{1-6}$)alkyl, $C_{1-6}$ alkylsulfonyl, $C_{6-10}$ arylsulfonyl, $C_{1-6}$ alkylcarbonyl or $C_{6-10}$ arylcarbonyl; N-pyrrolylsulfonyl; N-piperidinylsulfonyl; N-pyrrolidinylsulfonyl; N-dihydropyridylsulfonyl; N-indolylsulfonyl; amidino; guanidino; $C_{1-6}$ alkyliminoamino; formyliminoamino; $C_{2-6}$ carboxyalkoxy; $C_{2-6}$ carboxyalkyl; carboxyalkylamino; cyano; trifluoromethoxy or perfluoroethoxy;
$R^2$, $R^3$ and $R^4$ are independently one of hydrogen, $C_{1-6}$ alkyl, $C_{3-8}$ cycloalkyl, phenyl, benzyl, trifluoromethyl, halogen, hydroxy($C_{1-8}$)alkyl, cyano, nitro, carboxamido, carboxy, $C_{1-4}$ alkoxycarbonyl, $C_{1-4}$ alkoxymethyl or $C_{1-4}$ alkoxy; or alternatively, $R^2$ and $R^3$, when present on adjacent carbon atoms, may also be taken together to form one of —CH=CH—CH=CH— or —$(CH_2)_q$—, where q is from 2 to 6;
Y is one of —O—, —S—, —$NR^{10}$—, or a covalent bond;
$R^a$, $R^b$ and $R^c$ are each one of hydrogen, $C_{1-4}$ alkyl, hydroxy, $C_{1-4}$ alkoxy, phenoxy, $C_{1-4}$ alkyloxycarbonyl, benzyloxycarbonyl, cyano,

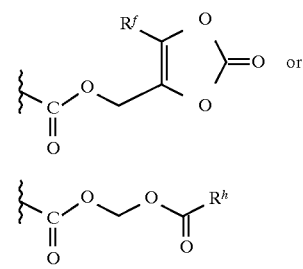

where $R^h$ is benzyl, methyl, ethyl, isopropyl, sec-butyl or t-butyl, and where $R^f$ is hydrogen or $C_{1-6}$ alkyl;
$R^6$ is one of hydrogen, $C_{1-6}$ alkyl, benzyl, phenyl, $C_{2-10}$ hydroxyalkyl, $C_{2-10}$ aminoalkyl, $C_{1-4}$ monoalkylamino ($C_{2-8}$)alkyl, $C_{1-4}$ dialkylamino($C_{2-8}$)alkyl or $C_{2-10}$ carboxyalkyl;
$R^7$ and $R^8$ are independently one of hydrogen, $C_{1-6}$ alkyl, $C_{2-10}$ carboxyalkyl or $C_{2-10}$ hydroxyalkyl, or $R^7$ and $R^8$ are taken together to form —$(CH_2)_y$— where y is zero, 1 or 2;
$R^9$ is hydrogen; or $C_{1-10}$ alkyl, optionally substituted with amino, mono($C_{1-4}$)alkylamino, $C_{1-6}$ alkoxy, hydroxy, carboxy, phenyl, alkyloxycarbonyl, aralkoxycarbonyl, $C_{1-6}$ acylamino, cyano or trifluoromethyl;

$R^{10}$, in each instance, is independently hydrogen, $C_{1-6}$ alkyl, benzyl, phenyl, $C_{2-10}$ hydroxyalkyl, $C_{2-10}$ aminoalkyl, $C_{1-4}$ monoalkylamino($C_{2-8}$)alkyl, $C_{1-4}$ dialkylamino($C_{2-8}$)alkyl or $C_{2-10}$ carboxyalkyl;

n is from zero to 8; and m is from zero to 4.

76. The process of claim 58, wherein $R^1$ is $C_{6-10}$aryl, optionally substituted by one or more substituents independently selected from the group consisting of hydroxy; nitro; trifluoromethyl; halogen; alkyl; alkoxy; aminoalkoxy; aminoalkyl; hydroxyalkyl; hydroxyalkoxy; cyano; amino; monoalkylamino; dialkylamino; carboxy; carboxyalkyl; carboxyalkoxy; mono(hydroxyalkyl)amino; di(hydroxyalkyl) amino; mono(carboxyalkyl)amino; di(carboxyalkyl)amino; alkoxycarbonylamino; alkoxycarbonyl; aralkoxycarbonyl; alkenylcarbonyl; alkynylcarbonyl; alkylsulfonyl; alkenylsulfonyl; alkynylsulfonyl; arylsulfonyl; aralkylsulfonyl; mono- and di-(alkyl)aminosulfonyl; mono- and di-(aryl) aminosulfonyl; mono- and di-(aralkyl)aminosulfonyl; alkylsulfinyl; alkylsulfonamido; arylsulfonamido; aralkylsulfonamido; N-morpholinosulfonyl; N-piperazinylsulfonyl, optionally substituted in the 4-position with alkyl, hydroxyalkyl, aryl or arylalkyl; N-pyrrolylsulfonyl; N-piperidinylsulfonyl; N-pyrrolidinylsulfonyl; N-dihydropyridylsulfonyl; N-indolylsulfonyl; amidino; guanidino; alkyliminoamino; formyliminoamino; trifluoromethoxy and perfluoroethoxy.

\* \* \* \* \*

UNITED STATES PATENT AND TRADEMARK OFFICE
CERTIFICATE OF CORRECTION

PATENT NO. : 5,891,909

DATED : April 6, 1999

INVENTORS : SOLL et al.

It is certified that an error appears in the above-identified patent and that said Letters Patent is hereby corrected as shown below.

Column 81 in Claim 3, line 3 please delete "$C_1$-alkoxy" and insert therein --$C_{1-6}$alkoxy--.

Column 81 in Claim 3, line 4 please delete "($C_1$.)-alkylamino" and insert therein --($C_{1-6}$)alkylamino--.

Column 83 in Claim 19, line 8 please delete "2-[3-[3-($^2$-chlorophenylsulfonyloxy)-5-methoxyphenyl] propyl-1-methylene]- hydrazinecarboximidamide hydrochloride" and insert therein --2-[3-[3-(2-chlorophenylsulfonyloxy)-5-methoxyphenyl]propyl-1-methylene]- hydrazinecarboximidamide hydrochloride--.

Column 89 in claim 69 please delete " —$CH_2)_y$— " and insert therein -- —$(CH_2)_y$— --.

Column 89 in claim 70 please delete " —$CH_2)_t$— " and insert therein -- —$(CH_2)_t$— --.

Signed and Sealed this

Twentieth Day of June, 2000

Attest:

Q. TODD DICKINSON

*Attesting Officer*    *Director of Patents and Trademarks*